United States Patent
Xu et al.

(12) 
(10) Patent No.: US 6,617,109 B1
(45) Date of Patent: Sep. 9, 2003

(54) COMPOSITIONS AND METHODS FOR THE THERAPY AND DIAGNOSIS OF OVARIAN CANCER

(75) Inventors: Jiangchun Xu, Bellevue, WA (US); John A. Stolk, Bothell, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/713,550

(22) Filed: Nov. 14, 2000

Related U.S. Application Data

(63) Continuation-in-part of application No. 09/656,668, filed on Sep. 7, 2000, which is a continuation-in-part of application No. 09/640,173, filed on Aug. 15, 2000, which is a continuation-in-part of application No. 09/561,778, filed on May 1, 2000, now abandoned, which is a continuation-in-part of application No. 09/394,374, filed on Sep. 10, 1999, now abandoned.

(51) Int. Cl.[7] .................... C07H 21/00; A01N 43/04; C12Q 1/68; G01N 33/48; C12P 19/34
(52) U.S. Cl. .................... 435/6; 536/24.3; 536/24.33; 514/23; 514/44; 435/6; 435/91.2; 436/64
(58) Field of Search ................. 536/23.1, 24.3, 536/24.33; 514/23, 44; 435/91.2, 6; 436/64

(56) References Cited

FOREIGN PATENT DOCUMENTS

WO   WO 98/37418   8/1998

OTHER PUBLICATIONS

GenBank Accession No. AI023799 (Jun. 18, 1998).*
Database EMBL Accession No. AA536804, Jul. 31, 1997.
Database EMBL Accession No. AC016957, Dec. 14, 1999.
Database EMBL, Accession No. AF060226, May 6, 1998.
Database EMBL, Accession No. AX001326, Mar. 10, 2000.
Database EMBL, Accession No. X02662, May 7, 1999.
Meden and Kuhn, "Overexpression of the oncogene c–crbB–2 (HER2/neu) in ovarian cancer: a new prognostic factor," *European Journal of Obstetrics & Gyncology and Reproduction Biology* 71:173–179, 1997.
Schena et al., "Quantitative monitoring of gene expression patterns with a complementary DNA microarray," *Science* 270:467–470, Oct. 20, 1995.

\* cited by examiner

*Primary Examiner*—Mary K. Zeman
*Assistant Examiner*—Lori A. Clow
(74) *Attorney, Agent, or Firm*—Eric M. Barzee; Susan E. Lingenfelter; Cynthia L. Shumate

(57) ABSTRACT

Compositions and methods for the therapy and diagnosis of cancer, particularly ovarian cancer, are disclosed. Illustrative compositions comprise one or more ovarian tumor polypeptides, immunogenic portions thereof, polynucleotides that encode such polypeptides, antigen presenting cell that expresses such polypeptides, and T cells that are specific for cells expressing such polypeptides. The disclosed compositions are useful, for example, in the diagnosis, prevention and/or treatment of diseases, particularly ovarian cancer.

9 Claims, No Drawings

SEQUENCE LISTING

<160> NUMBER OF SEQ ID NOS: 205

<210> SEQ ID NO 1
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 1
caacctcact agtaaatgaa agaaatattg taatttgtat ttgatctgct gggtctttgg     60
agtcagaact ggttttatca gcagtttgat cttctgaggt ctggtatgta gtttgctggc    120
ccacagaacc ttcacgtgta ttcacagcct caatgccata aggaaactct tttagaagtt    180
ctgacagctg gtcatgtagg tataagacag gtgccttatc actgtggatt tcatttcttg    240
caggatcttg gggagtatag ttgctggatg catctatttc ctgagggtaa atatcctcct    300
ggncgacgcg gccgctcgag tctagagggc ccgtttaaac ccgctgatca gcctcgactg    360
tgccttctan ttgccancca tntgttgttt gcccct                              396

<210> SEQ ID NO 2

<211> LENGTH: 396
<212> TYPE: DNA
<213> ORGANISM: Homo sapien

<400> SEQUENCE: 2

```
cgaccaaaaa gtaaactcca agtgaacatc aaatcaaatc taatccttttt ggccacatga      60
ctggttgttc tttatctcat agttacaatg aatcatataa actgtagact gccactacca     120
cgatacttct gtgacacaga aggaatgtcc tatttgccta tctatctgag gaatgttaaa     180
tagagaaaaa tagattataa acaacctgg aggtcacagg attctgagat aatccctctg     240
ttaaaaaaca tctgaacagc aaatgtccaa tctgtaataa aatagttaaa ggtccaagtc     300
aagtccactt ctacttggct ggcccagcac aagaaatcta acagcacttt gtaatcattt     360
tgcttttcta attttcccgg aggacatggg ccattg                                396
```

<210> SEQ ID NO 3
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 3

```
cgcccttttt tttttttttt tnattggnnn aantcncttt nantnnaaaa acntgnangg      60
naancccann cccnnggnac cannnccagg agttgggtgg anactgagtg gggtttgtgt     120
gggtgagggg gcatctactc ctnttgcaac aagccaaaag tagaacagcc taaggaaaag     180
tgacctgcct tggagcctta gtccctccct tagggccccc tcagcctacc ctatccaagt     240
ctgaggctat ggaagtctcc ctcctagttc actagcaggt tccccatctt ttccaggctg     300
ccctagcac tccacgtttt tctgaaaaaa tctanacagg ccctttttgg gtacctaaaa     360
cccagctgag gttgtgagct tgtaaggtaa agcaag                                396
```

<210> SEQ ID NO 4
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 4

```
gaccaatcct tgncncacta ncaaaangac cccnctnacc nccaggaact gaacctnnnt      60
gtnnacctcc nnctgcnnag ccntatntcc aanatcaccc accgtatcca ctgggaatct     120
gccagcctcc tgcgatcaga agagaccaat cgaaaatgag ggtttcacan tcacagctga     180
aggaaaaggc caaggcacct tgtcggnggn gacaatgtac catgctaagg ccaaagatca     240
actcacctgt aataaattcg acctcaaggt caccataaaa ccagcaccgg aacagaaaaa     300
gaggcctnag gatgcccaag aaaacacttttt gatcctttga aaactgtacc aaggtaccgg     360
ggggagaccc aggaaaggnc cnttatgtnt nnntnt                                396
```

<210> SEQ ID NO 5
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 5

```
gacgccggag ctgccgcgcc agtcgcctag caggtcctct accggcttat tcctgtgccg    60
gatcttcatc ggcacagggg ccactgagac gtttctgcct ccctctttct tcctccgctc   120
tttctcttcc ctctngttta gtttgcctgg gagcttgaaa ggagaaagca cngggtcgc    180
cccaaaccct ttctgcttct gcccatcaca agtgccacta ccgccatggg cctcactatc   240
tcctccctct tctcccgact atttggcaag aagcagatgc gcattttgat ggttggattg   300
gatgctgctg gcaagacaac cattcttgat aaactgaaag tangggganat aagnaccacc   360
atttctacca ttgggtttaa tgggggaaac agtana                              396
```

<210> SEQ ID NO 6
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 6

```
acgggaggcg ccgggaagtc gacggcgccg gcggctcctg caggaggcca ctgtctgcag    60
ctcccgtgaa gatgtccact ccagaccac ccctgggcgg aactcctcgg ccaggtcctt    120
ccccgggccc tgcccttccc ctggagccat gctgggccct agcccgggtc cctcgccggg   180
ctccgcccac agcatgatgg ggcccagccc angggccgcc ctcagcagga cacccatcc    240
ccacccaggg gcctggaggg taccctcagg acaacatgca ccagatgcac aagcccatgg   300
agtccatgca tgagaagggc atgtcggacg acccgcgcta caaccagatg aaaggaatgg   360
ggatgcggtc aggggccat gctgggatgg ggcccc                              396
```

<210> SEQ ID NO 7
<211> LENGTH: 396
<212> TYPE: DNA
<213> ORGANISM: Homo sapien

<400> SEQUENCE: 7

```
acccgagagt cgtcggggtt tcctgcttca acagtgcttg gacggaaccc ggcgctcgtt    60
ccccaccccg gccggccgcc catagccagc cctccgtcac ctcttcaccg caccctcgga   120
ctgcccaag gccccgccg ccgctccagc gccgcgcagc caccgccgcc gccgccgcct   180
ctccttagtc gccgccatga cgaccgcgtc cacctcgcag gtgcgccaga actaccacca   240
ggactcagag gccgccatca accgccagat caacctggag ctctacgcct cctacgttta   300
cctgtccatg tcttactact ttgaccgcga tgatgtggct ttgaagaact ttgccaaata   360
ctttcttcac caatctcatg aggagaggga acatgc                             396
```

<210> SEQ ID NO 8
<211> LENGTH: 396
<212> TYPE: DNA
<213> ORGANISM: Homo sapien

<400> SEQUENCE: 8

```
cgacaacaag gttaataccct tagttcttaa cattttttt ctttatgtgt agtgttttca    60
tgctaccttg gtaggaaact tatttacaaa ccatattaaa aggctaattt aaatataaat   120
```

-continued

| | |
|---|---|
| aatataaagt gctctgaata aagcagaaat atattacagt tcattccaca gaaagcatcc | 180 |
| aaaccaccca aatgaccaag gcatatatag tatttggagg aatcaggggt ttggaaggag | 240 |
| tagggaggag aatgaaggaa aatgcaacca gcatgattat agtgtgttca tttagataaa | 300 |
| agtagaaggc acaggagagg tagcaaaggc caggcttttc tttggttttc ttcaaacata | 360 |
| ggtgaaaaaa acactgccat tcacaagtca aggaac | 396 |

<210> SEQ ID NO 9
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 9

| | |
|---|---|
| tcgacatcgc ggcaactttt tgcggattgt tcttgcttcc aggctttgcg ctgcaaatcc | 60 |
| agtgctacca gtgtgaagaa ttccagctga acaacgactg ctcctccccc gagttcattg | 120 |
| tgaattgcac ggtgaacgtt caagacatgt gtcagaaaga agtgatggag caaagtgccg | 180 |
| ggatcatgta ccgcaagtcc tgtgcatcat cagcggcctg tctcatcgcc tctgccgggt | 240 |
| accagtcctt ctgctcccca gggaaactga actcagtttg catcagctgc tgcaacaccc | 300 |
| ctctttgtaa cgggccaagg nccaaaaaaa ggggaaagtt ctgncctcgg ccctcaggcc | 360 |
| agggctccgc accaccatcc tgttcctcaa attagc | 396 |

<210> SEQ ID NO 10
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 10

| | |
|---|---|
| cctttttttt tttttttttt tttttttttt tttttttttt tttttttttt tttttttttt | 60 |
| tttttttttt tttttttttt tttttttttt tttttttttt ttttaaaaaa aaaannnttt | 120 |
| tttttttttn aaaaaaangg gnnnnntttt ttncccnnnn gggnggggggg ggggnnnnnt | 180 |
| ttnaaanaaa aaaaccnnaa annnnngggg nnnannnaan nncccncccc naancnntaa | 240 |
| aaaannnggn aaaanagggg gggnannnnn nngggggggna aaantttttt tttttnaag | 300 |
| ggnnnggnaa aaaantnnnn nnnttttttt ttnnaanngg gnnaaaaaaa aaaaaaaaaa | 360 |
| attttttngg gntnaggggn nggggaaaa ncccna | 396 |

<210> SEQ ID NO 11
<211> LENGTH: 396
<212> TYPE: DNA
<213> ORGANISM: Homo sapien

<400> SEQUENCE: 11

| | |
|---|---|
| agaacacagg tgtcgtgaaa actacccta aaagccaaaa tgggaaagga aaagactcat | 60 |
| atcaacattg tcgtcattgg acacgtagat tcgggcaagt ccaccactac tggccatctg | 120 |
| atctataaat gcggtggcat cgacaaaaga accattgaaa aatttgagaa ggaggctgct | 180 |
| gagatgggaa agggctccct caagtatgcc tgggtcttgg ataaactgaa agctgagcgt | 240 |
| gaacgtggta tcaccattga tatctccttg tggaaatttg agaccagcaa gtactatgtg | 300 |

```
actatcattg atgccccagg acacagagac tttatcaaaa acatgattac agggacatct    360
caggctgact gtgctgtcct gattgttgct gctggt                              396
```

<210> SEQ ID NO 12
<211> LENGTH: 396
<212> TYPE: DNA
<213> ORGANISM: Homo sapien

<400> SEQUENCE: 12

```
cgaaaacctt taaaccccgg tcatccggac atcccaacgc atgctcctgg agctcacagc     60
cttctgtggt gtcatttctg aaacaagggc gtggatccct caaccaagaa gaatgtttat    120
gtcttcaagt gacctgtact gcttgggac tattggagaa aataaggtgg agtcctactt     180
gtttaaaaaa tatgtatcta agaatgttct agggcactct gggaacctat aaaggcaggt    240
atttcgggcc ctcctcttca ggaatcttcc tgaagacatg gcccagtcga aggcccagga    300
tggcttttgc tgcggccccg tggggtagga gggacagaga gacagggaga gtcagcctcc    360
acattcagag gcatcacaag taatggcaca attctt                              396
```

<210> SEQ ID NO 13
<211> LENGTH: 396
<212> TYPE: DNA
<213> ORGANISM: Homo sapien

<400> SEQUENCE: 13

```
accacaggct ggccacaaga agcgctggag tgtgctggcg gctgcaggcc tacggggcct     60
ggtccggctg ctgcacgtgc gtgccggctt ctgctgcggg gtcatccgag cccacaagaa    120
ggccatcgcc accctgtgct tcagccccgc ccacgagacc catctcttca cggcctccta    180
tgacaagcgg atcatcctct gggacatcgg ggtgcccaac caggactacg aattccaggc    240
cagccagctg ctcacactgg acaccacctc tatccccctg cgcctctgcc ctgtcgcctc    300
ctgcccggac gcccgcctgc tggccggctg cgagggcggc tgctgctgct gggacgtgcg    360
gctggaccag ccccaaaaga ggagggtgtg tgaagt                              396
```

<210> SEQ ID NO 14
<211> LENGTH: 396
<212> TYPE: DNA
<213> ORGANISM: Homo sapien

<400> SEQUENCE: 14

```
acggcgtcct cgtggaagtg acatcgtctt taaaccctgc gtggcaatcc ctgacgcacc     60
gccgtgatgc ccagggaaga cagggcgacc tggaagtcca actacttcct taagatcatc    120
caactattgg atgattatcc gaaatgtttc attgtgggag cagacaatgt gggctccaag    180
cagatgcagc agatccgcat gtcccttcgc gggaaggctg tggtgctgat gggcaagaac    240
accatgatgc gcaaggccat ccgagggcac ctggaaaaca cccagctctg gagaaactg    300 ctgcctcata tccggggaa tgtgggcttt gtgttcacca aggaggacct cactgagatc    360
agggacatgt tgctggccaa taaggtgcca gctgct                              396
```

<210> SEQ ID NO 15
<211> LENGTH: 396
<212> TYPE: DNA
<213> ORGANISM: Homo sapien
<220> FEATURE:
<221> NAME/KEY: misc_feature
<222> LOCATION: (1)...(396)

<223> OTHER INFORMATION: n = A,T,C or G

<400> SEQUENCE: 15

| accgcgcggg | cacagggtgc | cgctgaccga | ggcgtgcaaa | gactccagaa | ttggaggcat | 60 |
| gatgaagact | ctgctgctgt | tgtgggggct | gctgctgacc | tgggagagtg | gcaggtcct | 120 |
| ggggaccag | acggtctcag | acaatgagct | ccaggaaatg | tccaatcagg | gaagtaagta | 180 |
| cgtcaataag | gaaattcaaa | atgcttgtca | acgggtgaa | acagataaag | actctcatag | 240 |
| aaaaaacaaa | cgaagagcgc | aagacactgc | tcagcaacct | agaagaagcc | aagaagaaga | 300 |
| aagaggatgc | cctaaatgag | accagggaat | canagacaaa | gctgaaggag | ctcccaggag | 360 |
| tgtgcaatga | gaccatgatg | gccctctggg | aagagt | | | 396 |

<210> SEQ ID NO 16
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 16

| tttttttttt | tttttttttt | tttttttttt | tttttttttt | tttttttttt | tttttttttt | 60 |
| tttttttttt | tttttttttt | tttttttttt | tttttttttt | tttttttttt | tttnggggggg | 120 |
| nnnaaantt | tttntnanan | nnnngggnaa | aaaaaaaaa | aanaangggg | gnnntnnggc | 180 |
| ccnnnanaaa | aaaanngnna | annaaanccccc | ccnnnnnnnc | ccncnnntnn | ggaaananna | 240 |
| aaacccccccc | cngggnnggg | nnaaaaaannc | ccngggggnan | tttttatnnn | anncccccccc | 300 |
| ccnggggggg | gnggaaaaaa | aaaantnccc | ccnannaaaa | nngggggnccc | cccnttttnc | 360 |
| aaaanggggg | nccgggcccc | ccnnantntt | nggggg | | | 396 |

<210> SEQ ID NO 17
<211> LENGTH: 396
<212> TYPE: DNA
<213> ORGANISM: Homo sapien

<400> SEQUENCE: 17

| accacactaa | ccatataccca | atgatggcgc | gatgtaacac | gagaaagcac | ataccaaggc | 60 |
| caccacacac | cacctgtcca | aaaaggcctt | cgatacggga | taatcctatt | tattacctca | 120 |
| gaagttttt | tcttcgcagg | attttttctga | gccttttacc | actccagcct | agcccctacc | 180 |
| ccccaactag | gagggcactg | gccccccaaca | ggcatcaccc | cgctaaatcc | cctagaagtc | 240 |
| ccactcctaa | acacatccgt | attactcgca | tcaggagtat | caatcacctg | agctcaccat | 300 |
| agtctaatag | aaaacaaccg | aaaccaaata | attcaagcac | tgcttattac | aatttttactg | 360 |
| ggtctctatt | ttaccctcct | acaagcctca | gagtac | | | 396 |

<210> SEQ ID NO 18
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 18

| tttttttttt | tttttttttt | tttttttttt | tttttttttt | tttttttttta | ntcnaaaggg | 60 |

```
gaaggnccct tttttattaaa nttggncatt ttactttnct tttttnaaaa ngctaanaaa      120 aaantttttnt ttntncttaa aaaaaccctn natntcacna ncaaaaaaaa cnattcccnc      180 ntncntttg tgataaaaaa aaaggcaatg gaattcaacn tancctaana aaactttncc       240
tgggaggaaa aaaaattnnt ccgngggaaa cacttgggc tntccaaant gnanccatnc        300
tangaggacc ntctntaaga tttccaaang aaacccttc ctnccaaang nantaccccg        360
ntgcctacnn cccataaaaa aaacctcanc cntaan                                 396
```

```
<210> SEQ ID NO 19
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 19
```

```
tttttttttt tttttttttt tttttttttt tttttttttt tttttttntgg tctgggcttt      60 tatttttacna aaaanctaan ggnaaanntn cnttaaacta antngaaanac aaagtnttaa     120 ngaaaaaggn ctgggggnnt cntttacaaa aanggncngg gncannttg ggcttaaaan       180 ttcaaaaagg gnncntcaaa ngggtttgca tttgcatgtt tcancnctaa ancgnangaa      240
naaacccngg ngccnctgg gaaaagttnt tnanctncca aaaanatnaan tntttgnanc      300 agggnntttt tgggnaaaaa aannnanttcc anaaactttc catccctgg ntttgggttc     360 ggccttgngt tttcggnatn atntccntta angggg                                396
```

```
<210> SEQ ID NO 20
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 20
```

```
tttttttttt tttttttttt ttttttctna acaaaccctg ttnttgggng ggngngggta      60
taatactaag ttganatgat ntcatttacg ggggaaggcn ctttgtgaan naggccttat     120
ttctnttgnc ctttcgtaca gggaggaatt tgaagtaaan anaaaccnac ctggattact     180
ccggtctgaa ctcaaatcac gtaggacttt aatcgttgaa caaacaaacc tttaatagcg    240
gctgcnccat tgggatgtcc tgatccaaca tcgaggncgt aaaccctatt gttgatatgg    300
actctaaaaa taggattgcg ctgttatccc tagggtaact tgttcccgtg gtcaaagtta    360
ttggatcaat tgagtataag tagttcgctt tgactg                                396
```

```
<210> SEQ ID NO 21
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 21
```

```
acatanatnt tatactanca ttnaccatct cacttgnagg aanactanta tatcnctcac      60
```

-continued acctnatatc ctncntacta tgcctagaag gaataatact atngctgttn attatancta    120
ctntnataac cctnaacacc cactccctct tanccaatat tgtgcctatt gccatactag    180
tntttgccgc ctgcnaagca gnggngggcc tanccntact agnctcaatc tccaacacnt    240
atggcctana ctacgtacat aacctaaacc tactcnaatg ctaaaactaa tcnncccaac    300
anttatntta ctaccactga catgactttc caaaaaacac atantttgaa tcaacncanc    360
cacccacanc ctanttatta ncatcatccc cntact                              396

<210> SEQ ID NO 22
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 22 ttttttttt ttttganaaa agccggcata aagcacttttt attgcaataa taaaacttga    60
gactcataaa tggtgctggg ggaagggtgc agcaacgatt tctcaccaaa tcactacaca    120
ggacagcaaa ggggtgagaa ggggctgagg gaggaaaagc caggaaactg agatcagcag    180
agggagccaa gcatcaaaaa acaggagatg ctgaagctgc gatgaccagc atcattttct    240
taanagaaca ttcaaggatt tgtcatgatg gctgggcttt cactgggtgt taagtctaca    300
aacagcacct tcaattgaaa ctgtcaatta agttcttaa gatttaggaa gtggtggagc     360
ttggaaagtt atgagattac aaaattcctg aaagtc                               396

<210> SEQ ID NO 23
<211> LENGTH: 396
<212> TYPE: DNA
<213> ORGANISM: Homo sapien

<400> SEQUENCE: 23
acaaaggcgg ttccaagcta aggaattcca tcagtgcttt tttcgcagcc accaaattta    60
gcaggcctgt gaggttttca tatcctgaag agatgtattt taaagctttt tttttttaat    120
gaaaaaatgt cagacacaca caaaagtaga atagtaccat ggagtcccca cgtacccagc    180
ctgcagcttc aacagttacc acatttgcca accggagaga ctgccaaggc aggaaaaagc    240
cctggaaagc ccacggcccc ttttttcccctt gggtcagagg ccttagagct ggctgccaaa    300
gcagccaacc aaaggggcag ctcagctcct tcgtggcacc agcagtgttc ctgatgcagt    360
tgaagagttg atgtctttga caacatacgg acactg                               396

<210> SEQ ID NO 24
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 24
cgactatcct ctcagattct tatctggcac taatttataa ctattatatt atcagagact    60
atgtagcaat atatcagtgc acaggcgcat cccaggcctg tacagatgta tgtctacacg    120
taagtataaa tgaatttgca taccaggttt tacacttgca tctctaatag agattaaaaa    180
caacaaattg gcctcttcct aagtatatta atatcattta tccttacatt ttatgcctcc    240

| | |
|---|---|
| ccctaaatta atgactgagt tggtggaaag cggctaggtt ttattcatac tgttttttgt | 300 |
| tctcaacttc aanagtaatc tacctctgaa aaatttntan tttaatattn nnnnnnagga | 360 |
| atttgngcca ctttannnct tncnntntnn tnnccn | 396 |

<210> SEQ ID NO 25
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 25

| | |
|---|---|
| tttttttttt tttttttttt gtcttttaaa aaatataaaa gtgttattat tttaaaacat | 60 |
| caagcattac agactgtaaa atcaattaan aactttctgt atatgaggac aaaaatacat | 120 |
| ttaanacata tacaanaaga tgcttttttcc tgagtagaat gcaaacttttt atattaagct | 180 |
| tctttgaatt ttcaaaatgt aaaataccaa ggctttttca catcagacaa aaatcaggaa | 240 |
| tgttcacctt cacatccaaa aagaaaaaaa aaaaaaancc aattttcaag ttgaagttna | 300 |
| ncaanaatga tgtaaaatct gaaaaaagtg gccaaaattt taanttncaa cananngnn | 360 |
| ncagntttna tggatctntn nnnnnncttc nnntnn | 396 |

<210> SEQ ID NO 26
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 26

| | |
|---|---|
| gacgctcccc cctcccccccg agcgccgctc cggctgcacc gcgctcgctc cgagtttcag | 60 |
| gctcgtgcta agctagcgcc gtcgtcgtct cccttcagtc gccatcatga ttatctaccg | 120 |
| ggacctcatc agccacgatg agatgttctc cgacatctac aagatccggg agatcgcgga | 180 |
| cgggttgtgc ctggaggtgg aggggaagat ggtcagtagg acagaaggta acattgatga | 240 |
| ctcgctcatt ggtggaaatg cctccgctga aggccccgag ggcgaaggta cccgaaagca | 300 |
| cagtaatcac tgnngncnat nttgtcatga accatcacct gcnngaaaca annttnacaa | 360 |
| aanaancctn cnnnnannnc ctnnnnnatt ncnnnn | 396 |

<210> SEQ ID NO 27
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 27

| | |
|---|---|
| tttttttttt tttttttttt tttttttttt tttttttttt tggctaaant ttatgtatac | 60 |
| nggttnttca aangngggg agggggggggg gcatccatnt anncncncca ggtttatggn | 120 |
| gggntnttnt actattanna nttttcncctt caaancnaag gnttntcaaa tcatnaaaat | 180 |
| tattaanatt ncngctgnta aaaaaangaa tgaaccnncn nanganagga nntttcatgg | 240 |

```
ggggnatgca tcggggnann ccnaanaacc ncggggccat tcccganagg cccaaaaaat    300
gtttnnnnaa aaagggtaaa nttaccccccn tnaantttat annnnaaann nnannnnagc    360
ccaannnttn nnnnnnnnnn nnnccnnnna nnnnnn                              396
```

```
<210> SEQ ID NO 28
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 28
cgaccttttt tttttttttt atagatgaaa gagggtttat ttattaatat atgatagcct    60
tggctcaaaa aagacaaatg agggctcaaa aaggaattac agtaacttta aaaaatatat   120
taaacatatc caagatccta aatatattat tctccccaaa agctagctgc ttccaaactt   180
gatttgatat tttgcatgtt ttccctacgt tgcttggtaa atatatttgc ttctcctttc   240
tgcaatcgac gtctgacagc tgattttttgc tgttttgnca acntgacgtt tcaccttntg   300
tttcaccant tctggaggaa ttgttnaaca ncttacanca ctgccttgaa naaannnnan   360
gcctcaaaag ntcttgnnct atnctnnttc ntnnnt                              396
```

```
<210> SEQ ID NO 29
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 29
gacttgctca tttagagttt gcaggaggct ccatactagg ttcagtctga aagaaatctc    60
ctaatggtgc tatagagagg gaggtaacag aaagactctt ttagggcatt tttctgactc   120
atgaaaagag cacagaaaag gatgtttggc aatttgtctt ttaagtctta accttgctaa   180
tgtgaatact gggaaagtga ttttttttctc actcgttttt gttgctccat tgtaaagggc   240
ggaggtcagt cttagtggcc ttgagagttg cttttggcat ttaaatattc taagagaatt   300
aactgtattt cctgtcacct attcactant gcangaaata tacttgctcc aaataagtca   360
ntatgagaag tcactgtcaa tgaaanttgn tttgtt                              396
```

```
<210> SEQ ID NO 30
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 30
tttttttttt tttttttttg aaatttanaa acaaattttta tttaagatct gaaatacaat    60
tcctaaaata tcaactttc canaaaaccg tggctacaca ataatgcatt gcctctatca    120
tgttanaacg tgcattanac tcaaatacaa aaaccatgaa acaaatcacc atccttcaac   180
aatttgagca aagatagaat gcctaagaac aacatagatg gacttgcaga ggatgggctg   240
ttttacttca agcnccataa aaaaaaaaaa gagcncaaat gcattgggtt ttcaggtnta   300
```

```
tacattaagn ngaacctttg gcactaggaa tcagggcgtt ttgtcacata gcnttaacac    360
atnttaaaaa attntgtant gtcaaaggga tangaa                              396
```

<210> SEQ ID NO 31
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 31

```
gacgggccag ggccatctgg aaagggaact cggcttttcc agaacgtggt ggatcatctg     60
tcgggtgtgt ggtgaacacg ttcagttcat cagggcctac gctccgggaa ggggccccca    120
gctgtggctc tgccatgccg ggctgtgttt gcagctgtcc gagtctccat ccgcctttag    180
aaaaccagcc acttcttttc ataagcactg acagggccca gcccacagcc acaggtgcga    240
tcagtgcctc acgcaggcaa atgcactgaa acccaggggc acacncncgc agagtgaaca    300
gtgagttccc ccgacagccc acgacagcca ggactgccct ccccacccnn ccccgacccc    360
angancacgg cacacanntc ancctctnan ctngct                              396
```

<210> SEQ ID NO 32
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 32

```
cgactggcct cataccttgt ctacacagtc cctgcacagg gttcctaacc tgtggttagt     60
aaagaatgtc actttctaac aggtctggaa gctccgagtt tatcttggga actcaagagg    120
agaggatcac ccagttcaca ggtatttgag gatacaaacc cattgctggg ctcggcttta    180
aaagtcttat ctgaaatcc ttgtgaaaca gagtttcatc aaagccaatc caaaaggcct    240
atgtaaaaat aaccattctt gctgcacttt atgcaaataa tcaggccaaa tataagacta    300
cagtttattt acaatttgtt tttaccaaaa atgaggacta nagagaaaaa tggtgctcca    360
aagcttatca tacattgtc attaagtcct agtctc                               396
```

<210> SEQ ID NO 33
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 33

```
ccttttttt ttttttttt ttttttttt ttttttttt ttttttttt ttttttttt           60 ttttttttt ttttttttt ttttttttt ttttttttt ttttttttt ttttttttt          120 nngnnntntn nnnannaaaa annnnnnna aaaaaannn nnnnnnnt                    180 tttnngggg gnttttnann gnannttnnn nttnnnnnaa anccccnnng ggnngggggg      240
nntnnnnnng gnaaaaaaan nnnngggn cnnngggnc cncncccnan nnnaaaann        300
```

```
nnnggnttttt ttnnttttna aaaaaanngn nnnnnaacaa aantttttnn nnaanttttn      360
gggggaaann ncccntttnt tttttttnnan nnnnnn                                396

<210> SEQ ID NO 34
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 34
acggaccnag ctggaggagc tgggtgtggg gtgcgttggg ctggtgggga ggcctagttn       60
gggtgcaagt angtctgatt gagcttgtgt tgtgctgaag ggacagccct gggtctaggg      120
ganagagncc ctgagtgtga gacccaccct ccccngtccc agcccctccc anttccccca     180
gggacggcca cttcctgntc cccgacncaa ccatggctga agaacaaccg caggtcgaat      240
tgttcntgaa ggctggcagt gatggggcca agattgggaa ctgcccattc tcccacagac     300
tgttnatggt actgtggctc aaggnagtca ccttcaatgt taccaccnnt gacaccaaaa     360
ggcggaccna nacagtgcan aagctgtgcc canngg                                396

<210> SEQ ID NO 35
<211> LENGTH: 396
<212> TYPE: DNA
<213> ORGANISM: Homo sapien

<400> SEQUENCE: 35
tcgaccaaaa tcaaatctgg cactcacaag ccctggccga cccccaatgg gttttaccac       60 tcccctcta gaccctgtct tgcaaaatcc tctccctagc cagctagtat tttctgggct      120
aaagactgta caaccagttc ctccatttta tagaagttta ctcactccag gggaaatggt     180
gagtcctcca acctcccttt caaccagtcc catcattcca accagtggta ccatagagca     240
gcaccccccg ccacctctg agccagtagt gccagcagtg atgatggcca cccatgagcc      300
cagtgctgac ctggcaccca agaaaaagcc caggaagtca agcatgcctg tgaagattga     360
gaaggaaatt attgataccg ccgatgagtt tgatga                                396

<210> SEQ ID NO 36
<211> LENGTH: 396
<212> TYPE: DNA
<213> ORGANISM: Homo sapien

<400> SEQUENCE: 36
tcgacgggaa gagcctgcta cggtggactg tgagactcag tgcactgtcc tcctcccagc      60
gaccccacgc tggaccccct gccggaccct ccacccttcg gccccaagc ttcccagggg      120 cttcctttgg actggactgt ccctgctcat ccattctcct gccaccccca gacctcctca     180
gctccaggtt gccacctcct ctcgccagag tgatgaggtc ccggcttctg ctctccgtgg     240
cccatctgcc cacaattcgg gagaccacgg aggagatgct gcttgggggt cctggacagg     300 agccccacc ctctccctagc ctggatgact acgtgaggtc tatatctcga ctggcacagc    360
ccacctctgt gctggacaag gccacggccc agggcc                                396

<210> SEQ ID NO 37
<211> LENGTH: 396
<212> TYPE: DNA
<213> ORGANISM: Homo sapien
```

```
<220> FEATURE:
<221> NAME/KEY: misc_feature
<222> LOCATION: (1)...(396)
<223> OTHER INFORMATION: n = A,T,C or G

<400> SEQUENCE: 37
cgacggtgtc agcaactggc catgccacag cacataaaga ttacagtgac aagaaaaaca      60
ttgtttgagg attcctttca acagataatg agcttcagtc cccaagatct gcgaagacgt     120
ttgtgggtga tttttccagg agaagaaggt ttagattatg gaggtgtagc aagagaatgg     180
ttctttcttt tgtcacatga agtgttgaac ccaatgtatt gcctgtttga atatgcaggg     240
aaggataact actgcttgca gataaacccc gcttcttaca tcaatccaga tcacctgaaa     300
tattttcgtt ttattggcag atttattgcc atggctctgt tccatgggaa aattcataga     360
cacgggtttt tctttnccat tctataagcg tatctt                               396

<210> SEQ ID NO 38
<211> LENGTH: 396
<212> TYPE: DNA
<213> ORGANISM: Homo sapien

<400> SEQUENCE: 38
cgaccaaaat gataaatagc tttaagaatg tgctaatgat aaatgattac atgtcaattt      60
aatgtactta atgtttaata ccttatttga ataattacct gaagaatata ttttttagta     120
ctgcatttca ttgattctaa gttgcacttt ttaccccat actgttaaca tatctgaaat      180
cagaatgtgt cttacaatca gtgatcgttt aacattgtga caagtttaa tggacagttt      240 tttcccatat gtatatataa aataatgtgt tttacaatca gtggcttaga ttcagtgaaa     300
tacagtaatt cattcaatta tgatagtatc tttacagaca ttttaaaaat aagttatttt     360
tatatgctaa tattctatgt tcaagtggaa tttgga                               396

<210> SEQ ID NO 39
<211> LENGTH: 396
<212> TYPE: DNA
<213> ORGANISM: Homo sapien

<400> SEQUENCE: 39
tcgaccaaga atagatgctg actgtactcc tcccaggcgc cccttccccc tccaatccca      60
ccaaccctca gagccacccc taaagagata ctttgatatt ttcaacgcag ccctgctttg     120
ggctgccctg gtgctgccac acttcaggct cttctccttt cacaaccttc tgtggctcac     180 agaaccttg gagccaatgg agactgtctc aagagggcac tggtggcccg acagcctggc     240
acagggcaag tgggacaggg catggccagg tggccactcc agacccctgg cttttcactg     300
ctggctgcct tagaaccttt cttacattag cagtttgctt tgtatgcact ttgtttttt      360 ctttgggtct tgtttttttt ttccacttag aaattg                               396

<210> SEQ ID NO 40
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 40 ttttttttt tttgttatt tagttttat ttcataatca taaacttaac tctgcaatcc      60
```

```
agctaggcat gggagggaac aaggaaaaca tggaacccaa agggaactgc agcgagagca      120
caaagattct aggatactgc gagcaaatgg ggtggagggg tgctctcctg agctacagaa      180
ggaatgatct ggtggttaan ataaaacaca agtcaaactt attcgagttg tccacagtca      240
gcaatggtga tcttcttgct ggtcttgcca ttcctggacc caaagcgctc catggcctcc      300
acaatattca tgccttcttt cactttgcca acaccacat gcttgccatc caaccactca       360
gtcttggcag tgcanatgaa aaactgggaa ccattt                                396
```

<210> SEQ ID NO 41
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 41

```
tcgacctctt gtgtagtcac ttctgattct gacaatcaat caatcaatgg cctagagcac      60
tgactgttaa cacaaacgtc actagcaaag tagcaacagc tttaagtcta aatacaaagc      120
tgttctgtgt gagaattttt taaaaggcta cttgtataat aacccttgtc attttttaatg    180 tacaaaacgc tattaagtgg cttagaattt gaacatttgt ggtctttatt tactttgctt     240
cgtgtgtggg caaagcaaca tcttccctaa atatatatta cccaaagnaa aagcaagaag    300
ccagattagg ttttttgacaa acaaacagg ccaaaagggg gctgacctgg agcagagcat     360
ggtgagaggc aaggcatgag agggcaagtt tgttgt                                396
```

<210> SEQ ID NO 42
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 42

```
ctttttttt tttttttttt tttttttttt tttttttttt tttttttttt tttttttttt      60
aaaanccnna nnaananang gnaannnann aaaaaannca aaccncntnt anaaaangcc    120
nntntnaggg gggggttca aaccaaang gnngntgga ngnaaannna aaantttnnnn       180 ggggnanaa anaaaaaggg nngaaanntg acccnanaan gaccngaaan cccgggaaac     240
cnngggntan aaaaaaagnt ganccctaaa nncccccgna aaangggga agggnaannc     300 caaatccnnt gngggttggg ggnggggaaa aaaaaaccc cnaaaaantg naaaaaaccg     360
ggnttnaaan atttgggttc ggggnttttn tnttaa                                396
```

<210> SEQ ID NO 43
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 43

```
tttttttttt ttttgcttca ctgctttatt tttgaaatca caagcaattc aaagtgatca     60
tcattgaggc ttctgttaaa agttcttcca aagttgccca gttttaanat taaacaatat   120
```

```
tgcactttaa gatgaactaa cttttgggat tctcttcaaa gaaggaaagt attgctccat    180
ctgtgctttt cttanactaa aagcatactg canaaaactc tattttaaaa atcaacactg    240
cagggtacag taacatagta aagtacctgc ctattttana atcctanaga acatttcatt    300
gtaagaaact agcccattat ttaagtgtcc acagtatttt tcatttcant ggtccaagat    360
gccaaggttt ccaaacacaa tcttgttctc taatac                              396
```

<210> SEQ ID NO 44
<211> LENGTH: 396
<212> TYPE: DNA
<213> ORGANISM: Homo sapien

<400> SEQUENCE: 44

```
gacctagttt tacctcttaa atatctctgt tcccttctaa gttgtttgct gtgttttctt    60
cagagcaaga aggttatatt ttttaaaatt tacttagtaa tgcacattca aaacacacat    120
caagtcttca ggataaagtt caaaaccgct gtcatggccc catgtgatct ctccctcccc    180 taccctcta tcatttagtt tcttctgcgc aagccactct ggcttccttt cagttttgtg     240
gttcccgttt ttagctagtt cagtggtttt caatgggcat ttcttgcctt ttttttttcta  300 aacgacaaat agaaatacat cttctttatt atcctccaaa tccaattcag aggtaatatg    360
ctccacctac acaattttt agaaataaat taaaaa                               396
```

<210> SEQ ID NO 45
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 45

```
tttttttttt ttttaaannt tntaaatttt taatgaaann ganttagaac aatgtattat    60
tnacatgtaa ataaaaaaag agancataan ccccatatnc tcnnnaaagg aagggganacn   120 gcnggccntt tatnagaana nnnnncatat aagaccccat taagaagaat ctggatctaa    180
anacttncaa acaggagttc acagtangtg aacagcannc cctaatccca ctgatgtgat    240
gnttcanata aaatcancan cgntgatcgg gnatcnnanc aatntgancg gaanannact    300
gctcnatatn tttnaggann cngatgtggt catttttttac aaagataatg gccacaccct   360
tccngnccga atcgancnga nctcccnntt ctgtgn                              396
```

<210> SEQ ID NO 46
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 46

```
tttttttttt ttttttttc tganacagag tctcattctg ttgcctaggc tggattgcag     60
tggtgccatc tcggctcact gcaacctccg cctcctgggt tccanaaatt ctcctgcctc    120
agcctcccgg gtagctggga ctanaggcac acgccaccac gccaggctaa ttttttatatt  180 tttagtanan atggcgtttc accatgttga ccanactgat ctcgaactcc cgacctcgtg    240
```

-continued

```
atccacccac ctcggcctcc caaagtgctg ggattacagg cgtgaaacca ccaggcccgg      300
cctgaaatat ctatttnttt tcagattatt tttaaaattc catttgatga atcttttaaa      360
gtgagctana naaagtgngt gtgtacatgc acacac                                396
```

<210> SEQ ID NO 47
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 47

```
tttttttttt ttttttgct gttgccaact gtttattcag ggccctgaac gggtggtgcg       60
tggacatgca acacactcgg gcccacagca gcgtgaccgg ccgctcccaa gccccgggcg     120
cacaaccaca gccaggagca gcccctgcca ccactgggcc accgtccagg gccccacagg     180
accagccgaa ggtgccccgg gccgaggcca gctgggtcag gtgtacccct agcctggggt     240
tgagtgagga gcggcacccc cagtatcctg tgtaccccaa gttgcccagn aggccgaggg     300
ggccttgggc tccatctgca ctggccaccc cgtgccaagc atcacagctg cgtgagcagg     360
tttgtgtgtg agcgtgtggc ggggcctggt tgtccc                                396
```

<210> SEQ ID NO 48
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 48

```
ctgggcctgt gccgaagggt ctgggcagat cttccaaaga tgtacaaaat gtagaaattg       60
ccctcaagca aatgcaaaga tgctcaacac ccttagtcat caagaaaatg caaatggaat     120
ccacagagag atactgcaca ctgacaaaga tggtcgtatt actaaaggtg aataaccagc     180
gcggggggca cgtggagtca ctggaacatt tgtgcaatgc tggtgggaat gtcaacccgt     240
gcggccctct ggaataagcc tggcagctcc tccaagagtt acccgtgtga cccagcaatt     300
ccactcctag ctcccaccac aggaattgaa agcaaagacg caaacagatg cctgtgcacc     360
aaagttcacg gcagcatcct tcgccatagt ggnaan                                396
```

<210> SEQ ID NO 49
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 49

```
accccaaaat gggaaaggaa aagactcata tnaacattgn cgtnattgga cacgtacatt       60
cggncaagtn caccactact ggncatntga tntataaatg cggnggcatc gacanaanaa     120
ccatngnaan atttganaag gaggctgcta atatnggaaa gggctccntc nantntgcct     180
gggtcttgga tnaactgaaa nctgancntg aacgtggnnt caccattgat atctncttgt     240
ggaaatntna gaccancann tactatgtna ctatcattga tgcccaggga cacaganact     300
```
ttatcnaaan catgattacn nggacatnta nagctgactg tgctngcctg attgtngctg    360
ctggtgttgg tgaatttgaa nctggtatnt ccaana                              396

<210> SEQ ID NO 50
<211> LENGTH: 396
<212> TYPE: DNA
<213> ORGANISM: Homo sapien

<400> SEQUENCE: 50
cgacttcttg ctggtgggtg gggcagtttg gtttagtgtt atactttggt ctaagtattt     60
gagttaaact gctttttgc taatgagtgg gctggttgtt agcaggtttg ttttttcctgc   120 tgttgattgt tactagtggc attaactttt agaatttggg ctggtgagat taatttttt    180 taatatccca gctagagata tggcctttaa ctgacctaaa gaggtgtgtt gtgatttaat   240
tttttcccgt tccttttcct tcagtaaacc caacaatagt ctaaccttaa aaattgagtt   300
gatgtcctta taggtcacta cccctaaata aacctgaagc aggtgttttc tcttggacat   360
actaaaaaat acctaaaagg aagcttagat gggctg                              396

<210> SEQ ID NO 51
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 51 ttttttttt ttcagcgngg atttatttta tttcattttt tactctcaag anaagaana     60 gttactattg caggaacaga catttttta aaaagcgaaa ctcctgacac ccttaaaaca    120 gaaacattg ttattcacat aataatgngg ggctctgtct ctgccgacag gggctgggtt   180
cgggcattag ctgtgccgtc gacaatagcc ccattcaccc cattcataaa tgctgctgct   240
acaggaaggg aacagcggct ctcccanaga gggatccacc ctggaacacg agtcacctcc   300
aaagagctgc gactgtttga naatctgcca anaggaaaac cactcaatgg gacctggata   360
acccaggccc gggagtcata gcaggatgtg gtactt                              396

<210> SEQ ID NO 52
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 52
acctcgctaa gtgttcgcta cgcggggcta ccggatcggt cggaaatggc agaggtggag     60
gagacactga agcgactgca nagccagaag ggagtgcagg gaatcatcgt cgtgaacaca   120
gaaggcattc ccatcaagag caccatggac aaccccacca ccacccagta tgccagcctc   180
atgcacagnt tcatcctgaa ggcacggagc accgtgcgtg acatcgaccc ccagaacgat   240
ctcaccttcc ttcgaattcg ctccaagaaa atgaaatta tggttgcacc agataaagac   300
tatttcctga ttgtgattca gaatccaacc gaataagcca ctctcttggc tccctgtgtc   360
attccttaat ttaatgcccc ccaagaatgt taatgt                              396

-continued

<210> SEQ ID NO 53
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 53
tttttttttt tttttttttt tttttttttt tttttttttt tttttttttt tttttttttt        60
tttttttttt tttttttttt tttttttttt tttttttttt tttttttttt tttttttttt       120
tttttttttt tttttttttt tttttttttt tttttttttt tttttttttt tttttttttt       180
tttttttttt tttttttttt tttttttttt tttttttttt ttannttntt ttttnttttn       240
cctttntttt aattcanaaa aagaanaaga aaanataana nnnancnnan nnnnnnnatn       300
ntncttnata ntnnttnnnn nannggnnnn gcgagnnnnn nnnnnnnnnn nntctnnnnt       360
tnnnnnnctt gcnccccttn nnttngnnnn angcaa                                 396

<210> SEQ ID NO 54
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 54
ctcttggggc tgctgggact cgcgtcggtt ggcgactccc ggacgtaggt agtttgttgg        60
gccgggttct gaggccttgc ttctctttac ttttccactc taggccacga tgccgcagta       120
ccagacctgg gaggagttca gccgcgctgc cgagaagctt tacctcgctg acctatgaa       180 ggcacgtgtg gttctcaaat ataggcattc tgatgggaac ttgtgtgtta aagtaacaga       240
tgatttagtt tgtttggtgt ataaaacaga ccaagctcaa gatgtaaaga agattgagaa       300
attccacagt caactaatgc gacttatggt agccaaggaa gcccgcaatg ttaccatgga       360
aactgantga atggtttgaa atgaagactt tgtcgt                                 396

<210> SEQ ID NO 55
<211> LENGTH: 396
<212> TYPE: DNA
<213> ORGANISM: Homo sapien

<400> SEQUENCE: 55
cgacggtttg ccgccagaac acaggtgtcg tgaaaactac ccctaaaagc caaatggga        60 aaggaaaaga ctcatatcaa cattgtcgtc attggacacg tagattcggg caagtccacc       120
actactggcc atctgatcta taaatgcggt ggcatcgaca aaagaaccat tgaaaaattt       180
gagaaggagg ctgctgagat gggaaagggc tccttcaagt atgcctgggt cttggataaa       240
ctgaaagctg agcgtgaacg tggtatcacc attgatatct ccttgtggaa atttgagacc       300
agcaagtact atgtgactat cattgatgcc ccaggacaca gagactttat caaaaacatg       360
attacaggga catctcaggc tgactgtgct gtcctg                                 396

<210> SEQ ID NO 56
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 56

| | | | | | |
|---|---|---|---|---|---|
| tttttttttt | tttttctca | tttaactttt | ttaatgggtc | tcaaaattct | gtgacaaatt | 60 |
| tttggtcaag | ttgtttccat | taaaaagtac | tgattttaaa | aactaataac | ttaaaactgc | 120 |
| cacacgcaaa | aaanaaaacc | aaagnggtcc | acaaaacatt | ctcctttcct | tctgaaggtt | 180 |
| ttacgatgca | ttgttatcat | taaccagtct | tttactacta | aacttaaatg | gccaattgaa | 240 |
| acaaacagtt | ctganaccgt | tcttccacca | ctgattaana | gtggggtggc | aggtattagg | 300 |
| gataatattc | atttagcctt | ctgagctttc | tgggcanact | tggngacctt | gccagctcca | 360 |
| gcagccttnt | tgtccactgc | tttgatgaca | cccacc | | | 396 |

<210> SEQ ID NO 57
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 57

| | | | | | |
|---|---|---|---|---|---|
| cctttttttt | tttttttttt | tttttttttt | tttttttttt | tttttttttt | tnaaaanntt | 60 |
| nttttgcaa | anccnancaa | aaanggnngg | aangaaaaan | nggaaaaatt | nttttttncnt | 120 |
| ntttgggaac | nnnnagccct | tnntttgaaa | aaangnggnc | ttaaaanngn | tgaannaaag | 180 |
| gnnannnccn | gntncttnnn | tttaaaaana | angggnnngn | ttttttttaa | anaanatttt | 240 |
| tttttccct | aanancnncn | anntgaaacn | ngnccнacn | nctnncttna | aagggnnnaa | 300 |
| atnanangnn | aaaaaanccc | tnanccccc | ccttanntt | tncnannana | naaagncntt | 360 |
| ttgggncntg | naaaaanaan | ccttttttnnt | gcnttn | | | 396 |

<210> SEQ ID NO 58
<211> LENGTH: 396
<212> TYPE: DNA
<213> ORGANISM: Homo sapien

<400> SEQUENCE: 58

| | | | | | |
|---|---|---|---|---|---|
| cgacctcaaa | tatgccttat | tttgcacaaa | agactgccaa | ggacatgacc | agcagctggc | 60 |
| tacagcctcg | atttatattt | ctgtttgtgg | tgaactgatt | ttttttaaac | caaagtttag | 120 |
| aaagaggttt | ttgaaatgcc | tatggtttct | ttgaatggta | aacttgagca | tcttttcact | 180 |
| ttccagtagt | cagcaaagag | cagtttgaat | tttcttgtcg | cttcctatca | aaatattcag | 240 |
| agactcgagc | acagcaccca | gacttcatgc | gcccgtggaa | tgctcaccac | atgttggtcg | 300 |
| aagcggccga | ccactgactt | tgtgacttag | gcggctgtgt | tgcctatgta | gagaacacgc | 360 |
| ttcaccccca | ctccccgtac | agtgcgcaca | ggcttt | | | 396 |

<210> SEQ ID NO 59
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 59

```
cttttttttt tttttttttt tcagnggaaa ataacttttta ttganacccc accaactgca      60
aaatctgttc ctggcattaa gctccttctt cctttgcaat tcggtctttc ttcagnggtc     120
ccatgaatgc tttcttctcc tccatggtct ggaagcggcc atggccaaac ttggaggngg     180
tgtcaatgaa cttaaggnca atcttctcca nagcccgccg cttcntctgc accancaagg     240
acttgcggag ggngagcacc cgcttnttgg ttcccaccac ncagcctttc agcatgacaa     300
agtcattggt cacttcacca tagnggacaa agccacccaa agggttgatg ctccttggca     360
aataggncat agtcacngga ggcattgtnc ttgatc                               396
```

<210> SEQ ID NO 60
<211> LENGTH: 396
<212> TYPE: DNA
<213> ORGANISM: Homo sapien

<400> SEQUENCE: 60

```
acctcagctc tcggcgcacg gcccagcttc cttcaaaatg tctactgttc acgaaatcct      60
gtgcaagctc agcttggagg gtgatcactc tacaccccca agtgcatatg ggtctgtcaa     120
agcctatact aactttgatg ctgagcggga tgctttgaac attgaaacag ccatcaagac     180
caaaggtgtg gatgaggtca ccattgtcaa cattttgacc aaccgcagca atgcacagag     240
acaggatatt gccttcgcct accagagaag gaccaaaaag gaacttgcat cagcactgaa     300
gtcagcctta tctggccacc tggagacggt gattttgggc ctattgaaga cacctgctca     360
gtatgacgct tctgagctaa aagcttccat gaaggg                               396
```

<210> SEQ ID NO 61
<211> LENGTH: 396
<212> TYPE: DNA
<213> ORGANISM: Homo sapien

<400> SEQUENCE: 61

```
tagcttgtcg gggacggtaa ccgggacccg gtgtctgctc ctgtcgcctt cgcctcctaa      60
tccctagcca ctatgcgtga gtgcatctcc atccacgttg gccaggctgg tgtccagatt     120
ggcaatgcct gctgggagct ctactgcctg gaacacggca tccagcccga tggccagatg     180
ccaagtgaca agaccattgg gggaggagat gactccttca acaccttctt cagtgagacg     240
ggcgctggca agcacgtgcc ccgggctgtg tttgtagact tggaacccac agtcattgat     300
gaagttcgca ctggcaccta ccgccagctc ttccaccctg agcagctcat cacaggcaag     360
gaagatgctg ccaataacta tgcccgaggg cactac                               396
```

<210> SEQ ID NO 62
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 62

```
tcgacgtttc ctaaagaaaa ccactctttg atcatggctc tctctgccag aattgtgtgc      60
actctgtaac atcttttgtgg tagtcctgtt ttcctaataa ctttgttact gtgctgtgaa    120
agattacaga tttgaacatg tagtgtacgt gctgttgagt tgtgaactgg tgggccgtat     180
gtaacagctg accaacgtga agatactggt acttgatagc ctcttaagga aaatttgctt    240
```

```
ccaaatttta agctggaaag ncactggant aactttaaaa aagaattaca atacatggct    300
ttttagaatt tcnttacgta tgttaagatt tgngtacaaa ttgaantgtc tgtnctganc    360
ctcaaccaat aaaatctcag tttatgaaan aaannn                              396
```

<210> SEQ ID NO 63
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 63

```
ttnttttttt nttttntntt tntcnttgn ttgnacngaa cccggcgctn nttcccacn      60 nnnnacggcc gcccntattc annnntncnt canntannna ccgcaccctc ggactgcnnn   120
tngggccccg ccgncnannc nccnncnccc anttcnccgc cgccgccgcc gccttttttt   180
attggcnncc atnanaaccg gggncacctc ncangngcgc cnaaantngg ggcangactc   240 anaggggggcc atcaaccncc aagnncaanc tgganctcta caaacggcct acgntttntg  300
nccatgnggg tagggnttta cccgcnatga tgannatgnn aanaactttn ncaancccctt  360 tattaaccaa tgnggtgngg agacggaacn tggtta                             396
```

<210> SEQ ID NO 64
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 64

```
tcgacgtcgg ggtttcctgc ttcaacagtg cttggacgga acccggcgct cgttccccac    60
cccggccggc cgcccatagc cagccctccg tcacctcttc accgcaccct cggactgccc   120
caaggccccc gccgccgctc cagcgccgcg cagccaccgc cgccgccgcc gcctntnctt   180
agtcgccgcc atgacgaccg cgtccacctc gcaggtgcgc cagaactacc accaggactc   240
agaggccgcc atcaaccgcc agatcaacct ggagctctac gcctcctacg tttacctgtc   300
catgtcttac tactttgacc gcgatgatgt ggctttgaan aactttgcca aatactttct   360
tcccaatctc atgaggagaa ggaacatgct ganaaa                              396
```

<210> SEQ ID NO 65
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 65

```
tttttttttt tttttttttt tttttnacca ataatgcttt tatttccac atcaanatta     60 atttatatgt tagttttagt acaagtacta aaatgtatac ttnttgccct aatagctaag   120
gnatacataa gcttcaccat acatnttgca nccnnctgtc tgtcctatgt cattgttata   180
aatgtanana ttttaggaaa ctnttttatt caacctggga catntatact gtaggagtta   240
```

| | | | | |
|---|---|---|---|---|
| gcactgacct | gatgtnttat | ttaaaagtaa | tgnatattac | ctttacatat | attccttata | 300 |
| tattnaaacg | tatttccatg | ttatccagct | taaaatcaca | tggnggttaa | aagcatgagt | 360 |
| tctgagtcaa | atctggactg | aaatcctgat | gctccc | | | 396 |

<210> SEQ ID NO 66
<211> LENGTH: 396
<212> TYPE: DNA
<213> ORGANISM: Homo sapien

<400> SEQUENCE: 66

| | | | | | |
|---|---|---|---|---|---|
| tcgactttt | ttttccagg | acattgtcat | aatttttat | tatgtatcaa | attgtcttca | 60 |
| ataaagtta | caacttgatt | aaagttgata | gacatttgta | tctatttaaa | gacaaaaaaa | 120 |
| ttcttttatg | tacaatatct | tgtctagagt | ctagcaaata | tagtacctt | cattgcagga | 180 |
| tttctgctta | ataacaag | caaaacaaa | caactgaaaa | aatataaacc | aaagcaaacc | 240 |
| aaaccccccg | ctcaactaca | aatgtcaata | ttgaatgaag | cattaaaaga | caaacataaa | 300 |
| gtaacttcag | cttttatcta | gcaatgcaga | atgaatacta | aaattagtgg | caaaaaaaca | 360 |
| aacaacaaac | aacaaacaaa | acaaaacaaa | caaaca | | | 396 |

<210> SEQ ID NO 67
<211> LENGTH: 396
<212> TYPE: DNA
<213> ORGANISM: Homo sapien

<400> SEQUENCE: 67

| | | | | | |
|---|---|---|---|---|---|
| acgcttttgt | ccttcatttt | aactgttatg | tcatactgtt | atgttgacat | atttctttat | 60 |
| aagagaatag | aggcaaaagt | atagaactga | ggatcatttg | tatttttgag | ttggaaatta | 120 |
| tgaaacttca | ccatattatg | atcatacata | ttttgaagaa | cagactgacc | aaagctcacc | 180 |
| tgttttttgt | gttaggtgct | ttggctgaac | ttgattccag | ccccctttc | cctttggtgt | 240 |
| tgtgtatgtc | tcttcatttc | ctctcaaatc | ttcaactctt | gccccatgtc | tccttggcag | 300 |
| caggatgctg | gcatctgtgt | agtcctcata | ctgtttactg | ataacccaca | aattcatttt | 360 |
| catggcagac | ctaagctcag | accctgcctt | gtcctg | | | 396 |

<210> SEQ ID NO 68
<211> LENGTH: 396
<212> TYPE: DNA
<213> ORGANISM: Homo sapien

<400> SEQUENCE: 68

| | | | | | |
|---|---|---|---|---|---|
| acctgagtcc | tgtcctttct | ctctccccgg | acagcatgag | cttcaccact | cgctccacct | 60 |
| tctccaccaa | ctaccggtcc | ctgggctctg | tccaggcgcc | cagctacggc | gcccggccgg | 120 |
| tcagcagcgc | ggccagcgtc | tatgcaggcg | ctggggctc | tggttcccgg | atctccgtgt | 180 |
| cccgctccac | cagcttcagg | ggcggcatgg | ggtccggggg | cctggccacc | gggatagccg | 240 |
| ggggtctggc | aggaatggga | ggcatccaga | acgagaagga | gaccatgcaa | agcctgaacg | 300 |
| accgcctggc | ctcttacctg | gacagagtga | ggagcctgga | gaccgagaac | cggaggctgg | 360 |
| agagcaaaat | ccgggagcac | ttggagaaga | agggac | | | 396 |

<210> SEQ ID NO 69
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 69
ntcncngnng ntgtggtnnt tttttaatt tttatnttt cttttttttt ctngctagcn    60
cttncttttt ttggaattnc ggtnccttt tntntcnatt ttttngacaa aaanaacctn    120
ttntttnana ccanagnnng gnncacncnt nnaatntncc ccttttncgn tngggagctn    180
cncnttnnnc gccnacntca ntcgagacng tncttttnnn tnnancannn tnngtncgtt    240
gncngcnttn ntncannant nttccctatn nacntgnnnt cncncatnnt tggacnancn    300
cctagccttn ccatnntttn nttntttntn natnancctn gaaaacntcn gnntnttcnc    360
nncnttnccn cncncnccttt cntatgtncn atgncn    396

<210> SEQ ID NO 70
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 70
tttttttttt tttntttt tttttttt ttttttttntt tttttttttt tttttntnc    60 aannnntnaa cttttaanng gccnccngcn ccccaanggg gaccctgctt ttgnnggcta    120
aatgccnnaa aactttgggg nantnggtat naaacccncc tttgcccnnc annttncgg    180 gggggggggg tttttgnngg ggaacangna naacnttttn ncnanggnat caccaaaaan    240
aaagcccnnc ccttttccn annggggggg ggngggggga aantcanccc ccanattgac    300
cttnatttca aaangggct tataatcctg ggcntggann cttccctnta cccgggggtt    360
gnccacnttt tattanaggg gnangnggat ccccnt    396

<210> SEQ ID NO 71
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 71
gcatctagag ggccngttta ntctagaggn ccngnntaaa cnnnnncatc nacctncnnt    60
gcncctgctn gttgccnccc ntctgtgnct tgcnnnnccc nngagcgtnc cttnaccnnn    120
gaangtgcct nnnnnactga nnnnnncnna taanatgngg anantncgtc gncattntnt    180 natnggggt gatgctattc tgggggtgg ggnggngnna tnnnatactn nggggacgtn    240
nnatnangag nnatntcnng nttntctnnt gntttntggg gggcnatnng nnntctntnn    300
ggactcntcg cncannnatc aatancttna ttcngtgtan ngtccgnccn tagnncngcn    360
ngtactnnan ngttgnnntc attactnttc gtnngg    396

<210> SEQ ID NO 72
<211> LENGTH: 396
<212> TYPE: DNA
<213> ORGANISM: Homo sapien
<220> FEATURE:
<221> NAME/KEY: misc_feature
<222> LOCATION: (1)...(396)

<223> OTHER INFORMATION: n = A,T,C or G

<400> SEQUENCE: 72

| tnttttttt  tttctaaaac atnactnttt attnnnnang ntttntgaac ctctnngcnt | 60 |
| natggtgaga gtttgtctga ttaataanaa tnggannntt nannanangc ntgnncgcaa | 120 |
| ngatggcnnc nctgtatatc ccaccatccc attacactnt gaaccttttn tttgattaat | 180 |
| aaaaggaagg natgcgggga angggggaaag agaatgcttg aacattncca tgngnccttn | 240 |
| gacaaacttt ccaatggagg cnggaacnaa nnaccaccan ncaactcccc tttttgtaat | 300 |
| ttnnnaactt ncaacnncta nctntttatt ttggcntccc tggnngaaac agnctgtatn | 360 |
| annnnnaagn ccntgagaac atccctggnt nncnna | 396 |

<210> SEQ ID NO 73
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 73

| ntcaacntng actnctgtga ggnatggtgc tgggngcnta tgcngtgngn ttttggatac | 60 |
| naccttatgg acantngcnn tcccnnggaa ngatnataat ncttactgna gnnactnnaa | 120 |
| nnttccntnt cnaaaangtt naaaancatt ggatgtgcca caatgatgac agtttatttg | 180 |
| ctactcttga gtgctataat gatgaagatc ttanccacca ttatcttaac tgangcaccc | 240 |
| aanatggtga nttggggaac atatanagta cacctaagtt cacatgaagt tgtttnttcc | 300 |
| caggnnctaa agagcaagcc taactcaagc cattgncaca caggtgagac acctctatttt | 360 |
| tgtacttctc acttttaagg gattagaaaa tagcca | 396 |

<210> SEQ ID NO 74
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 74

| ccttttttt tttttttact gngaatatat acttttttatt tagtcatttt tgtttacaat | 60 |
| tgaaactctg ggaattcaaa attaacatcc ttgcccgtga gcttcttata gacaccanaa | 120 |
| aaagtttcaa ccttgtgttc cacattgttc tgctgtgctt tgtccaaatg aacctttatg | 180 |
| agccggctgc catctagttt gacgcggatt ctcttgccca caatttcgct tgggaagacc | 240 |
| aagtcctcaa ggatggcatc gtgcacagct gtcagagtac ggctcctggg acgcttttgc | 300 |
| ttatttttg tacggctttt tcgagttggc ttaggcagaa ttctcctctg agcgataaag | 360 |
| acgacatgct tcccactgaa cttttctccc aattcg | 396 |

<210> SEQ ID NO 75
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 75

```
ttttttttt tttnttttt ttttttttt tttttttnaa ntntaanggg ganggcccct      60
tttttttaaa ctngnccntt ttnctttcct tttttnaaaa ggaaaaaaaa annttntttt   120
ttcnttnaaa aacccttttt cccacnaaca aaaaaaaccn ttccccntnc cttttnnnna   180
aaaaaaaggg gctnggnntt tccccttann caaaaaaccn tntccnnggg naaaaaantt   240
ntcnccgggg gggaaacnnn tggggtgtn nccnaaattt ggggccntc ggaaggggg      300
nnccncncct aaagangtnt ttcaaaanaa aaaccccnt cctnttntaa aaanaaaana    360
aaanaangnn ngnntttttt ntcnttnncc ccccaa                            396
```

<210> SEQ ID NO 76
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 76

```
acattcttca gaaatacagt gatgaaaatt cattttgaaa ctcaaatatt ttcattttgg    60
atattctcct gttttatta aaccagngat tacncctggc cntccctnta aatgttctag   120
gaaggcatgt ctgttgtnnt ttnnnnaaaa nnaaattntt tttttttngn naaaccccaa  180
atcccanttt atcaggaagt tagncnaatg aaatggaaat tggntaatgg acaaaagcta  240
gcttgtaaaa aggaccaccc nnccacnngn ctttaccccc ttggttngtt ggggaaaaa   300
ccatnnttaa ccntntggnn aaaattgggn ncntaaagtt tncntggnna acagtncntn  360
cngtattnaa ttgncnttat nggaaaatcn gggatt                            396
```

<210> SEQ ID NO 77
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 77

```
ttttttttt ttttttttt ttttttttt tatcaacatt tatatgcttt attgaaagtt      60
ganaanggca acagttaaat ncngggacnc cttacaattg tgtaaanaac atgcncanaa  120
acatatgcat ataactacta tacaggngat ntgcaaaaac ccctactggg aaatccattt  180
cattagttan aactgagcat ttttcaaagt attcaaccag ctcaattgaa anacttcagt  240
gaacaaggat ttacttcagc gtattcagca gctanatttc aaattacnca aagngagtaa  300
ctgngccaaa ttcttaaaat ttntttaggg gnggttttg gcatgtacca gttttatgt   360
aaatctatnt ataaaagtcc acacctcctc anacag                            396
```

<210> SEQ ID NO 78
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 78

```
agctggcnaa aggngnatgn gctgcnangc gattangnnn ggtaacgtca nnggntnncc      60
agtgcangac nttgtaaaac gacggccaca tgaattgtaa tacgactcac tatngggcgn     120
attgggccgt gnaggatngt gntcacactc gaatgtatnc tggcngatnc ananngcttt     180
atngctnttg acggngnntn anccanctng ggctttaggg ggtatcccct cgccctgct     240
tcnttgattt gcacgggcnn ctccganttc cttcataata ccngacgctt cnatcccta     300
gctcngacct ntcantntnt tcnntgggtt ntnnccgntc acngcttncc cgnangntat   360
aatctnggct cctttnggga tccattantc tttact                              396
```

<210> SEQ ID NO 79
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 79

```
caccaaccaa aacctggcgc cgttggcatc gtagagtgaa cacaacccaa aaacgatacg      60
ccatctgttc tgccctggct gcctcagccc taccagcact ggtcatgtct aaaggncatc    120
gtattgagga agttcctgaa cttcctttgg tangttgaag ataaagctga aggctacaag    180
aagaccaang aagntgtttt gctccttaan aaacttanac gcctggaatg atatcaaaaa    240
ngctatgcct ctcagcgaat gagactggan angcaaaatg agaaaccntc nccgcatcca    300
gcgnaggggc cgtgcatctc tatnntgang atnntggnan cnttcaaggc cttcagaacc    360
tccctngaaa tnctctnctt taangaacca aactgn                              396
```

<210> SEQ ID NO 80
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 80

```
tgtacatagg catcttattc actgcaccct gtcacaccca gcaccccccg ccccgcacat      60
tatttgaaag actgggaatt taatggttag ggacagtaaa tctacttctt tttccaggga    120
cgactgtccc ctctaaagtt aaagtcaata caagaaaact gtctattttt agcctaaagt   180
aaaggctgtg aagaaaattc attttacatt gggtagacag taaaaaacaa gtaaaataac   240
ttgacatgag cacctttaga tccttccctt catgggcttt tgggcccaga atgacctttg    300
aggcctgtaa anggattgna atttcctata agctgtatag tggagggatt ggngggtcat   360
ttgagtaagc cctccaagat acnttcaata cctggg                              396
```

<210> SEQ ID NO 81
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 81

```
gcagctgaag ttcagcaggt gctgaatcga ttctcctcgg cccctctcat tccacttcca      60
acccctccca ttattccagt actacctcag caatttgtgc ccctacaaa tgttagagac      120 tgtatacgcc ttcgaggtct tccctatgca gccacaattg aggacatcct gcatttcctg    180
ggggagttcg ccacagatat tcgtactcat ggggttcaca tggttttgaa tcaccagggn    240
ccgccatcag gagatgcctt tatccagatg aagtctgcgg acagancatt tatggctgca    300
cagaagtggc ataaaaaaaa catgaaggac agatatgttg aagttttcag tgtcagctga    360
nganagaaca ttgnnngtann nggggnact ttaaat                              396
```

<210> SEQ ID NO 82
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 82

```
gactcagaaa tgtcagtctc atgaagttca aaagatcgag aatgtttgct atcttggtgg    60
agcagccgca gccaagcaag taacttgtaa atgaggaat gccatcaccc ctcgagtgtc    120
catcccacat aacttggggt tagagcacaa gcgttcccag gaactactca ccttaccatc    180
ttggccgttt catttgcttc caccagttct ggaaagagan ggcctagaag ttcaaaaaaa    240
aagtaggaaa ngtgcttttg gagaaaatca cctgctcctc agaactgggc ttacaanctg    300
ngaagtacnc tatgtgccac ctaatcctca tatatgacct caagagacnc caataagcat    360
atttccacca cggaatgacc agtgctttgg gtaana                              396
```

<210> SEQ ID NO 83
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 83

```
tttgatttaa ganatttatt attttttttaa aaaaagcaac ttccagggtt gtcattgtac    60
aggttttgcc cagtctccta tagcatggta tagtgataac tgattttta taacaatgac    120 tcagaggcat tgaagatcca taactatctt ctgaattatc acagaaagaa gaaagttaga    180
agagtttaat gttaagtgta ttaaaaatca tattctaatt cttttaattt ggttatctga    240
gtatgataat ataggagagc tcagataaca aggaaaaggc attggggtaa gaacactcct    300
tcccacagga tggcattaac agacttttc tgcatatgct ttatatagtt gccaactaat    360 tcaccttta cncagcttna tttttttttta ctnggg                              396
```

<210> SEQ ID NO 84
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 84

```
tttttacagc aatttttttt tattgatgtt taacctgtat acaaccatac ccatttaag     60 ngtacagaca aatgaatttt gacaaattca ttcactcatc taatcatcac tataaccatg   120
atacagattt ttatcactcc aaaagtccat cctgtgctct tttcaagtcc atcctcctca   180 tctgatacccc caagccacca ttgttttgct ttctggaact acagttttgg gnttttagaa  240
tttcatatat ggtngaatca taccatttgn natttgggc tgacgnctttt cctccaataa   300 tggatttgag aattatctac attttgcatg gatcctgggt tatttatacc aacnangggt   360
tattatgnaa aatnggacca caatttggng gcanta                            396
```

<210> SEQ ID NO 85
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 85

```
cagtgaccgt gctcctaccc agctctgctc cacagcgccc acctgtctcc gccctcggc    60 ccctcgcccg gctttgccta accgccacga tgatgttctc gggcttcaac gcagactacg  120
aggcgtcatc ctcccgctgc agcagcgcgt ccccggccgg ggatagcctc tcttactacc  180
actcacccgc agactccttc tccagcatgg gctcgcctgc aacgcgcagg acttctgcac  240
ggacctggcc gctccagtgc caacttcatt ccacggcact gcatctcgac canccggact  300
tgcannggtt ggggaanccg cccttgtttc tccgtggccc atctaanacc aaaccntca   360 cctttttcgga gncccncccc ctccgntggg nttact                           396
```

<210> SEQ ID NO 86
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 86

```
ttttnnactg aatgtttaat acatttgnag gaacagaaga aatgcagtan ggattaanat   60
tttataatta gacattaatg taacagatgn ttcatttttc aaagaagntn ccccttntc   120 cctatctttt tttaatcttc cttanagcaa taantagtaa ttactatatt tgtggacaag  180
ctgctccact gtgntggaca gtaattatta aatctttatg tttcacatca ttattaccttt 240 ccanaattct accttcattt ccctgcacag gttcactgga ctggntcaca ancaaattgn  300
actccactca antanaagag cccaaagaaa ttagagtaac gncnantcct atgaattana  360
gacccaaaga tttnaggngn tgattagaaa cataan                            396
```

<210> SEQ ID NO 87
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 87

```
atggaggcgc tggggaagct gaagcagttc gatgcctacc ccaagacttt ggaggacttc   60
```

```
cgggtcaaga cctgcggggg cgccaccgtg accattgtca gtggccttct catgctgcta    120
ctgttcctgt ccgagctgca gtattacctc accacggagg tgcatcctga gctctacgtg    180
gacaagtcgc ggggagataa actgaagatc aacatcgatg tacttttcc ncacatgcct    240 tgtgcctatc tgagtattga tgccatggat gtggccngag aacancagct ggatgnggaa    300
cacaacctgt ttaagccacc actagataaa gatgcatccc ngtgagctca nagctgagcg    360
gcatgagctt gngaaantcn aggtgaccgg gtttga                              396
```

<210> SEQ ID NO 88
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 88

```
tccagagcag agtcagccag catgaccgag cgccgcgtcc ccttctcgct cctgcgggc    60 cccagctggg accccttccg cgactggtac ccgcatagcc gctcttcgac caggccttcg   120
ggctgccccg gctgccggag gagtggtcgc agtggttagg cggcagcagc tggccaggct   180
acgtgcgccc cctgccccc gccgcatcga gagccccgca gtggccgcgc ccgctacagc    240
cgcgcngctc agccggcaac tcacancggg gctcggagat ccgggacact gcggaccgct   300
ngcgcgtgcc ctggatgtca ccactttngc ccggacaact gacggtnana caaggatggg   360
gggtgganan nccngtaanc caagaanggg naggac                              396
```

<210> SEQ ID NO 89
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 89

```
gagagaacag taaacatcca gccttagcat ctctcangag tactgcagat cttcattagc    60
tatattcaca tggagnaatg ctattcaacc tatttctctt atcaaaacta attttgtatt   120
ctttgaccaa tgttcctaaa ttcactctgc ttctctatct caatcttttt ccctttctc   180 atctttcctc cttttttcag tttctaactt tcactggttc tttggaatgn ttttcttttc   240
atctcttttc ttttacattt tggggtgtcc cctctctttt cttaccctct ttctncatcc   300
ttcttnttct tttgaattgg ctgcccttta tcntctcatc tgctgncatc ttcatttctc   360
ctccctcctn tttccnntca ttctactctc tcccnt                              396
```

<210> SEQ ID NO 90
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 90

```
gggcgccggc gcgccccccc accccgccc cacgtctcgt cgcgcgcgcg tccgctgggg    60
```

```
gcggggagcg gtcgggccgg cngcggtcgg ccggcggcag ggtggtgcgn tttcnttttn        120
nattnnccnc nttcttcttn nttnnncnnn ctnntanncn ntnncnttcn cnnnntttnc        180
tntntcttna ccnnntttn taatcntctt ctncntnnnn tctcttnnat ntnttncttta       240 nttcctnnnn tttnttctnt cntttctcnc ctnnntctcn nnctcnncnc tcnncatttt        300
nntnttttnt nccttctnnt cttnnttctn ntnntnnttt nnnnttctnt tnntcatntt        360
ncctntntta ctntcancttt ntatnnncct cntttt                                 396

<210> SEQ ID NO 91
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 91
ntntcctnna tttttnnntc nncttttttt tnnaattttt ctttnttttn tttataaaaa        60
tcnncacnta aaacngcgga anaggggatt tnttnttngg gngtancncn nggcncaaa         120 naacccaaa aatancccaa aatgcacagg nccngggnaa angaccnacn tgggtntttt         180
ntttntnaac aagggggggtt ttaaagggna tnggnatcaa agggnataaa ntttaaacct      240
ttganaaatt ttttaanagg cttgcccccc actttggncc ccnccccncn gnngggatcc       300 aattttttt cnttggggct cccngncccn nannttccgg gttnntggnc nntcctnntt       360 ttttttttt tgccttcacc cntnccattn cntttt                                  396

<210> SEQ ID NO 92
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 92
ctntttnnnt nttttttcc ccatcatcca naaatgggtt ttattctcag ccgagggaca       60
gcaggactgg taaaaactgt caggccacac ggttgcctgc acagcacccc catgcttggt     120
aggggtgggg agggatggcg ggggctggnt gnccacaggc cgggcatgac aaggaggctc     180
actggaggtg gcacactttg gagtgggatg tcggggggaca ncttctttgg tanttgggcc    240
acaagattcc caaggatanc acnnnnnactg attnccannc tanagncaag cggntggcca   300
tntgtangnn nttntntatn tgactattta tagattttta tanaacaggg naagggcata    360
ccncaaaagg gnccaantt ttaccnccgg gcnccc                                  396

<210> SEQ ID NO 93
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 93
gctgccacag atctgttcct tgtccgtttt ttgggatcca caggccctat gtatttgaag     60
ggaaatgtgt atggctcaga tccttttttga aacatatcat acaggttgca gtcctgaccc   120
```

```
aagaacagtt ttaatggacc actatgagcc cagttacata aagaaaaagg agtgctaccc      180
atgttctcat ccttcagaag aatcctgcga acggagcttc agtaatatat cgtggcttca      240
catgtgagga agctacttaa cactagttac tctcacaatg aaggacctgn aatgaaaaat      300
ctgnttctaa ccnagtcctn tttanatttt agngcanatc cagaccancg ncggtgctcg      360
agtaattctt tcatgggacc tttggaaaac tttcag                                396
```

<210> SEQ ID NO 94
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 94

```
tgccttaacc agtctctcaa gtgatgagac agtgaagtaa aattgagtgc actaaacgaa       60
taagattctg aggaagtctt atcttctgca gtgagtatgg cccaatgctt tctgnggcta      120
aacagatgta atgggaagaa ataaaagcct acgtgttggt aaatccaaca gcaagggaga      180
tttttgaatc ataataactc atanngtgct atctgtcagt gatgccctca gagctcttgc      240
tgntagctgg cagctgacgc ttctangata gttagnttgg aaatggtctt cataataact      300
acacaaggaa agtcanccnc cgggcttatg aggaattgga cttaataaat ttagngngct      360
tccnacctaa aatatatctt ttggaagtaa aattta                                396
```

<210> SEQ ID NO 95
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 95

```
cctcccaccc ncttanttca tgagattcga naatgncact tntgtgctnt ttnctnnttn       60
tattctnacn atttctttct tggngcggna nnaatcccnt ttttnnggc gnctctcccn       120 ncttntnntt tcntggngct ntccttttc nnnnnaaact tntacnnngt ttanaantnt       180
ttctgnangg gggnntccna ananttttt ccncctncct nattccnctc tnaannctcn       240
cnaattgttt ccccccccn ntagnntatt ttttctaaaa aattaactcc nacgganaaa       300 atttttcccta aaatttcncc tccanatttn gaaaaaacnc gcccgganct nntntncgaa      360
tntnaatttt tnaaaaaaan ttattttcat cnggnn                                396
```

<210> SEQ ID NO 96
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 96

```
cctgggtacc aaatttcttt atttgaagga atggtacaaa tcaaagaact taagtggatg       60
ttttggacaa cttatagaaa aggtaaagga aaccccaaca tgcatgcact gccttggcga      120
```

| | |
|---|---|
| ccagggaagt cacccacgg ctatgggaa attagcccga ngcttaactt tcattatcac | 180 |
| tgcttccaag ggngtgcttg gcaaaaaaat attccgccaa ccaaatcggg cgctccatct | 240 |
| tgcccagttg gtnccgggnc cccaattctt ggatgctttc ncctcttntt ccggaatgng | 300 |
| ctcatgaant ccccaanng gggcattttg ccagnggccn tttngccatt cnagnnggcc | 360 |
| tgatccattt tttccaatgt aatgccnctt cattgn | 396 |

<210> SEQ ID NO 97
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 97

| | |
|---|---|
| ctcaccctcc tcntnnttnt canaatattg ngaacttnnt nctgntcgaa tcactggcat | 60 |
| taaagganca ctagctaatg gcactaaatt tacnnactan ggaaactttt ttataatant | 120 |
| gcaaaaacat ntnaaaaaga ntgnagttcg cccatttctg cttnggaaga nctcttcact | 180 |
| tntaancccn natgnngncc tttgggtcaa aanctccgcg attattacng ngttnccnc | 240 |
| tatttgncct tcctttntcc ccaangccnc anatttcnna acttttnccnt naaatgcctt | 300 |
| tatttnatnn cntttcnacn ncttaanntt cccttttnaan aangatccct ncttcaaatn | 360 |
| ntttcccngt tcctngcatt ncccnnnnat ttctct | 396 |

<210> SEQ ID NO 98
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 98

| | |
|---|---|
| acagggacaa tgaagccttt gaagtgccag tctatgaaga ggccgtggtg ggactagaat | 60 |
| cccagtgccg ccccaagag ttggaccaac cacccctac agcactgttg tgatacccc | 120 |
| agcacctgan gaggaacaac ctaccatcca gaggggccag gaaaagccaa actggaacag | 180 |
| aggcgaatgg ctcagagggg tncatggcca agaaggaagc cctggaagaa cttcaatcac | 240 |
| cttcggtttc gggaccaccg gcttgtgtcc ctgttctgac tgcanaactt ggcgcngtnc | 300 |
| cccattanaa cctntgactc nncccttgct ataagnctgt tttggcccct gatgatgata | 360 |
| gggtttttat gangacactt gggcaccccc ttaatg | 396 |

<210> SEQ ID NO 99
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 99

| | |
|---|---|
| nttnttttc cgncnaaagg gcaagngttt ncatctttcc tgnccncnca ananngggtn | 60 |
| tntgtgcntt tnttttttcc caaaacccgg gtngggggaca ccttttgagg anccactnnt | 120 |
| cntccggggc nnnnttttag aaggngncta anaagcntct tgnnggggga aaacatcttt | 180 |

```
tttgcncccn acatacccce aagggggggg ggtgtctggg agganactaa ngactttnt      240 tttttnnccn caaanaactg anggccccca ttgctccccc cccantcttt aaaaaacccc     300
ttcaatttcc ttgncnggna aaaanggttg gnaaaaaang agngngcntc nnttncnttt     360
natggaaggn aaaaggtttt tggttgnaaa accccg                              396
```

<210> SEQ ID NO 100
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 100

```
ctaacacggt gaaaccctgt ctctactaaa aatacaaaaa aattagccag gcgtggtggc     60
gggcacctgt agtcccagct gctcaggaag ctgaggcagg agaatggcgt gaacccagaa    120
ggcggagctt gcagtgagct gagatcgtgt cagtgcactc cagcctgggc gacagagcga    180
gactcccgct caaaaaaaaa aaaaaaaaga gaaagaaaa agctgcagng agctgggaat     240
gggccctatc ccctccttgg ggatcaatga dcccctttt caaaanaaaa aaaaaataa      300 tgngattttg gnaacatatg gcactggtgc ttcnnggaat tctgttnntn ggcatgncccc   360 cctntgactg nggaaaaatc cagcaggagg cccana                              396
```

<210> SEQ ID NO 101
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 101

```
agttataact caacagttca tttatatgct gttcatttaa cagttcattt aaacagttca     60
ttataactgt ttaaaaatat atatgcttat agncaaaann tgttgtggcg nagttgttgc    120
cgcttatagc tgagcattat ttcttaaatt cttgaatgtt cttttggngg gntnctaaaa    180
ccgtatatga tccatttna tgggaaacng aattcntnnc attatcncac cttggaaata    240
cnnaacgtgg gggaaaaaaa tcattcccnc cntccaaaac tatacttctt ttatctngan   300
nttcttgntc ctgcncnggt ttngaatata nctgggcaaa nggntttncc aaatccntnt   360
acnntncttt gggaantanc ggcaantcnt cncttt                              396
```

<210> SEQ ID NO 102
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 102

```
actatacata agaacangct cacatgggag gctggaggtg ggtacccagc tgctgtggaa     60
cgggtatgga caggtcataa acctagagtc agngtcctgt tggcctagcc catttcagca   120
ccctgccact tggagnggac ccctctactc ttcttagcgc ctaccctcat acctatctcc   180
```

```
ctnctcccat ctcctacgga ctggcgccaa atggctttcc tgccaatttt gggatcttct      240
ctggctctcc agcctgctta ctcctctatt tttaaagggc caaacaaatc ccttctcttt      300
ctcaaacaca gtaatgnggc actgacccta ccacacctca tgaaggggc ttgttgcttt       360 tatttgggcc cgatctgggg gggcaaaat attttg                                 396
```

<210> SEQ ID NO 103
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 103

```
ttgtgttggg actgctgata ggaagatgtc ttcaggaaat gctaaaattg ggcaccctgc      60
cccaacttca aagccacagc tggtatgcca natggtcagg ttaaagatat caacctgctg     120
actacaaagg aaaatatggt ggggtcttct tttaccctct tgacttccct ttgngngccc     180
cccgaganca ttgctttccg ngatagggca aaanaaatta aaaaacttaa ctggccagtg     240
aatgggcttt ctgnggatct ccttctggca ttacatnggc aatccctaaa aaacaagang     300
actgggaccc ataacattct tttgnatcaa ccgaagcccc cattgttang atatngggct     360
taaangctga tnaagcatct cgtccgggcn ttttat                              396
```

<210> SEQ ID NO 104
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 104

```
aagggagggc gcgccaagac cttcccactc gngcacactg ggggcgccga cangacgcaa      60
cccagtccaa cttggatacc cttggnttta gttctcggac acttcttttta tctctccgtc    120 gcaacttgtc aagttctcaa nactgtctct ctgngntatc ttttttcttc gctgctcttc    180 nnccccgac gtatttntca aaangtctgc aattgttgna tacntnganc tncaccactg     240
ttacnaggtc atnaatttcn cntcaactct ntnccncttg ttccctgata tntcggccgg    300
ngncnccaat tctgtatttt nctcntcaac gntctcactt ttncctcctc cnggccactt    360
tctccccttc cttattccgg cnttgtttgc cnccat                              396
```

<210> SEQ ID NO 105
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 105

```
tcaatagcca gccagtgttc atttttatcc ttgagctttt agtaaaaact tcctggnttt      60 attttagtc attgggtcat acagcactaa agtctgctat ttatggaaac taactttttt     120
gtttttaatc caggccaaca tgtatgtaaa ttaaatttt agataattga ttatctcttt     180
gtactacttg agatttgatt atgagatgtg catattgctt tgggaagagc tcgaggaagg    240
```

-continued

| | |
|---|---|
| aaataattct ctcctttggt ttgaacctca actagataaa ccctaggaat tgttaactgc | 300 |
| acaagnattt tcattccaca aaacctgagg cagctctttt gccagagcgt tcctgnaccc | 360 |
| ccccacccca cttgccttgg gtctttanaa ngagcc | 396 |

<210> SEQ ID NO 106
<211> LENGTH: 396
<212> TYPE: DNA
<213> ORGANISM: Homo sapien

<400> SEQUENCE: 106

| | |
|---|---|
| gctgtgtagc acactgagtg acgcaatcaa tgtttactcg aacagaatgc atttcttcac | 60 |
| tccgaagcca aatgacaaat aaagtccaaa ggcatttct cctgtgctga ccaaccaaat | 120 |
| aatatgtata gacacacaca catatgcaca cacacacaca cacccaca gagagagagc | 180 |
| tgcaagagca tggaattcat gtgtttaaag ataatccttt ccatgtgaag tttaaaatta | 240 |
| ctatatattt gctgatggct agattgagag aataaaagac agtaaccttt ctcttcaaag | 300 |
| ataaaatgaa aagcaattgc tcttttcttc ctaaaaaatg caaagattt acattgctgc | 360 |
| caaatcattt caactgaaaa gaacagtatt gctttg | 396 |

<210> SEQ ID NO 107
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 107

| | |
|---|---|
| ttcacagaac anggtggttt attatttcaa tagcaaagag ctgaaaaatg tcgggtccca | 60 |
| taaggagca gaacctgacc cagagcctgc agtacatttc caccccacag ggtgcaggc | 120 |
| tgggccaggc agggccaaag gcagcagaaa tgggagtaag agactgtgcc cactgagaag | 180 |
| ctctgctggg tgtgggcagg tggcatgan atgatgatga tgtagtgtaa ggaccaggta | 240 |
| ggcaaaacct gtcaggnttg ntgaatgtca nagtggatcc aaaaggctga gggggtcgtc | 300 |
| anaaggccgg nggncccncc cttgcccgta tgggccttca aaaagtatgc ttgctcatcc | 360 |
| gttgttttncc ccanggagct gccanggana aggctn | 396 |

<210> SEQ ID NO 108
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 108

| | |
|---|---|
| gcctgctttt gatgatgtct acagaaaatg ctggctgagc tgaacacatt tgcccaattc | 60 |
| caggtgtgca cagaaaaccg agaatattca aaattccaaa ttttttttctt aggagcaaga | 120 |
| agaaaatgtg gccctaaagg gggttagttg aggggtaggg ggtagtgagg atcttgattt | 180 |
| ggatctcttt ttatttaaat gtgaatttca acttttgaca atcaaagaaa agacttttgt | 240 |
| tgaaatagct ttactgcttc tcacgtgttt tggagaaaan natcancct gcaatcactt | 300 |
| tttgnaactg ncnttgattt tcngcnncca agctatatcn aatatcgtct gngtanaaaa | 360 |

```
tgncctggnc ttttgaanga atacatgngt gntgct                              396
```

<210> SEQ ID NO 109
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 109

```
ggccgtaggc agccatggcg cccagcccgg aatggcatgg tcttgaagcc ccacttccac    60
aaggactggc agcggcgcgt ggccacgtgg ttcaaccagc cggcccggaa gatccgcaga   120
cgtaaggccc ggcaagccaa ggcgcgccgc atcgctccgc gccccgcgtc gggtcccatc   180
cggcccatcg tgcgctgccc acggttcggt accacacgaa gggcgcgccg gcgcggnttc   240
agcctggagg agctcagggt ggccggattt acaagaagng gccngacatc ngtattcttg   300
ggatncnnga agnggaacaa gtcacngagt ccttgcagcc acntcagcgg ntgatgacac   360
cgttcnaact catctnttcc caagaaacct cngnnc                             396
```

<210> SEQ ID NO 110
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 110

```
nntgggctcc tnncantnat aataaaccng actcatacnc cacaaggaga tgaacaggan    60
tatgtncatn ctgacgcgga aacagngcan ggagctgagg aggngccaag atgagaccta   120
nnggccnngg tgggcgcatt cccggnggag ggggccacta aggantacga nnntcnagcg   180
gctcttgnng gcngncctcc tcacncctgn ntattcgatt gtcncnnatg ncntcctatn   240
atnntcanna ttctntnntn atctcntnta cnncntcncn ttcatgntta cngntccctc   300
tcnttctnac cnttntctgn anctccttc tnnnncttc atctntnttc ngctttcttt    360
ctnnaatcnt nntttaacnt nntctncttt ntnatt                             396
```

<210> SEQ ID NO 111
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 111

```
taangancat nctggnttnt gcctnnccgn ctnattgant gttaaaggca attntgtggn    60
tgtcccagng aatgncggct nattttctt ccacattgng cncattcact cctcccactc   120
ttggcatgtn ngacataag canggtacat aatngnaaaa atctgnattt ctgatgccan   180
angggtanan cntnttgnat ntcattccat tgatatacag ccactntttt atttttgatc   240
ancggccttc ggntcactgc ncanggtact tgacctcagt gtcactatta tgggntttgg   300
tttcnctctt ttncnggccn ttntttttcn cacnttncan cttncttnnt nnaaaannna   360
nncactctct cttgctctct ngatacnnng tctnaa                             396
```

<210> SEQ ID NO 112
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 112

| | | | | |
|---|---|---|---|---|
| tcaacgtcac caattactgc catttagccc acgagctgcg tctcagctgc atggagagga | | | | 60 |
| aaaaggtcca gattcgaagc atggatccct ccgccttggc aagcgaccga tttaacctca | | | | 120 |
| tactggcaga taccaacagt gaccggctct tcacagtgaa cgatgttaaa gntggaggct | | | | 180 |
| ccaagnatgg tatcatcaac ctgcaaagtc tgaagacccc tacgctcaag gtgttcatgc | | | | 240 |
| acgaaaacct ctacttcacc aaccggaagg tgaattcggg gggctgggcc tcgctgaatc | | | | 300 |
| acttggattc cacattctgc tatgcctcat gggactcgca gaacttcagg ctggccaccc | | | | 360 |
| tgctcccacc atcactgntn gncaatantc acccag | | | | 396 |

<210> SEQ ID NO 113
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 113

| | | | | |
|---|---|---|---|---|
| nnnnttnnnn nggagcctta atttcagagt tttattgtat tgcactaaag gaacagcagg | | | | 60 |
| atggntatac aattttctct cattcagttt tgaaaatctg tagtacctgc aaattcttaa | | | | 120 |
| gaatacctttt accaccagat tagaacagta agcataataa ccaatttctt aataagtaat | | | | 180 |
| gtcttacaaa taaaaacaca tttaaaatag ctttaaatgc attcttcaca agtaattcag | | | | 240 |
| catatatttt atatcatggt tacttatgct tangaattnn agcaggatnt ttattctttt | | | | 300 |
| gatggaaata tgggaaaact ntattcatgc atatacangg ataatattca gcgaagggaa | | | | 360 |
| aatcccgttt ttattttggn aatgattcat atataa | | | | 396 |

<210> SEQ ID NO 114
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 114

| | | | | |
|---|---|---|---|---|
| aaatgggaca acgtgattct tttgttttaa ataaatactn agaacacgga cttggctcct | | | | 60 |
| acaagcattt ggactctaag gnttagaact ggagagtctt acccatgggc cccncncagg | | | | 120 |
| gacgccacgg ttccctccca ccccgngatc aagacacgga atcgntggc gatngttgga | | | | 180 |
| tcgcnatgtg cccctatct atagccttcc cnggncatnt acangcagga tgcggntggg | | | | 240 |
| anaactacaa ctgnaatntc tcnaacggtn atggtcccca ccgataaaga ttctacctng | | | | 300 |
| tcttttcntc ccctggagtg tgagtgnnng aggaagaagc ccttnccttca catcacctttt | | | | 360 |
| tgnacttctg aacaaganca anacnatggc ccccccc | | | | 396 |

<210> SEQ ID NO 115
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 115

```
ccgcctggtt cggcccgcct gcctccactc ctgcctctac catgtccatc agggtgaccc      60
agaagtccta caaggtgtcc acctctggcc cccgggcctt cagcagccgc tcctacacga     120
gtgggcccgg ttcccgcatc agctcctcga gcttctcccg agtgggcagc agcaactttc     180
gcggtggcct ggcggcggct atggtggggc cagcggcatg ggaggcatca cccgcagtta     240
cggcaaccag agcctgctga gcccttgcc tggaggngga ccccaacatc aagccgngcg     300
cacccaggaa aaggagcaga ncaagaccct caacaacaag nttgcttctt catagacaag     360
ggaccggtcc ttgaacagca naacaagatg ntggag                               396
```

<210> SEQ ID NO 116
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 116

```
atctcagttt actagctaag tgactttggg caagggattt aacctctcgt ccctcagttt      60
cctcctatgt aaaatgacaa ggataatagt accaacccaa tgtagattaa atgagtttac     120
gaagtgttag aatagtgctt ggcacattag tgctttacaa ctgctatttt gattgttgtt     180
gtgggctctc tcaaatgcat tgtctctaga tgccagtgac ccaggtcaaa atttaccttt     240
aaccaagctg catgtttccc agactgntgc acagtcctct accctgagan aaagcttcca     300
cccaaggata ctttttacttt ctgctggaaa actgatgagc aanggcaaca ngggacactt     360
atcgccaact ggaaangaga aattcttcct tttgct                                396
```

<210> SEQ ID NO 117
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 117

```
aaacattttt taataaaatt cctatagaaa gctcagtcat agggcaaata ctcagttctc      60
tttcccatat caccgaggat tgagagctcc caatattctt tggagaataa gcagtagttt     120
tgctggatgt tgccaggact cagagagatc acccatttac acattcaaac cagtagttcc     180
tattgcacat attaacatta cttgccccta gcacccctaaa tatatggnac ctcaacaaat     240
aacttaaaga tttccgtggg gcgcganacc atttcaattt gaactaatat ccttgaaaaa     300
aatcacatta ttacaagntt taataaatac nggaagaaga gctggcattt ttctaanatc     360
tgaattcnga cttggntttta ttccataaat acggtt                              396
```

```
<210> SEQ ID NO 118
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 118
accnncacct gntnnntttt aacnattaca acttctttat atggcagttt ttactgggng      60
cctaacactc tctttactgn ctcaagngga agtccaaaca aatttcattt ttgtagtaaa     120
aaatctttat ttccaaaatg atttgttagc caaaagaact ataaaccacc taacaagact    180
ttggaagaaa gagacttgat gcttcttata aattccccat tgcanacaaa aaataacaat    240
ccaacaagag catggtaccc attcttacca ttaacctggn tttaannctc caaancnnga    300
tttaaaaatg accccactgg gcccaatcca acatganacc taggggggnt tgccttgatt    360
angaatcccc cttanggact ttatctnggc tganaa                              396

<210> SEQ ID NO 119
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 119
atggccagct cactttaaat accacctcaa gactcatcga aatgaccgct ccttcatctg      60
tcctgcagaa ggttgtggga aaagcttcta tgtgctgcag aggctgaagg tgcacatgag    120
gacccacaat ggagagaagc cctttatgtg ccatgagtct ggctgtggta agcagtttac    180
tacagctgga aacctgaaga accaccggcg catccacaca ggagagaaac ctttcctttg    240
tgaagcccaa ngatgtggcc gtcctttgct gagtattcta ncttcgaaaa catctggngg    300
ntactcanga gagaaagcct cattantgcc antctgnggg aaaaccttct ntcagagngg    360
angcaggaat gtgcatatta aaaagctncc ttgnac                              396

<210> SEQ ID NO 120
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 120
catgggtcag tcggtcctga gagttcgaag agggcacatt cccaaagaca ttcccagtca      60
tgaaatgtag aagactggaa aattaagaca ttatgtaaag gtagatatgg cttttagagt    120
tacattatgc ttggcatgaa taaggtgcca ggaaaacagt ttaaaattat acatcagcat    180
acagactgct gttagaaggt atgggatcat attaagataa tctgcagctc tactacgcat    240
ttattgttaa ttgagttaca nangncattc anactgagt ttatagancc atattgctct    300
atctctgngn agaacatttg attccattgn gaagaatgca gtttaaaata tctgaatgcc    360
atctagatgt attgtaccna aaggggaaaa ataaca                              396

<210> SEQ ID NO 121
```

<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 121

```
tttttttttt ttttttttaa aatcaagtta tgtttaataa acattaataa atgtttactt      60
aaaagggtta ataaacnttt actacatggc aaattatttt agctagaatg cttttggctt     120
caagncatan aaaccagatt cnaatgccct taaanaattt tnaaanatcc attgangggg     180
ataactgtaa tccccaaggg gaanagggtt gggtatgaca ggtacanggg gccagcccag     240
tnntnncana nncagactct taccntcttt ctgctgtgnc accctcaggc attggctcca     300
ttctcngggn tgcncatggg aagatggctt tggacntaac nacacccttt tgtncacgta     360
aaggccngat gcagggtcaa anagnttccn ccatnt                              396
```

<210> SEQ ID NO 122
<211> LENGTH: 396
<212> TYPE: DNA
<213> ORGANISM: Homo sapien

<400> SEQUENCE: 122

```
gtcgacatgg ctgccctctg ggctcccaga acccacaaca tgaaagaaat ggtgctaccc      60
agctcaagcc tgggccttttg aatccggaca caaaaccctc tagcttggaa atgaatatgc     120
tgcactttac aaccactgca ctacctgact caggaatcgg ctctggaagg tgaagctaga     180
ggaaccagac ctcatcagcc caacatcaaa gacaccatcg gaacagcagc gcccgcagca     240
cccaccccgc accggcgact ccatcttcat ggccaccccc tgcggtggac ggttgaccac     300
cagccaccac atcatcccag agctgagctc ctccagcggg atgacgccgt ccccaccacc     360
tccctcttct tcttttttcat ccttctgtct ctttgt                              396
```

<210> SEQ ID NO 123
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 123

```
gccctttttt tttttttttt tttcctagtg ccaggtttat tccctcacat gggtggttca      60
catacacagc acanaggcac gggcaccatg gganagggca gcactcctgc cttctgaggg     120
gatcttggcc tcacggtgta anaagggana ggatggtttc tcttctgccc tcactagggc     180
ctagggaacc cagnagcaaa tcccaccacg ccttccatnt ctcagccaag ganaagccac     240
cttggtgacg tttagttcca accattatag taagtggana agggattggc ctggtcccaa     300
ccattacagg gtgaanatat aaacagtaaa ggaanataca gtttggatga ggccacagga     360
aggagcanat gacaccatca aaagcatatg caggga                              396
```

<210> SEQ ID NO 124
<211> LENGTH: 396
<212> TYPE: DNA
<213> ORGANISM: Homo sapien

<400> SEQUENCE: 124

```
gaccattgcc ccagacctgg aagatataac attcagttcc caccatctga ttaaaacaac    60
ttcctcccct acagagcata caacagaggg ggcacccggg gaggagagca catactgtgt   120
tccaatttca cgcttttaat tctcatttgt tctcacacca acagtgtgaa gtgcgtggta   180
taatctccat ttcaaaacca aggaagcagc ctcagagtgg tcgagtgaca cacctcacgc   240
aggctgagtc cagagcttgt gctcctcttg attcctggtt tgactcagtt ccaggcctga   300
tcttgcctgt ctggctcagg gtcaaagaca gaatggtgga gtgtagcctc cacctgatat   360
tcaggctact cattcagtcc caaatatgta ttttcc                             396
```

<210> SEQ ID NO 125
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 125

```
cccttttttt tttttttttt tttttttttt tttttttactt tgnaacaaaa atttattagg    60
attaagtcaa attaaaaaac ttcatgcncc nccncttgtc atatttacct gaatgacaa    120 agttatactt agcttgagng naaaacttgn gccccaaaaa ttntgtttgg aaagcaaaaa   180
aataattgat gcncatagca ngggcctga tnccnccaca ngaatgttg tttaaggnct    240 aacaaacagg ggcancaaa gcatacatta cttttaagct ttgggnccaa ggaaaangtc   300
attccctacc tccttcaaaa gcaaactcat natagcctgg gcncctaggn ctggagcctn   360 tttttcgag tctaanatga acatntggat ttcaan                              396
```

<210> SEQ ID NO 126
<211> LENGTH: 396
<212> TYPE: DNA
<213> ORGANISM: Homo sapien

<400> SEQUENCE: 126

```
cgcgtcgact cgcaagtgga atgtgacgtc cctggagacc ctgaaggctt tgcttgaagt    60
caacaaaggg cacgaaatga gtcctcaggt ggccaccctg atcgaccgct tgtgaaggg   120 aaggggccag ctagacaaag acaccctaga caccctgacc gccttctacc ctgggtacct   180
gtgctccctc agccccgagg agctgagctc cgtgcccccc agcagcatct gggcggtcag   240
gccccacgac ctgacacgc tggggctacg gctacagggc ggcatcccca acggctacct   300
ggtcctagac ctcagcatgc aagaggccct ctcggggacg ccctgcctcc taggacctgg   360
acctgttctc accgtcctgg cactgctcct agcctc                             396
```

<210> SEQ ID NO 127
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 127

```
tttttttttt ttggnggtaa aatgcaaatg ttttaaaata tgtttatttt gtatgtttta    60
caatgaatac ttcagcaaag aaaataatta taatttcaaa atgcaatccc tggatttgat   120
```

```
aaatatcctt tataatcgat tacactaatc aatatctaga aatatacata gacaaagtta    180
gctaatgaat aaaataagta aaatgactac ataaactcaa tttcagggat gagggatcat    240
gcatgatcag ttaagtcact ctgccacttt taaaataat acgattcaca tttgcttcaa    300
tcacataaac attcattgca ggagttacac ggctaatcat tgaaaattat gatctttgtt    360
agcttaaaag aaaattcagt ttaatacaaa gacatt                             396
```

<210> SEQ ID NO 128
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 128

```
gcccttttt tttttttta aggcaaata aaataagttt attgggatgt aaccccatca      60
taaattgagg agcatccata caggcaagct ataaaatctg gaaatttaa atcaaattaa    120 attctgcttt taaaaggtg ccttaagtta accaagcatt ttgataacac attcaaattt    180
aatatataaa aatagatgta tcctggaaga tataatgaan aacatgccat gtgtataaat    240
tcanaatacg cttttacac aaagaactac aaaaagttac aaagacagcc ttcaggaacc    300
acacttagga aaagtgagcc gagcagcctt cacgcaaagc ctccttcaaa naagtctcac    360
aaagactcca gaaccagccg agtntgtgaa aaagga                             396
```

<210> SEQ ID NO 129
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 129

```
gcccttttt tttttttttt ttttactcag acaggcaata tttgctcaca tttattctct    60
tgcatcgtaa atagtagcca actcacaaaa ataaagtata caanaatgta atattttta    120 aaataagatt aacagtgtaa gaaggaaaat ctcaaaaaaa gcanatagac aatgtanaaa    180
attgaaatga atcccacag taanaaaaaa aaacanaaa agtgcctatt taanaattat    240
gctacatgtg gaacttaact agaccatttt aanaagacc aatttctaat gcaaattttc    300
tgaggttttc anattttatt tttaaaatat gttatagcta catgttgtcn acncggccgc    360
tcgagtctan agggcccgtt taaacccgct gatcag                             396
```

<210> SEQ ID NO 130
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 130

```
cgccctttt tttttttttt tanngnacgt gnctttattt ctggatgata taaaanaaaa    60
aacttaaaaa acaccccaaa ccaaacacca atggatcccc aaagcgatgt gactccctct    120
tcccacccgg ataaatagag acttctgtat gtcagtctac cctcccgccc ccataacccc    180
```

| | |
|---|---|
| ctctgctata nacatactct gggtatatat tactctactc ggcaatagac atctcccgaa | 240 |
| aatagaattc ctgccctgac acctgactct tccctggccg catcanacca cccgccactg | 300 |
| tagcacactg gtgtccttgc ccctgtggt cagggccatg ctgtcatccc acaanaaggc | 360 |
| cacatttgtc acatggctgc tgtgtccacc gtactt | 396 |

<210> SEQ ID NO 131
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 131

| | |
|---|---|
| gcccttttt tttttttttt tttttttttt ttcagtttac acaaaaacnc tttaattgac | 60 |
| agtatacnnt tttccaaaat atnttttngt aanaaaatgc ataattatt aactatagtt | 120 |
| tttacaaaca agtttntcan taaattccag tgtncttnaa accccnnncn annaaaacat | 180 |
| atatgancccc ccagttcctg ggcaaactgt tgaacattca ctgcanacaa aaagaccanc | 240 |
| nccaaanagt catctgngnc ctccatgctg ngtttgcacc aaacctgagg gancagctag | 300 |
| ngaccgtgac aaaagctntg ctacagtttt actntngccc tntntgcctc ccccatnatg | 360 |
| tttccttggt ccctcantcc tgtnggagta agttcc | 396 |

<210> SEQ ID NO 132
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 132

| | |
|---|---|
| cgcgtcgacc gcggccgtag cagccgggct ggtcctgctg cgagccggcg gcccggagtg | 60 |
| gggcggcgnt atgtaccttc cacattgagt attcagaaag aagtgatctg aactctgacc | 120 |
| attctttatg gatacattaa gtcaaatata agagtctgac tacttgacac actggctcgg | 180 |
| tgagttctgc ttttcttttt taatatataat ttattatgtt ggtaaattta gcttttggct | 240 |
| tttcactttg ctctcatgat ataagaaaat gtaggttttc tctttcagtt tgaattttcc | 300 |
| tattcagtaa aacaacatgc tagaaaacaa acttttggaa aggcattgta actatttttt | 360 |
| caaatagaac cataataaca agtcttgtct taccct | 396 |

<210> SEQ ID NO 133
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 133

| | |
|---|---|
| ntattacccc tcctggnnan ntggnnatan nctgcaaggn gatnncccg nngaacttca | 60 |
| ctgatnnncc aatnaaaact gctttaaanc tgactgcaca tatgaattnt aatacttact | 120 |
| tngcgggagg ggtgggcag ggacagcaag ggggaggatt gggaaacaa tagacaggca | 180 |
| tgctggggat gcngcgggct ctatggcttc tgangcgnaa agaaccagct ggggctctag | 240 |

| | |
|---|---|
| ggggtatccc cacgcgccct gtagcngcnc attaaacgcg gcgggtgtgg nggttacttc | 300 |
| gcaaagngac cgatncactt gccagcgccc tagctgcccg ctcctttngc tttcttccct | 360 |
| tcctttctcg ccacnttnnc cggctntccc cgncaa | 396 |

<210> SEQ ID NO 134
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 134

| | |
|---|---|
| ttttttttt ttctgctttt tatatgttta aaatctctc attctattgc tgctttattt | 60 |
| aaagaaagat tactttcttc cctacaagat ctttattaat tgtaaaggga aaatgaataa | 120 |
| ctttacaatg ganacacctg gcanacacca tcttaaccaa agcttgaagt taacataacc | 180 |
| agtaatagaa ctgatcaata tcttgtgcct cctgatatgg ngtactaana aaacacaac | 240 |
| atcatgccat gatagtcttg ccaaaagtgc ataacctaaa tctaatcata aggaaacatt | 300 |
| anacaaactc aaattgaagg acattctaca aagtgccctg tattaaggaa ttattcanag | 360 |
| taaaggagac ttaaaagaca tggcaacaat gcagta | 396 |

<210> SEQ ID NO 135
<211> LENGTH: 396
<212> TYPE: DNA
<213> ORGANISM: Homo sapien

<400> SEQUENCE: 135

| | |
|---|---|
| gcgtcgacgc tggcagagcc acaccccaag tgcctgtgcc cagagggctt cagtcagctg | 60 |
| ctcactcctc cagggcactt ttaggaaagg gttttttagct agtgttttc ctcgctttta | 120 |
| atgacctcag ccccgcctgc agtggctaga agccagcagg tgcccatgtg ctactgacaa | 180 |
| gtgcctcagc ttccccccgg cccgggtcag gccgtgggag ccgctattat ctgcgttctc | 240 |
| tgccaaagac tcgtggggc catcacacct gccctgtgca gcggagccgg accaggctct | 300 |
| tgtgtcctca ctcaggtttg cttcccctgt gcccactgct gtatgatctg ggggccacca | 360 |
| ccctgtgccg gtggcctctg ggctgcctcc cgtggt | 396 |

<210> SEQ ID NO 136
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 136

| | |
|---|---|
| ttatgcttcc ggctcgtntg ttgtgtggaa ttgtgagcgg ataacaattt cacacaggaa | 60 |
| acagctatga ccatgattac gccaagctat ttaggtgaca ctatagaata ctcaagctat | 120 |
| gcatcaagct tggtaccgag ctcggatcca ctagtaacgg ccgccagtgt gctggaattc | 180 |
| gcggncgntc nantctagag ggcccgttta aacccgctga tcagcctcga ctgtgccttc | 240 |
| tagttgccag ccatctgttg tttgcccctc cccgtgcct tccttgaccc tggaaggtgc | 300 |
| cactcccact gtcctttcct aataaaatga ggaaattgca tcgcattgtc tgagtaggtg | 360 |

```
tcattctatt ctgggggtg gggtggggca ggacan                                    396
```

<210> SEQ ID NO 137
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 137

```
tttttttttt ttctgctttg tacttgagtt tatttcacaa aaccacggag aaagatactg          60
aaatggagct ctttccagcc tccaagcaag gaggccccag cagccagtct ccagccccctt       120
gagccctttt tgttaggccc acacccaaaa gagganaacc agtgtgtgcg cgaaggtaca        180
tggcaaggca cttttgaaaa catcccagtt taccgnggtg aaattgaact tactctgaaa        240
cagatgaaaa gggacatgca aaattgctga gcacatggag gtgtttgtta gtaggtgaaa        300
atcatgtcct gggtataacc cagcttctcc aggttagggt gagccgccgt ctggatcagt        360
ggtggcgggc cacacaccag gatgagcgtg gacttc                                   396
```

<210> SEQ ID NO 138
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 138

```
cccttttttt tttttttttac aaatgagaaa aatgtttatt aagaaaacaa tttagcagct        60
ctcctttana attttacaga ctaaagcaca acccgaaggc aattacagtt tcaatcatta       120
acacactact taaggngctt gcttactcta caactggaaa gttgctgaag tttgtgacat       180
gccactgtaa atgtaagtat tattaaaaat tacaaattgt ttggtgatta ttttgatgac       240
ctcttgagca gcagctcccc ccaanaatgc ancaatggta tgtggctcac cagctccata       300
tcggcaaaat tcgtggacat aatcatcttt caccattaca gataaaccat attcctgaag       360
gaagccagtg agacaagact tcaactttcc tatatc                                  396
```

<210> SEQ ID NO 139
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 139

```
ccgccctttt tttttttttt ttcacaaaag cactttttat ttgaggcaaa nagaagtctt        60
gctgaaagga ttccagttcc aagcagtcaa aactcaaccg ttagnggcac tattttgacc      120
tggtanattt tgcttctctt tggtcanaaa agggtattca ggttgtactt tccccagcag      180
ggtaaaaaga agggcaaagc aaactggaan anacttctac tctactgaca gggctnttga      240
natccaacat caagctanac acnccctcgc tggccactct acaggttgct gtcccactgc      300
tgagtgacac aggccatact acatttgcaa ggaaaaaaat gaggcaanaa acacaggtat      360
aggtcacttg gggacgagca ggcaaccaca gcttca                                   396
```

<210> SEQ ID NO 140
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 140

| | | | | | |
|---|---|---|---|---|---|
| tttttttttt | tttttttttt | ttttttttctc | atttaacttt | tttaatgggn | ctcaaaattn | 60 |
| tgngacaaat | ttttggtcaa | gttgtttcca | ttaaaaagtn | ctgattttaa | aaactaataa | 120 |
| cttaaaactg | ccncncccaa | aaaaaaaaac | caaaggggtc | cacaaaacat | tntcctttcc | 180 |
| ttntgaaggn | tttacnatgc | attgttatca | ttaaccagtn | ttttactact | aaacttaaan | 240 |
| ggccaattga | aacaaacagt | tntganaccg | ttnttccncc | actgattaaa | agngggggg | 300 |
| caggtattag | ggataatatt | catttancct | tntgagcttt | ntgggcanac | ttggngacct | 360 |
| tgccagctcc | agcagccttn | ttgtccactg | ntttga | | | 396 |

<210> SEQ ID NO 141
<211> LENGTH: 396
<212> TYPE: DNA
<213> ORGANISM: Homo sapien

<400> SEQUENCE: 141

| | | | | | |
|---|---|---|---|---|---|
| acgccgagcc | acatcgctca | gacaccatgg | ggaaggtgaa | ggtcggagtc | aacggatttg | 60 |
| gtcgtattgg | gcgcctggtc | accagggctg | cttttaactc | tggtaaagtg | gatattgttg | 120 |
| ccatcaatga | cccccttcatt | gacctcaact | acatggttta | catgttccaa | tatgattcca | 180 |
| cccatggcaa | attccatggc | accgtcaagg | ctgagaacgg | gaagcttgtc | atcaatggaa | 240 |
| atcccatcac | catcttccag | gagcgagatc | cctccaaaat | caagtggggc | gatgctggcg | 300 |
| ctgagtacgt | cgtggagtcc | actggcgtct | tcaccaccat | ggagaaggct | ggggctcatt | 360 |
| tgcagggggg | agccaaaagg | gtcatcatct | ctgccc | | | 396 |

<210> SEQ ID NO 142
<211> LENGTH: 396
<212> TYPE: DNA
<213> ORGANISM: Homo sapien

<400> SEQUENCE: 142

| | | | | | |
|---|---|---|---|---|---|
| acgcaggaga | ggaagcccag | cctgttctac | cagagaactt | gcccaggtca | gaggtctgcg | 60 |
| tagaagccct | tttctgagca | tcctctcctc | tcctcacacc | tgccactgtc | ctctgcgttg | 120 |
| ctgtcgaatt | aaatcttgca | tcaccatggt | gcacttctgt | ggcctactca | ccctccaccg | 180 |
| ggagccagtg | ccgctgaaga | gtatctctgt | gagcgtgaac | atttacgagt | ttgtggctgg | 240 |
| tgtgtctgca | actttgaact | acgagaatga | ggagaaagtt | cctttggagg | ccttctttgt | 300 |
| gttccccatg | gatgaagact | ctgctgtttta | cagcttgag | gccttggtgg | atgggaagaa | 360 |
| aattgtagca | gaattacaag | acaagatgaa | ggcccg | | | 396 |

<210> SEQ ID NO 143
<211> LENGTH: 396
<212> TYPE: DNA
<213> ORGANISM: Homo sapien
<220> FEATURE:
<221> NAME/KEY: misc_feature
<222> LOCATION: (1)...(396)

<223> OTHER INFORMATION: n = A,T,C or G

<400> SEQUENCE: 143

| | | | | | |
|---|---|---|---|---|---|
| tttttttttt | tttccatana | aaataggatt | tattttcaca | tttaaggnga | acacaaatcc | 60
| atgttccana | aatgttttat | gcataacaca | tcatgagtag | attgaatttc | tttaacacac | 120
| anaaaaatca | aagcctacca | ggaaatgctt | ccctccggag | cacaggagct | tacaggccac | 180
| ttntgttagc | aacacaggaa | ttcacattgt | ctaggcacag | ctcaagngag | gtttgttccc | 240
| aggttcaact | gctcctaccc | ccatgggccc | tcctcaaaaa | cgacagcagc | aaaccaacag | 300
| gcttcacagt | aaccaggagg | aaagatctca | gnggggaac | cttcacaaaa | gccctgagtt | 360
| gtgtttcaaa | agccaagctc | tggggtctgn | ggcctg | | | 396

<210> SEQ ID NO 144
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 144

| | | | | | |
|---|---|---|---|---|---|
| tttttttttt | tttcgctctt | tggtctgaca | agaaaagagt | tttaggtgtg | tgaagtaggg | 60
| tgggaaaaaa | ggtcagtttc | aaattcagta | acatatggta | acactaagtt | aggctgctgc | 120
| attcttttct | ttgggtactt | aagccagctg | gcacttccac | tttgtaacca | attatattat | 180
| gatcaacaac | taatcagtta | gttcctcagc | ttcaactgaa | nagttcctga | ttacctgatg | 240
| aaggacatac | ttgctctggc | ttcaattagc | atgctgtcaa | gcatccctct | ccatgcttaa | 300
| catggcaaca | caaaacccaa | gagtccttct | nttttttca | ttagccatga | ataaacactc | 360
| acaagggga | agagtagaca | ctgcttttag | taaacg | | | 396

<210> SEQ ID NO 145
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 145

| | | | | | |
|---|---|---|---|---|---|
| tttttttttt | ttttttttcaa | tggatccgtt | agctttacta | ctaanatctt | gctganatca | 60
| nanagggct | tctgggcagg | ctgagcactg | ggggtgtgca | acatggtaac | tctgaataan | 120
| anaaaccctg | agttttactg | ggcaaanaaa | naacaagngg | taggtatgat | ttctgaacct | 180
| ggaaatagcg | aaaatgaagg | aaattccaaa | agcgcgtatt | tccaaataat | gacaggccag | 240
| caagaggaca | ccaaacctnt | anaagaggt | attntttctt | ccagctactg | atggctttgg | 300
| catcccacag | gcacattcct | ttggccttca | ggatcttana | tgcanatgtg | ganagtcaag | 360
| aggtaggctg | actctgagtc | ttcagctaaa | ttctttt | | | 396

<210> SEQ ID NO 146
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 146

```
tttttttttt ttttcattag caaggaagga tttatttttt cttttgaggg gagggcggaa     60
cagccgggat ttttggaaca ctacctttgt ctttcactt gttgtttgtg tgttaacacn    120
aataaatcan aagcgacttt aaatctccct tcgcaggact gtcttcacgt atcagngcan    180
acaanaaaac agtggcttta caaaaaanat gttcaagtag ctgcacttt gcctctgngg    240
gtgaggcaca ctgngggana nacaaggtcc cctgnaacca gaggngggaa ggacanagct    300
ggctgactcc ctgctctccc gcattctctc ctccatgtgt tttgaanagg aagcaacat    360
gttgaggtct gatcatttct acccagggaa cctgtt                             396
```

<210> SEQ ID NO 147
<211> LENGTH: 396
<212> TYPE: DNA
<213> ORGANISM: Homo sapien

<400> SEQUENCE: 147

```
acggggaagc caagtgaccg tagtctcatc agacatgagg gaatgggtgg ctccagagaa     60
agcagacatc attgtcagtg agcttctggg ctcatttgct gacaatgaat tgtcgcctga    120
gtgcctggat ggagcccagc acttcctaaa agatgatggt gtgagcatcc ccggggagta    180
cacttccttt ctggctccca tctcttcctc caagctgtac aatgaggtcc gagcctgtag    240
ggagaaggac cgtgaccctg aggcccagtt tgagatgcct tatgtggtac ggctgcacaa    300
cttccaccag ctctctgcac cccagccctg tttcaccttc agccatccca acagagatcc    360
tatgattgac aacaaccgct attgcacctt ggaatt                             396
```

<210> SEQ ID NO 148
<211> LENGTH: 396
<212> TYPE: DNA
<213> ORGANISM: Homo sapien

<400> SEQUENCE: 148

```
acgtcccatg attgttccag accatgactc ttcctggttg tgggtttgtt acagagcagg     60
agaagcagag gttatgacag ttatgcagac tttccccctc cttttttctct tttctcttcc    120
ccttgctttt ccactgtttc ttcctgctgc cacctgggcc ttgaattcct gggctgtgaa    180
gacatgtagc agctgcaggg tttaccacac gtgggagggc agcccagtac tgtccctctg    240
ccttccccac tttgagaata tggcagcccc tttcattcct ggcttgggt  aggggagacc    300
attgaagtag aagcctcaaa gcagacttt ccctttactg tgtgtactcc aggacgaaga    360
aggaagatca tgcttgatac ttagattggt tttccc                             396
```

<210> SEQ ID NO 149
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 149

```
tttttttttt tttaaagagt cacatttat tcaatgccta tttgtacatg ttactagcaa      60
taaactcttt tatctttaat tttgagaagt tttacaaata cagcaaagca gaatgactaa    120
tagagccggt aaccaggaca cagatttgga aaaataggtc taattggttg ttacactgtg    180
```

-continued

```
tttatgtcat acatttcgct tattttatc aaanaaaaat cagaatttat aaaatgttaa      240
ttaaaaggaa acattctga gtaaatttag tcccgtgttt cttcctccaa atctntttgt      300
tctacactaa caggtcagga taagtatgga tggggaggct ggaaaaaggg catccttccc     360
catgcggtcc ccagagccac cctctccaag caggac                              396
```

<210> SEQ ID NO 150
<211> LENGTH: 396
<212> TYPE: DNA
<213> ORGANISM: Homo sapien

<400> SEQUENCE: 150

```
acgcctctct tcagttggca cccaaacatc tggattggca aatcagtggc aagaagttcc      60
agcatctgga cttttcagaa ttgatcttaa gtctactgtc atttccagat gcattatttt     120
acaactgtat ccttggaaat atatttctag ggagaatatt attgaagaaa atgttaatag     180
cctgagtcaa atttcagcag acttaccagc atttgtatca gtggtagcaa atgaagccaa     240
actgtatctt gaaaaacctg ttgttccttt aaatatgatg ttgccacaag ctgcattgga     300
gactcattgc agtaatattt ccaatgtgcc acctacaaga gagatacttc aagtctttct     360
tactgatgta cacatgaagg aagtaattca gcagtt                              396
```

<210> SEQ ID NO 151
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 151

```
acaaaatgcc cagcctacag agtctgagaa ggaaatttat aatcaggtga atgtagtatt      60
aaaagatgca gaaggcatct tggaggactt gcagtcatac agaggagctg gccacgaaat     120
acgagaggca atccagcatc cagcanatga gaagttgcaa gagaaggcat ggggtgcagt     180
tgttccacta gtaggcaaat taaagaaatt ttacgaattt tctcagaggt tagaagcagc     240
attaagaggt cttctgggag ccttaacaag taccccatat tctcccaccc agcatctana     300
gcgagagcag gctcttgcta aacagtttgc anaaattctt catttcacac tccggtttga     360
tgaactcaag atgacaaatc ctgccataca gaatga                              396
```

<210> SEQ ID NO 152
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 152

```
acgcagcgct cggcttcctg gtaattcttc acctcttttc tcagctccct gcagcatggg      60
tgctgggccc tccttgctgc tcgccgccct cctgctgctt ctctccggcg acggcgccgt     120
gcgctgcgac acacctgcca actgcaccta tcttgacctg ctgggcacct gggtcttcca     180
ggtgggctcc agcggttccc agcgcgatgt caactgctcg gttatgggac cacaagaaaa     240
aaaagtagng gtgtacctttc agaagctgga tacagcatat gatgaccttg caattctgg     300 ccatttcacc atcatttaca accaaggctt tgagattgtg ttgaatgact acaagtggtt     360
```

```
tgccttttt  aagtataaag  aagagggcag  caaggt                               396
```

<210> SEQ ID NO 153
<211> LENGTH: 396
<212> TYPE: DNA
<213> ORGANISM: Homo sapien

<400> SEQUENCE: 153

```
ccagagacaa  cttcgcggtg  tggtgaactc  tctgaggaaa  aacacgtgcg  tggcaacaag    60
tgactgagac  ctagaaatcc  aagcgttgga  ggtcctgagg  ccagcctaag  tcgcttcaaa   120
atggaacgaa  ggcgtttgcg  gggttccatt  cagagccgat  acatcagcat  gagtgtgtgg   180
acaagcccac  ggagacttgt  ggagctggca  gggcagagcc  tgctgaagga  tgaggccctg   240
gccattgccg  ccctggagtt  gctgcccagg  gagctcttcc  cgccactctt  catggcagcc   300
tttgacggga  gacacagcca  gaccctgaag  gcaatggtgc  aggcctggcc  cttcacctgc   360
ctccctctgg  gagtgctgat  gaagggacaa  catctt                              396
```

<210> SEQ ID NO 154
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 154

```
acagcaaacc  tcctcacagc  ccactggtcc  tcaagagggg  cnacntcttc  acacatcanc    60
acaactacgc  attgcctccc  tncactcgga  aggactatcc  tgctgccaag  agggtcaagt   120
tggacagtgt  cagagtcctg  agacagatca  gcaacaaccg  aaaatgcacc  agccccaggt   180
cctcggacac  cgaggagaat  gtcaagaggc  gaacacacaa  cgtcttggag  cgccagagga   240
ggaacgagct  aaaacggagc  ttttttgccc  tgcgtgacca  gatcccggag  ttggaaaaca   300
atgaaaaggc  ccccaaggta  gttatcctta  aaaaagccac  agcatacatc  ctgtccgtcc   360
aagcagagga  gcaaaagctc  atttctgaag  aggact                              396
```

<210> SEQ ID NO 155
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 155

```
ttttttttt  tgaananaca  ggtctttaat  gtacggagtc  tcacaaggca  caaacaccct    60
caccaggacc  aaataaataa  ctccacggtt  gcaggaaggc  gcggtctggg  gaggatgcgg   120
catctgagct  ctcccaggc   tggtgggcga  gccggggtc   tgcagtctgt  gagggcctc   180
ctgggtgtgt  ccgggcctct  anagcgggtc  cagtctccag  gatgggatc   gctcactcac   240
tctccgagtc  ggagtagtcc  gccacgaggg  aggagccgan  actgcagggg  tgccgcgtgt   300
cggggggtgtc  agctgcctcc  tgggaggagc  ctgctggcna  caggggcttg  tcctgacggc   360
tcccttcctg  cccctcgggg  ctgctgcact  tggggg                              396
```

<210> SEQ ID NO 156

<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 156

| | | | | | |
|---|---|---|---|---|---|
| gaagggggc | ngggcagggg | cggaatgtan | anattantgc | catgattgaa | gatttaagaa | 60 |
| acgtgagatt | caggattttc | accacatccc | catttagtta | gcttgctcgt | ttggctggtg | 120 |
| caaatgccag | atggattatg | aacaatgaca | gtaaattaat | gcaacataat | caggtaatga | 180 |
| tgccaagcgt | atctggtgtt | ccaggtattg | taccttacc | ggaacaaatc | agtaaatcca | 240 |
| caatccctgg | cacctgttag | gcagctatta | acctagtaaa | tgctcccca | tcccatctca | 300 |
| atcagcaang | acaatcaaaa | acatttgctt | tnagtggcag | gaacactggt | acattttac | 360 |
| ttgctccaag | ggctgtgcca | acgctccctc | tctctg | | | 396 |

<210> SEQ ID NO 157
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 157

| | | | | | |
|---|---|---|---|---|---|
| tttttttttt | tttttgggga | atgtaaatct | tttattaaaa | cagttgtctt | tccacagtag | 60 |
| taaagctttg | gcacatacag | tataaaaaat | aatcacccac | cataattata | ccaaattcct | 120 |
| nttatcaact | gcatactaag | tgttttcaat | acaattttt | ccgtataaaa | atactgggaa | 180 |
| aaattgataa | ataacaggta | ananaaagat | atttctaggc | aattactagg | atcatttgga | 240 |
| aaaagtgagt | actgnggata | tttaaaatat | cacagtaaca | agatcatgct | tgttcctaca | 300 |
| gtattgcggg | ccanacactt | aagtgaaagc | anaagtgttt | gggtgacttt | cctacttaaa | 360 |
| attttggnca | tatcatttca | aaacatttgc | atcttg | | | 396 |

<210> SEQ ID NO 158
<211> LENGTH: 396
<212> TYPE: DNA
<213> ORGANISM: Homo sapien

<400> SEQUENCE: 158

| | | | | | |
|---|---|---|---|---|---|
| tttccgaaga | cgggcagctt | cagagaagag | gattattcgg | gagattgctg | gtgtggccca | 60 |
| tagactcttt | ggcatagact | ctttcgcagg | cagccactct | gagtgtggcc | agttctataa | 120 |
| ccatccccaa | actagctgga | gcctgatgga | taggaacggg | tagtctgtcc | tcttccccat | 180 |
| aaaaatgttc | caaaaagtta | tctccagaga | gagtcccta | tgaagacagt | tgccaagctg | 240 |
| tattctcatt | ctttaaacca | atacccaggt | cagggctagt | tcacactagc | actgttaggg | 300 |
| acatggtgtg | gctagaaatg | aattgagtgt | gacttctccc | tacaacccca | ggcccaggga | 360 |
| taggaggagg | cagaggggtg | cctggagttt | ctgcac | | | 396 |

<210> SEQ ID NO 159
<211> LENGTH: 396
<212> TYPE: DNA
<213> ORGANISM: Homo sapien

<400> SEQUENCE: 159

```
tccgcgcgtt gggaggtgta gcgcggctct gaacgcgctg agggccgttg agtgtcgcag        60
gcggcgaggg cgcgagtgag gagcagaccc aggcatcgcg cgccgagaag gccgggcgtc       120
cccacactga aggtccggaa aggcgacttc cgggggcttt ggcacctggc ggaccctccc       180
ggagcgtcgg cacctgaacg cgaggcgctc cattgcgcgt gcgcgttgag gggcttcccg       240
cacctgatcg cgagacccca acggctggtg gcgtcgcctg cgcgtctcgg ctgagctggc       300
catggcgcag ctgtgcgggc tgaggcggag ccgggcgttt ctcgccctgc tgggatcgct       360
gctcctctct ggggtcctgg cggccgaccg agaacg                                 396
```

<210> SEQ ID NO 160
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 160

```
ggaaaccttc tcaactaaga gaacatcatt tctggcaaac tattttgtt agctcacaat         60 atatgtcgta cactctacaa tgtaaatagc actganccac ancttacaga aggtaaaaag       120
angnataana acttccttta caaaanantt cctgttgttc ttaatactcc ccattgctta       180
tganaattnt ctatangtct ctcangantg ttcgcaccca tttcttttnt aacttctact       240
aaaaanccat ttacattgna nagtgtacna cntatatttg ngagctaaca aaaaatngtt       300
ttccnganat gatgttcttt tagtttnaga nggttcnnnc aanttnctac tccngcccgc       360
cactgnncnc cacatttnnn naattacacc ncacng                                 396
```

<210> SEQ ID NO 161
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 161

```
tttttgtttg attatttta ttataatgaa attaaactta tgactattac agtatgctca         60
gcttaaaaca tttatgagta ctgcaaggac taacagaaac aggaaaaatc ctactaaaaa       120
tatttgttga tgggaaatca ttgtgaaagc aaacctccaa atattcattt gtaagccata       180
agaggataag cacaaccata tgggaggaga taaccagtct ctcccttcat atatattctt       240
ttttatttct tggtataacct tcccaaaaca nanacattca acagtagtta gaatggccat      300
ctcccaacat tttaaaaaaa ctgcncccccc caatgggtga acaaagtaaa gagtagtaac      360
ctanagttca gctgagtaag ccactgtgga gcctta                                 396
```

<210> SEQ ID NO 162
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 162

-continued

| | |
|---|---|
| tttttttttt tttttttttt tttttttttt ttngggggncc aaattttttt ntttgaagga | 60 |
| angggacaaa nnaaaaaact taagggggntg ttttggnncn acttanaaaa aagggaaagg | 120 |
| aaacccccaac atgcatgccc tnccttgggg accanggaan ncnccccncn ggtntgggga | 180 |
| aantaacccn aggnttaact ttnattatca ctgncnccca ggggggggctt nnaaaaaaaa | 240 |
| nnttccccca anccaaantn gggnncnccc attttncnca anttggncnc cnggncnccc | 300 |
| natttttttga ngggtttcnc cngcncattn agggaanggg nntcaannaa accncncaaa | 360 |
| nggggggnnat tttntcang ggccnatttg ngcnnt | 396 |

<210> SEQ ID NO 163
<211> LENGTH: 396
<212> TYPE: DNA
<213> ORGANISM: Homo sapien

<400> SEQUENCE: 163

| | |
|---|---|
| cactgtccgg ctctaacaca gctattaagt gctacctgcc tctcaggcac tctcctcgcc | 60 |
| cagtttctga ggtcagacga gtgtctgcga tgtcttcccg cactctattc ccccagcctc | 120 |
| tttctgcttt catgctcagc acatcatctt cctaggcagt ctcttcccca aagtctcacc | 180 |
| ttttcttcca atagaaaatt ccgcttgacc tttggtgcac tgcccacttc ccagctccac | 240 |
| tggcccaagt ctgagccgga ggcccttgtt ttggggggcgg ggggagagtt ggatgtgatt | 300 |
| gcccttgaag aacaaggctg acctgagagg ttcctggcgc cctgaggtgg ctcagcacct | 360 |
| gcccagggta ggcctggcat gaggggttag gtcagc | 396 |

<210> SEQ ID NO 164
<211> LENGTH: 396
<212> TYPE: DNA
<213> ORGANISM: Homo sapien

<400> SEQUENCE: 164

| | |
|---|---|
| gacacgcggc ggtgtcctgt gttggccatg gccgactacc tgattagtgg gggcacgtcc | 60 |
| tacgtgccag acgacggact cacagcacag cagctcttca actgcggaga cggcctcacc | 120 |
| tacaatgact ttctcattct ccctgggtac atcgacttca ctgcagacca ggtggacctg | 180 |
| acttctgctc tgaccaagaa aatcactctt aagaccccac tggtttcctc tcccatggac | 240 |
| acagtcacag aggctgggat ggccatagca atggcgctta caggcggtat tggcttcatc | 300 |
| caccacaact gtacacctga attccaggcc aatgaagttc ggaaagtgaa gaaatatgaa | 360 |
| cagggattca tcacagaccc tgtggtcctc agcccc | 396 |

<210> SEQ ID NO 165
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 165

| | |
|---|---|
| tttttttttt tttttttttt tttttttcang ggncactgag gcttttttatt ttgancncaa | 60 |
| aaccnccggg gatctanccct gnggccnccc cggaaatnac ncnaggctca catnactnta | 120 |
| aacncttggg ggaaagggag gcaaaaaaaa caatgacttg ggccaattnc ncnactgcaa | 180 |
| agntananct gccaacaggg ctccagggag cttggnttnt gtaaaanttn taaggaagcg | 240 |
| gnncnaactc cncggggggg gggcnctaac tancagggac ccctgcaagn gttggncggg | 300 |

```
ggcctcaacc tgcctgagct nacncaaggg gngggggtntn tntanccaac aggggaccna    360
agggcttgcc tncccacagn ttacttggcc aaggg                                396
```

<210> SEQ ID NO 166
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 166

```
tttttttcaaa ttcagagcat ttttattaaa agaacaaaat attaaggcac aaaatacatc     60
aatttttcaa atgaaaaccc ttcaaacggt tatgtcctac attcaacgaa acttcttcca    120
aattacggaa taatttaact ttttaaaata naaaaataca agttcttaaa tgcctaaaat    180
ttctccccaa ataaatgttt tcttagtttt aatgaagtct cttcatgcag tactgagctc    240
caatattata atgtncactt ccttaaaaat ctagttttgc cacttatata cattcaatat    300
gtttaaccag tatattaacc agtatattaa ccaatatgtt aaacttcttt taagtataag    360
gcttggtatt ttgtattgct tattgcatgc tttgat                               396
```

<210> SEQ ID NO 167
<211> LENGTH: 396
<212> TYPE: DNA
<213> ORGANISM: Homo sapien

<400> SEQUENCE: 167

```
tggcggcagc ggcggtggcg gtggctgagc agaggacccg gcgggcggcc tcgcgggtca     60
ggacacaatg tttgcacgag gactgaagag gaaatgtgtt ggccacgagg aagacgtgga    120
gggagccctg gccggcttga agacagtgtc ctcatacagc ctgcagcggc agtcgctcct    180
ggacatgtct ctggtgaagt tgcagctttg ccacatgctt gtggagccca atctgtgccg    240
ctcagtcctc attgccaaca cggtccggca gatccaagag gagatgacgc aggatgggac    300
gtggcgcaca gtggcacccc aggctgcaga gcgggcgccg ctcgaccgct tggtctccac    360
ggagatcctg tgccgtgcag cgtggggggca agaggg                              396
```

<210> SEQ ID NO 168
<211> LENGTH: 396
<212> TYPE: DNA
<213> ORGANISM: Homo sapien

<400> SEQUENCE: 168

```
taggatggta agagtattat aaggattggt acaaggcatg atgagtcctt ttgcttttag     60
gcttttgact tctggtttta gactttcttt agcttctgtt gttagacaac attgtgcaag    120
cttggttttt ataagtttgc atggattaaa ctgaacttaa tgaaattgtc cctcccccca    180
aattctcagc acaattttta ggcccacaag gagtcaagca cctcaaggag atcttcagtt    240
tgaacttggt gtagacacag ggatactgat gaatcaatat tcaaattagc tgttacctac    300
ttaagaaaga gaggagacct tgggattc gaggaagggt tcataaggga gattttagct     360
gagaaatacc atttgcacag tcaatcactt ctgacc                               396
```

<210> SEQ ID NO 169
<211> LENGTH: 396
<212> TYPE: DNA

<210> SEQ ID NO 169
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 169

```
ttttttttttt tttcanaatt aaattcttta atacaaaatg cttttttttt tttaaaanat    60
atctgtattt ctttgncgtt gttnaaaaat aaatatgtnc tacggaatat ntcnaaaaac   120
tgcnctaaaa acaaanacgn gatgttaata tcttttcccc ncaattntta cggataaaca   180
gtancccna taaataaatg atancnaatn ttaaaattaa aaaagganan anatttagta   240
tgnaaaattc tctattttttt cttggtttgg ttttncntat aaaaaacana atagcaatgt   300
ntnttttatc anaatcccnt ntntncctaa acnttttttt ttttntttnc cccnaatnc    360
aagnngccaa anatntntnt agnatgnana tgtntn                              396
```

<210> SEQ ID NO 170
<211> LENGTH: 396
<212> TYPE: DNA
<213> ORGANISM: Homo sapien

<400> SEQUENCE: 170

```
tgagaagtac catgccgctt ctgcagagga acaggcaacc atcgaacgca acccctacac    60
catcttccat caagcactga aaaactgtga gcctatgatt gggctggtac ccatcctcaa   120
gggaggccgt ttctaccagg tccctgtacc cctacccgac cggcgtcgcc gcttcctagc   180
catgaagtgg atgatcactg agtgccggga taaaaagcac cagcggacac tgatgccgga   240
gaagctgtca cacaagctgc tggaggcttt ccataaccag ggccccgtga tcaagaggaa   300
gcatgacttg cacaagatgg cagaggccaa ccgtgccctg gcccactacc gctggtggta   360
gagtctccag gaggagccca gggccctctg cgcaag                              396
```

<210> SEQ ID NO 171
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 171

```
ggtcctcgtc gtggtgagcg cagccactca ggctggtcct gggggtgggg ctgtagggga    60
aagtgctaaa gccgctgagt gaagtaagaa ctctgctaga gaggaaaatg ggcttgcttt   120
catcatcatc ctnctcagct ggtggggtca agtgggaagt tctgtcactg ggatctggtt   180
cagtgtctca agaccttgcc ccaccacgga aagccttttt cacntacccc aaaggacttg   240
gagagatgtt agaagatggn tctnaaaaat tcctctgcna atntgttttt agctatcaag   300
tggcttcccc ccttaancag gnaaaacatg atcagcangt tgctcggatg gaaaaactan   360
cttggtttgn naaaaaanct ggaggcttga caatgg                              396
```

<210> SEQ ID NO 172
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 172

```
agccttgggc caccctcttg gagcatctgg ctgtcgaatt cttgtgaccc tgttacacac      60
actggagaga atgggcagaa gtcgtggtgt tgcagccctg tgcattgggg gtgggatggg     120
aatagcaatg tgtgttcaga gagaatgaat tgcttaaact ttgaacaacc tcaatttctt     180
tttaaactaa taaagtacta ggttgcaata tgtgaaaaaa aaaaaaaaag ggcggccgnt     240
cnantntana gggcccnttn aaacccgttg atcaacctcg actgtgcctt ctagttgcca     300
gccatctgtt gttngcccct cccccgtgnc tttcttgacc ttgaaagggg cccncccct      360
gtctttccta anaaaaanga agaantnncc ttccnt                              396
```

<210> SEQ ID NO 173
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 173

```
aagcatgtgg atatgtttag ctacgtttac tcacagccag cgaactgaca ttaaaataac      60
taacaaacag attcttttat gtgatgctgg aactcttgac agctataatt attattcaga     120
aatgactttt tgaaagtaaa agcagcataa agaatttgtc acaggaaggc tgtctcagat     180
aaattatggt aaaattttgc agggacann cttttttaaga cttgcacaat tnccggatcc     240
tgcnctgact ttggaaaagg catatatgtn ctagnggcat gganaatgcc ccatactcat     300
gcatgcaaat taaacaacca gtttgaatc tttttggggg ngngctatnc tttaacccng     360
tacnggcntt attatntaan gncctgnnn cntgtg                              396
```

<210> SEQ ID NO 174
<211> LENGTH: 924
<212> TYPE: DNA
<213> ORGANISM: Homo sapiens

<400> SEQUENCE: 174

```
cctgacgacc cggcgacggc gacgtctctt ttgactaaaa gacagtgtcc agtgctccag      60
cctaggagtc tacggggacc gcctcccgcg ccgccaccat gcccaacttc tctggcaact     120
ggaaaatcat ccgatcggaa aacttcgagg aattgctcaa agtgctgggg gtgaatgtga     180
tgctgaggaa gattgctgtg gctgcagcgt ccaagccagc agtggagatc aaacaggagg     240
gagacacttt ctacatcaaa acctccacca ccgtgcgcac cacagagatt aacttcaagg     300
ttggggagga gttgaggag cagactgtgg atgggaggcc ctgtaagagc tggtgaaat      360
gggagagtga gaataaaatg gtctgtgagc agaagctcct gaaggagag ggccccaaga     420
cctcgtggac cagagaactg accaacgatg gggaactgat cctgaccatg acggcggatg     480
acgttgtgtg caccagggtc tacgtccgag agtgagtggc cacaggtaga accgcggccg     540
aagcccacca ctggccatgc tcaccgccct gcttcactgc cccctccgtc ccacccctc     600
cttctaggat agcgctcccc ttaccccagt cacttctggg ggtcactggg atgcctcttg     660
cagggtcttg ctttctttga cctcttctct cctcccctac accaacaaag aggaatggct     720
gcaagagccc agatcaccca ttccgggttc actcccgcc tccccaagtc agcagtccta     780
gccccaaacc agcccagagc agggtctctc taaaggggac ttgagggcct gagcaggaaa     840
```

```
gactggccct ctagcttcta cccttttgtcc ctgtagccta tacagtttag aatatttatt    900
tgttaatttt attaaaatgc ttta                                            924
```

<210> SEQ ID NO 175
<211> LENGTH: 3321
<212> TYPE: DNA
<213> ORGANISM: Homo sapiens

<400> SEQUENCE: 175

```
atgaagattt tgatacttgg tattttctg tttttatgta gtacccagc ctgggcgaaa        60 gaaaagcatt attacattgg aattattgaa acgacttggg attatgcctc tgaccatggg    120
gaaaagaaac ttatttctgt tgacacggaa cattccaata tctatcttca aaatggccca    180
gatagaattg ggagactata agaaggcc ctttatcttc agtacacaga tgaaaccttt      240
aggacaacta tagaaaaacc ggtctggctt gggttttttag ccctattat caaagctgaa    300 actggagata agtttatgt acacttaaaa aaccttgcct ctaggccta cacctttcat      360 tcacatggaa taacttacta taaggaacat gagggggcca tctaccctga taacaccaca    420
gattttcaaa gagcagatga caaagtatat ccaggagagc agtatacata catgttgctt    480
gccactgaag aacaaagtcc tggggaagga atggcaatt gtgtgactag gatttaccat     540
tcccacattg atgctccaaa agatattgcc tcaggactca tcggaccttt aataatctgt    600 aaaaagatt ctctagataa agaaaaagaa aaacatattg accgagaatt tgtggtgatg     660 tttttctgtgg tggatgaaaa tttcagctgg tacctagaag acaacattaa aacctactgc    720
tcagaaccag agaaagttga caaagacaac gaagacttcc aggagagtaa cagaatgtat    780
tctgtgaatg gatacactt tggaagtctc ccaggactct ccatgtgtgc tgaagacaga     840
gtaaaatggt acctttttgg tatgggtaat aagttgatg tgcacgcagc tttctttcac     900
gggcaagcac tgactaacaa gaactaccgt attgacacaa tcaacctctt tcctgctacc    960
ctgtttgatg cttatatggt ggcccagaac cctggagaat ggatgctcag ctgtcagaat    1020
ctaaaccatc tgaaagccgg tttgcaagcc ttttccagg tccaggagtg taacaagtct     1080
tcatcaaagg ataatatccg tgggaagcat gttagacact actacattgc cgctgaggaa    1140
atcatctgga actatgctcc ctctggtata gacatcttca ctaaagaaaa cttaacagca    1200
cctggaagtg actcagcggt gtttttttgaa caaggtacca caagaattgg aggctcttat    1260
aaaaagctgg tttatcgtga gtacacagat gcctccttca caaatcgaaa ggagagaggc    1320
cctgaagaag agcatcttgg catcctgggt cctgtcattt gggcagaggt gggagacacc    1380
atcagagtaa ccttccataa caaggagca tatccctca gtattgagcc gattggggtg      1440
agattcaata gaacaacga gggcacatac tattccccaa attacaaccc ccagagcaga    1500
agtgtgcctc cttcagcctc ccatgtggca cccacagaaa cattcaccta tgaatggact    1560
gtccccaaag aagtaggacc cactaatgca gatcctgtgt gtctagctaa gatgtattat    1620
tctgctgtgg atccactaa agatatatcc actgggctta ttgggccaat gaaaatatgc    1680
aagaaaggaa gtttacatgc aaatgggaga cagaaagatg tagacaagga attctatttg    1740
tttcctacag tatttgatga aatgagagt ttactcctgg aagataatat tagaatgttt    1800
acaactgcac ctgatcaggt ggataaggaa gatgaagact tcaggaatc taataaaatg    1860 cactccatga atggattcat gtatgggaat cagcccgggtc tcactatgtg caaaggagat    1920
tcggtcgtgt ggtacttatt cagcgccgga aatgaggcc atgtacatgg aatatacttt    1980
tcaggaaaca catatctgtg agaggagaa cggagagaca cagcaaacct cttccctcaa    2040
```

```
acaagtctta cgctccacat gtggcctgac acagagggga cttttaatgt tgaatgcctt    2100
acaactgatc attacacagg cggcatgaag caaaaatata ctgtgaacca atgcaggcgg    2160
cagtctgagg attccacctt ctacctggga gagaggacat actatatcgc agcagtggag    2220
gtggaatggg attattcccc acaaaggagt tgggaaaagg agctgcatca tttacaagag    2280
cagaatgttt caaatgcatt tttagataag ggagagtttt acataggctc aaagtacaag    2340
aaagttgtgt atcggcagta tactgatagc acattccgtg ttccagtgga gagaaaagct    2400
gaagaagaac atctgggaat tctaggtcca caacttcatg cagatgttgg agacaaagtc    2460
aaaattatct ttaaaaacat ggccacaagg ccctactcaa tacatgccca tggggtacaa    2520
acagagagtt ctacagttac tccaacatta ccaggtgaaa ctctcactta cgtatggaaa    2580
atcccagaaa gatctggagc tggaacagag gattctgctt gtattccatg ggcttattat    2640
tcaactgtgg atcaagttaa ggacctctac agtggattaa ttggcccccct gattgtttgt    2700 cgaagacctt acttgaaagt attcaatccc agaaggaagc tggaatttgc ccttctgttt    2760
ctagtttttg atgagaatga atcttggtac ttagatgaca acatcaaaac atactctgat    2820
caccccgaga agtaaacaa agatgatgag gaattcatag aaagcaataa aatgcatgct    2880
attaatggaa gaatgtttgg aaacctacaa ggcctcacaa tgcacgtggg agatgaagtc    2940
aactggtatc tgatgggaat gggcaatgaa atagacttac acactgtaca ttttcacggc    3000
catagcttcc aatacaagca cagggagtt tatagttctg atgtctttga catttttccct    3060 ggaacatacc aaaccctaga aatgtttcca agaacacctg gaatttggtt actccactgc    3120
catgtgaccg accacattca tgctggaatg gaaaccactt acaccgttct acaaaatgaa    3180
gacaccaaat ctggctgaat gaaataaatt ggtgataagt ggaaaaaaga gaaaaaccaa    3240
tgattcataa caatgtatgt gaaagtgtaa aatagaatgt tactttggaa tgactataaa    3300
cattaaaaga gactggagca t                                              3321

<210> SEQ ID NO 176
<211> LENGTH: 487
<212> TYPE: DNA
<213> ORGANISM: Homo sapiens

<400> SEQUENCE: 176
gaaatacttt ctgtcttatt aaaattaata aattattggt cttacaaga cttggataca     60 ttacagcaga catggaaata taattttaaa aaatttctct ccaacctcct tcaaattcag    120
tcaccactgt tatattacct tctccaggaa ccctccagtg gggaaggctg cgatattaga    180
tttccttgta tgcaaagttt ttgttgaaag ctgtgctcag aggaggtgag aggagaggaa    240
ggagaaaact gcatcataac tttacagaat tgaatctaga gtcttccccg aaaagcccag    300
aaacttctct gcagtatctg gcttgtccat ctggtctaag gtggctgctt cttccccagc    360
catgagtcag tttgtgccca tgaataatac acgacctgtt atttccatga ctgctttact    420
gtatttttaa ggtcaatata ctgtacattt gataataaaa taatattctc ccaaaaaaaa    480
aaaaaaa                                                              487

<210> SEQ ID NO 177
<211> LENGTH: 3999
<212> TYPE: DNA
<213> ORGANISM: Homo sapiens

<400> SEQUENCE: 177
```

-continued

| | |
|---|---|
| caagattcca catttgatgg ggtgactgac aaacccatct tagactgctg tgcctgcgga | 60 |
| actgccaagt acagactcac attttatggg aattggtccg agaagacaca cccaaaggat | 120 |
| taccctcgtc gggccaacca ctggtctgcg atcatcggag gatcccactc caagaattat | 180 |
| gtactgtggg aatatggagg atatgccagc gaaggcgtca acaagttgc agaattgggc | 240 |
| tcacccgtga aaatggagga agaaattcga acacagagtg atgaggtcct caccgtcatc | 300 |
| aaagccaaag cccaatggcc agcctggcag cctctcaacg tgagagcagc accttcagct | 360 |
| gaattttccg tggacagaac gcgccattta atgtccttcc tgaccatgat gggccctagt | 420 |
| cccgactgga acgtaggctt atctgcagaa gatctgtgca ccaaggaatg tggctgggtc | 480 |
| cagaaggtgg tgcaagacct gattccctgg gacgctggca ccgacagcgg ggtgacctat | 540 |
| gagtcaccca acaaacccac cattccccag gagaaaatcc ggcccctgac cagcctggac | 600 |
| catcctcaga gtcctttcta tgacccagag ggtgggtcca tcactcaagt agccagagtt | 660 |
| gtcatcgaga gaatcgcacg gaagggtgaa caatgcaata ttgtacctga caatgtcgat | 720 |
| gatattgtag ctgacctggc tccagaagag aaagatgaag atgacacccc tgaaacctgc | 780 |
| atctactcca actggtcccc atggtccgcc tgcagctcct ccacctgtga caaaggcaag | 840 |
| aggatgcgac agcgcatgct gaaagcacag ctggacctca gcgtcccctg ccctgacacc | 900 |
| caggacttcc agccctgcat gggccctggc tgcagtgacg aagacggctc cacctgcacc | 960 |
| atgtccgagt ggatcacctg gtcgccctgc agcatctcct gcggcatggg catgaggtcc | 1020 |
| cgggagaggt atgtgaagca gttcccggag gacggctccg tgtgcacgct gcccactgag | 1080 |
| gaaacggaga agtgcacggt caacgaggag tgctctccca gcagctgcct gatgaccgag | 1140 |
| tggggcgagt gggacgagtg cagcgccacc tgcggcatgg gcatgaagaa gcggcaccgc | 1200 |
| atgatcaaga tgaaccccgc agatggctcc atgtgcaaag ccgagacatc acaggcagag | 1260 |
| aagtgcatga tgcagagtg ccacaccatc ccatgcttgc tgtccccatg gtccgagtgg | 1320 |
| agtgactgca gcgtgacctg cgggaagggc atgcgaaccc gacagcggat gctcaagtct | 1380 |
| ctggcagaac ttgagactg caatgaggat ctggagcagg tggagaagtg catgctccct | 1440 |
| gaatgcccca ttgactgtga gctcaccgag tggtcccagt ggtcggaatg taacaagtca | 1500 |
| tgtgggaaag gccacgtgat tcgaacccgg atgatccaaa tggagcctca gtttggaggt | 1560 |
| gcaccctgcc cagagactgt gcagcgaaaa aagtgccgca tccgaaaatg ccttcgaaat | 1620 |
| ccatccatcc aaaagctacg ctggagggag gcccgagaga gccggcggag tgagcagctg | 1680 |
| aaggaagagt ctgaagggga gcagttccca ggttgtagga tgcgcccatg gacggcctgg | 1740 |
| tcagaatgca ccaaactgtg cggaggtgga attcaggaac gttacatgac tgtaaagaag | 1800 |
| agattcaaaa gctcccagtt taccagctgc aaagacaaga aggagatcag agcatgcaat | 1860 |
| gttcatcctt gttagcaagg gtacgagttc cccagggctg cactctagat tccagagtca | 1920 |
| ccaatggctg gattatttgc ttgtttaaga caatttaaat tgtgtacgct agttttcatt | 1980 |
| tttgcagtgt ggttcgccca gtagtcttgt ggatgccaga gacatccttt ctgaatactt | 2040 |
| cttgatgggt acaggctgag tggggcgccc tcacctccag ccagcctctt cctgcagagg | 2100 |
| agtagtgtca gccaccttgt actaagctga aacatgtccc tctggagctt ccacctggcc | 2160 |
| agggaggacg gagactttga cctactccac atggagaggc aaccatgtct ggaagtgact | 2220 |
| atgcctgagt cccagggtgc ggcaggtagg aaacattcac agatgaagac agcagattcc | 2280 |
| ccacattctc atctttggcc tgttcaatga aaccattgtt tgcccatctc ttcttagtgg | 2340 |
| aactttaggt ctcttttcaa gtctcctcag tcatcaatag ttcctgggga aaaacagagc | 2400 |

```
tggtagactt gaagaggagc attgatgttg ggtggctttt gttctttcac tgagaaattc    2460
ggaatacatt tgtctcaccc ctgatattgg ttcctgatgc cccccaaca aaaataaata    2520 aataaattat ggctgcttta tttaaatata aggtagctag ttttacacc tgagataaat    2580 aataagctta gagtgtattt ttcccttgct tttgggggtt cagaggagta tgtacaattc    2640
ttctgggaag ccagccttct gaactttttg gtactaaatc cttattggaa ccaagacaaa    2700
ggaagcaaaa ttggtctctt tagagaccaa tttgcctaaa ttttaaaatc ttcctacaca    2760
catctagacg ttcaagtttg caaatcagtt tttagcaaga aaacattttt gctatacaaa    2820
cattttgcta agtctgccca aagcccccc aatgcattcc ttcaacaaaa tacaatctct    2880
gtactttaaa gttattttag tcatgaaatt ttatatgcag agagaaaaag ttaccgagac    2940
agaaaacaaa tctaagggaa aggaatatta tgggattaag ctgagcaagc aattctggtg    3000
gaaagtcaaa cctgtcagtg ctccacacca gggctgtggt cctcccagac atgcatagga    3060
atggccacag gtttacactg ccttcccagc aattataagc acaccagatt cagggagact    3120
gaccaccaag ggatagtgta aaaggacatt ttctcagttg ggtccatcag cagttttttct    3180 tcctgcattt attgttgaaa actattgttt catttcttct tttataggcc ttattactgc    3240
ttaatccaaa tgtgtaccat tggtgagaca catacaatgc tctgaataca ctacgaattt    3300
gtattaaaca catcagaata tttccaaata caacatagta tagtcctgaa tatgtacttt    3360
taacacaaga gagactattc aataaaaact cactgggtct ttcatgtctt taagctaagt    3420
aagtgttcag aaggttcttt tttatattgt cctccacctc catcatttc aataaaagat    3480 agggcttttg ctcccttgtt cttggaggga ccattattac atctctgaac taccttgta    3540 tccaacatgt tttaaatcct taaatgaatt gctttctccc aaaaaaagca caatataaag    3600
aaacacaaga tttaattatt tttctacttg gggggaaaaa agtcctcatg tagaagcacc    3660
cacttttgca atgttgttct aagctatcta tctaactctc agcccatgat aaagttcctt    3720
aagctggtga ttcctaatca aggacaagcc accctagtgt ctcatgtttg tatttggtcc    3780
cagttgggta catttttaaaa tcctgatttt ggagacttaa aaccaggtta atggctaaga    3840
atgggtaaca tgactcttgt tggattgtta tttttttgttt gcaatgggga atttataaga    3900
agcatcaagt ctctttctta ccaaagtctt gttaggtggt ttatagttct tttggctaac    3960
aaatcatttt ggaaataaag attttttact acaaaaatg                          3999
```

<210> SEQ ID NO 178
<211> LENGTH: 1069
<212> TYPE: DNA
<213> ORGANISM: Homo sapiens

<400> SEQUENCE: 178

```
aaaaaagatg aataaatgaa taagagagat gaataaacaa atttacatta catgtgatag     60
ttatcatggt atggccttca tgacaagatg gatgagaata tcactgatag gatattagcc    120
ttctttcata tctttatatt gaaatatggg ctttacttca atttgaaggt ctttcatgaa    180
caataaaaga gagtagaagg actgtctgag aaggcaggag acatataaaa cagatgactg    240
aaagactgac tagctcctgg aaagggaaac atttggaaca tccagagtaa gggcaaatgg    300
gcttctacca gcacaacaaa gagcctccag gtggcaacat ggaagcaggt tatcagagaa    360
aataaatgtg caaattcctt atttacaatg actcacttaa ccccacaaac atgtttcact    420
gctgccttcc ccagttgtcg cttatgtact gttgttacct ttcagttaca tgcctttgat    480
```

-continued

| | |
|---|---|
| cctaaaattc tctacttttg gtgccttatc agttctttgc aatctgcctg tggttatcag | 540 |
| cacttaaagc acaattttga aggggaaaaa aatgataatc accttagtcc caagaaaata | 600 |
| atttgtcaaa ctgccttatt agtattaaaa acagacacac tgaatgaagt agcatgatac | 660 |
| gcatatatcc tactcagtat cattggcctt ttatcaaatg gggaaactat acttttgtat | 720 |
| tacatagttt tagaaatcga agttagaga ctctttataa gtaatgtcaa ggaacagtaa | 780 |
| tttaaaaaca aagttctaac aaatatattg tttgcttaat cacaatgccc tcaacttgta | 840 |
| tttgaataac taaataggac atgtcttcct tggagctgtg ggcattagtt cagaagcact | 900 |
| acctgcatct taattttcaa aacttaagtt ttattagcaa atcctcttct ctgtaagact | 960 |
| tagctatgaa gtggtatatt ttttccaaat attttctga aaacatttgt tgttgtaact | 1020 |
| gcacaataaa agtccagttg caattaaaaa aaaaaaaaaa aaaaaaaa | 1069 |

<210> SEQ ID NO 179
<211> LENGTH: 1817
<212> TYPE: DNA
<213> ORGANISM: Homo sapiens

<400> SEQUENCE: 179

| | |
|---|---|
| tgctattctg ccaaaagaca atttctagag tagttttgaa tgggttgatt tcccccactc | 60 |
| ccacaaactc tgaagccagt gtctagctta ctaaaaaaag agttgtatat aatatttaag | 120 |
| atgctgagta tttcatagga aagctgaatg ctgctgtaaa gtgctcttta agtcttttt | 180 |
| ttttttaatc cccttctaat gaatgaaact aggggaattt caggggacag agatgggatt | 240 |
| tgttgtatga taaactgtat gtagttttta gtctttctgt tttgagaagc agtggttggg | 300 |
| gcatttttaa gatggctggc tactcttgtt ttccctcatg ataataaatt tgtcataact | 360 |
| cagtaacatg aacttgcccc tagaggtagt tgttaataat tttgaaatat taaggtcttg | 420 |
| ccaagcttct gatgattcac acctgtacta ctgattatta agcaggacag actgagcttt | 480 |
| ctgttgcaaa taccttggag gagaaagtaa tttctaaata tacagagagg taacttgact | 540 |
| atatatgttg catcctgtgc ctcccttcat attaatattt gataaagatt ttaatttatg | 600 |
| taaaacttct aaagcagaat caaagctcct cttggggaaa tggcaagtct ttaggatagg | 660 |
| caagaccctg tatgaatagt accaaagcat taccgcatgg tagagaacac actcgattaa | 720 |
| aaatgttaag ctatctgaaa aataaaatgt gcaagtcttc aggatggcac aaaacaaagg | 780 |
| ttaatgcttc ttggggcaca tttcttagag ggcttgctga gtgtgtaaat ataatcgact | 840 |
| tttgtttgtg ttacatgact tctgtgactt cattgaaaat ctgcacaatt cagtttcagc | 900 |
| tctggattac ttcagttgac ctttgtgaag gtttttatct gtgtagaatg ggtgtttgac | 960 |
| ttgtttagc ctattaaatt tttattttct ttcactctgt attaaaagta aaacttacta | 1020 |
| aaagaaaaga ggtttgtgtt cacattaaat ggttttggtt tggcttcttt tagtcaggct | 1080 |
| ttctgaacat tgagatatcc tgaacttaga gctcttcaat cctaagattt tcatgaaaag | 1140 |
| cctctcactt gaacccaaac cagagtactc ttactgcctc ttttctaaat gttcaggaaa | 1200 |
| agcattgcca gttcagtctt ttcaaaatga gggagaaaca tttgcctgcc ttgtaataac | 1260 |
| aagactcagt gcttatttt taaactgcat tttaaaaatt ggatagtata ataacaataa | 1320 |
| ggagtaagcc acctttata ggcaccctgt agttttatag ttcttaatct aaacattta | 1380 |
| tatttccttc ttttggaaaa aacctacatg ctacaagcca ccatatgcac agactataca | 1440 |
| gtgagttgag ttggctctcc cacagtcttt gaggtgaatt acaaaagtcc agccattatc | 1500 |
| atcctcctga gttatttgaa atgattttttt ttgtacattt tggctgcagt attggtggta | 1560 |

-continued

```
gaatatacta taatatggat catctctact tctgtattta tttatttatt actagacctc      1620
aaccacagtc ttcttttcc ccttccacct ctctttgcct gtaggatgta ctgtatgtag       1680
tcatgcactt tgtattaata tattagaaat ctacagatct gttttgtact ttttatactg      1740
ttggatactt ataatcaaaa cttttactag ggtattgaat aaatctagtc ttactagaaa      1800
aaaaaaaaaa aaaaaa                                                      1817
```

<210> SEQ ID NO 180
<211> LENGTH: 2382
<212> TYPE: DNA
<213> ORGANISM: Homo sapiens

<400> SEQUENCE: 180

```
acttttattg gaagcagcag ccacatccct gcatgatttg cattgcaata caaccataac       60
cgggcagcca ctcctgagtg ataaccagta taacataaac gtagcagcct caattttgc       120 ctttatgacg acagcttgtt atggttgcag tttgggtctg ctttacgaa gatggcgacc       180 gtaacactcc ttagaaactg gcagtcgtat gttagtttca cttgtctact ttatatgtct      240
gatcaatttg gataccattt tgtccagatg caaaaacatt ccaaagtaa tgtgtttagt       300 agagagagac tctaagctca agttctggtt tatttcatgg atggaatgtt aatttttatta    360 tgatattaaa gaaatggcct tttatttac atctctcccc tttttccctt tccccctta       420 ttttcctcct tttctttctg aaagtttcct tttatgtcca taaatacaa atatattgtt      480 cataaaaaat tagtatccct tttgtttggt tgctgagtca cctgaacctt aattttaatt    540
ggtaattaca gccctaaaa aaacacatt tcaataggc ttcccactaa actctatatt        600
ttagtgtaaa ccaggaattg gcacactttt tttagaatgg gccagatggt aaatatttat    660
gcttcacggt ccatacagtc tctgtcacaa ctattcagtt ctgctagtat agcgtgaaag    720
cagctataca caatacagaa atgaatgagt gtggttatgt tctaataaaa cttatttata    780
aaaacaaggg gaggctgggt ttagcctgtg ggccatagtt tgtcaaccac tggtgtaaaa    840
ccttagttat atatgatctg cattttcttg aactgatcat tgaaaactta taaacctaac    900
agaaaagcca cataatattt agtgtcatta tgcaataatc acattgcctt tgtgttaata    960
gtcaaatact tacctttgga gaatacttac ctttggagga atgtataaaa tttctcaggc   1020
agagtcctgg ataaggaaa aagtaattta tgaagtaaac ttcagttgct taatcaaact    1080
aatgatagtc taacaactga gcaagatcct catctgagag tgcttaaaat gggatcccca    1140
gagaccatta accaatactg gaactggtat ctagctactg atgtcttact ttgagtttat    1200
ttatgcttca gaatacagtt gtttgccctg tgcatgaata tacccatatt tgtgtgtgga    1260
tatgtgaagc ttttccaaat agagctctca gaagaattaa gtttttactt ctaattattt    1320
tgcattactt tgagttaaat ttgaatagag tattaaatat aaagttgtag attcttatgt    1380
gtttttgtat tagcccagac atctgtaatg ttttgcact ggtgacagac aaaatctgtt     1440
ttaaaatcat atccagcaca aaaactattt ctggctgaat agcacagaaa agtattttaa    1500
cctacctgta gagatcctcg tcatggaaag gtgccaaact gttttgaatg gaaggacaag   1560
taagagtgag gccacagttc ccaccacacg agggcttttg tattgttcta cttttcagc    1620 cctttacttt ctggctgaag catccccttg gagtgccatg tataagttgg gctattagag    1680
ttcatggaac atagaacaac catgaatgag tggcatgatc cgtgcttaat gatcaagtgt    1740
tacttatcta ataatcctct agaaagaacc ctgttagatc ttggtttgtg ataaaaatat    1800
```

-continued

```
aaagacagaa gacatgagga aaaacaaaag gtttgaggaa atcaggcata tgactttata    1860
cttaacatca gatcttttct ataatatcct actactttgg ttttcctagc tccataccac    1920
acacctaaac ctgtattatg aattacatat tacaaagtca taaatgtgcc atatggatat    1980
acagtacatt ctagttggaa tcgtttactc tgctagaatt taggtgtgag attttttgtt    2040
tcccaggtat agcaggctta tgtttggtgg cattaaattg gtttctttaa aatgctttgg    2100
tggcactttt gtaaacagat tgcttctaga ttgttacaaa ccaagcctaa gacacatctg    2160
tgaatactta gatttgtagc ttaatcacat tctagacttg tgagttgaat gacaaagcag    2220
ttgaacaaaa attatggcat ttaagaattt aacatgtctt agctgtaaaa atgagaaagt    2280
gttggttggt tttaaaatct ggtaactcca tgatgaaaag aaatttattt tatacgtgtt    2340
atgtctctaa taaagtattc atttgataaa aaaaaaaaaa aa                      2382
```

<210> SEQ ID NO 181
<211> LENGTH: 2377
<212> TYPE: DNA
<213> ORGANISM: Homo sapiens

<400> SEQUENCE: 181

```
atctttatgc aagacaagag tcagccatca gacactgaaa tatattatga tagattatga      60 agaatttttct ctgtagaatt atattcttcc tggaacctgg tagagtagat tagactcaaa     120 ggcttttttct tccttttctt actcctgttt tttccactca ctcttcccaa gagatttcct    180
aaagcttcaa gcttaataag cctaatagtg aaaaataact gaatttaatg gtataatgaa     240
gttcttcatt tccagacatc tttaattgat cttaaagctc atttgagtct ttgcccctga     300
acaaagacag acccattaaa atctaagaat tctaaatttt cacaactgtt tgagcttctt     360
ttcattttga aggatttgga atatatatgt tttcataaaa gtatcaagtg aaatatagtt     420
acatgggagc tcaatcatgt gcagattgca ttctgttatg ttgactcaat atttaattta     480
caactatcct tatttatatt gacctcaaga actccatttt atgcaatgca gaccactgag     540
atatagctaa cattctttca ataattttc cttttctttt ataattcctc tatagcaaat     600
ttttatgtat aactgattat acatatccat atttatattt cattgattcc aagacatcac     660
tttttcaatt taacatctct gaattgtga catttcttgc aactgttggc acttcagatg     720
cagtgtttaa aattatgctt gaataaatat tacactaatc caactttacc taaatgttta     780
tgcatctagg caaattttgt tttcttataa agatttgaga gcccatttat gacaaaatat     840
gaaggcgaaa tttaaggaca actgagtcac gcacaactca acatggagcc taactgatta     900
tcagctcaga tcccgcatat cttgagttta caaaagctct ttcaggtccc catttatact     960
ttacgtgagt gcgaatgatt tcagcaaacc ctaacttaac taacaagaat gggtaggtat     1020
gtctacgttt cattaacaaa ttttattat ttttattcta ttatatgaga tccttttata   1080
ttatcatctc acttttaaac aaaattaact ggaaaaatat tacatggaac tgtcatagtt    1140
aggttttgca gcatcttaca tgtcttgtat caatggcagg agaaaaatat gataaaaaca    1200
atcagtgctg tgaaaaacaa ctttcttcta gagtcctctt acttttttatt cttctttatc    1260 atttgtgggt ttttccccct tggctctcac tttaacttca agcttatgta acgactgtta    1320
taaaactgca tatttaaatt atttgaatta tatgaaataa ttgttcagct atctgggcag    1380
ctgttaatgt aaacctgaga gtaataacac tactctttta tctacctgga atacttttct    1440
gcataaaatt tatctttgta agctaactct attaatcagg tttcttctag cctctgcaac    1500
ctacttcagt tagaattgtc taatactgct ctattaatca ggtttctacc ctctacaacc    1560
```

```
tacttcagtt aaaattgtct aatacagcaa tatttaaaaa aaaaacactg caattgtcaa    1620
ggatggaaaa tgtgtgattt gtgtaaacaa ttttaccaa ctttacattt tcctacagat     1680
aaatgtgaaa ttttgataag aagtctacgc aatgacaagt acggtacata aattttatta    1740
agaatattga gtataaagta ctttaattct aaattataag aaaatataca tttgcacata    1800
ttaatataga aattcatttt gtgtatattt aacatagctt ttaaactatt ttacattagc    1860
tacttcatta tggtttcttg aacttctgaa aaaattaga aatgtattaa acttatcagt     1920
aacataaaaa cttattttgt ttcacctaac gaatactgcg tttgtaaaaa taaatttaat    1980
atagaatata tttttaaatt aaatatttga atataaaata gctctaagaa agaagcaaat    2040
tatcactgaa catatttctt attatttctg gctttgaatt atacgtaact taaattgtct    2100
taaatgatac agaatattgg agaatatgat actttcacat aatatactat gaacctgttc    2160
atataactct gattgactac taacttctgt tttatgtatt tattaaagag ctgacactgt    2220
agtttgtggt gagatgttta tttttctaac agagcttata acagttagga caaggcattt    2280
aattaatgca tcattctgtt tagtagtagg tgttaatcaa tatgaaattc tctgttttaa    2340
aataaaaatg taaaaatcta aaaaaaaaaa aaaaaa                              2377
```

<210> SEQ ID NO 182
<211> LENGTH: 1370
<212> TYPE: DNA
<213> ORGANISM: Homo sapiens

<400> SEQUENCE: 182

```
tgtgagcatg gtattttgtc tcggaagaaa aaaatatggg tcaggcgcaa agtaagccca      60
ccccactggg aactatgtta aaaaaaaatt tcaagattta agggagatta cggtgttact     120
atgacaccag aaaaacttag aactttgtgt gaaatagact ggctaacatt agaggtgggt     180
tggctatcag aagaaagcct ggagaggtcc cttgtttcaa aggtatggca caaggtaacc    240
tgtaagccaa agcacccgga ccagtttcta tacatagaca gttacagctg gtttagaccc    300 cttcccctc tccccacagt agttaagaga acagcagcat aagcagctgg cagaggcaag     360
gaaagaccag cagagagaaa aaaaggccat ctataccaat tttaagttaa tttagactga    420
acaagggctt attaatagca aaggataatt gaaatcacaa acttataagg gtttcaacaa    480
aagtgaagtt tgctaaaagt taacagtgta acatgtatta tggtaacttc taatcttgtg    540
gccttagaca gtctagtcaa aacacataaa gaaagtttgc tttaaaaaaa caatggttat    600
cttcaaaaat aaaggggaga ggcagaattt atataaaaag agttatatga taaattcttg    660
tcctgaaata aattaactgg ttgtttaaag aaaagaatgt ttgtaataag tcaaaaagtt    720
aaaacatgtt taaaaaattg tctgcaaaag tcataaaaga aaaattttta ttaaaaaaat   780
tttaagcaaa aaatgttgta taatttaaaa gtaataaggc ctcctgtgta ctattaagac    840
agatgcaaat tcctggttga aatggatcaa atattccatc tgcacattaa acaaaagcaa    900
ttgttatgct tgtgcacatg gcaggccaga ggccctgatt gtcccccttc cactaaggtg    960
gtcctctagt cgaccaggcg tggactgcat ggtagctctt ttccaggatt ctacagcctg   1020
gagtaataag tcatgccaag ctctctctgc tatatcccaa agtctctgcg ggtcagcccc    1080
caagggccat gcagcttctg tctcccaaca ctaagttcac ttcgtgtctc tcacggcaga    1140
gaggaaactt agtattcctt ggagacctga agggatgcag tgagcttaag aattttcaag    1200
agcttatcaa tcagtcagcc cttgttcatc cccgagtgga tgtgtggtgg tattgtggtg    1260
```

-continued

| | |
|---|---|
| gacctttact gggcactctg ccaaataact agtgtggcac ttgtgcttta gtccatttgg | 1320 |
| ctatcccttt caccctggca tttcatcaac caaaaaaaaa aaaaaaaaaa | 1370 |

<210> SEQ ID NO 183
<211> LENGTH: 2060
<212> TYPE: DNA
<213> ORGANISM: Homo sapiens
<220> FEATURE:
<221> NAME/KEY: misc_feature
<222> LOCATION: (1)...(2060)
<223> OTHER INFORMATION: n=A,T,C or G

<400> SEQUENCE: 183

| | |
|---|---|
| gtttcagggg aggagacaag gtttcttgtt tgccgtatat gctcctgcag agaagaggaa | 60 |
| gtgaccgtgg aggccatctg gccctgtgtt ttgatatggc aaaattaatg aatgcaatca | 120 |
| gaagaccttt gagcaagaaa gtaccctgga acaacccaat ttggactgca agtattagtt | 180 |
| gggtcttcca ggtgcctctc acagcagcag tcatggcagc agtgactcta gccatgtcca | 240 |
| tgaccaactg ctgcataaca aatagccccg agactcagca gcttacaaca gggtccccag | 300 |
| cccacagact ggcactggtc catggcttgt taggaacctg actgcgcagc agaaggtgag | 360 |
| tgagcattac tgcctgagct ctgcctcctg tcagatcatc aggggcatta gattctcata | 420 |
| ggagcgtgaa cccattgca aaccgcgcat gcgaaggatg tacgttgcgt gctccttatg | 480 |
| agaatctaac taatgcctga tgatttgagg tggggcagtt tcatccccaa accatctctc | 540 |
| tcccttcatg tccatggaaa aattgtcttc tacaaaacca gtccgtggtg ccaaaaaggt | 600 |
| tggagactgc tggtttacaa ccgcaatgaa cattcatcat cccacacagt gtcagagggt | 660 |
| cgggaacacg ggtgccctgc ctgtgtgctt ccggttccag atttctcagt gggttgtgat | 720 |
| caaggtatca gcggaggccg tattcatctg caagcttgac caggaataga agagccactt | 780 |
| catgggtggc tcactcagat gccagcaggt cagtgctggt ggctggcagg cagcctcagc | 840 |
| tcctcacctc atggatctct cctgagcaca gttttcctgt ccttacaacc tggtagctgg | 900 |
| cttctccaga gcaggtgact caggagagga caaggtgaga gcccagcacc ttatggtcta | 960 |
| gtctcagaag tcacacgcca tcatttctgc aatgtcattt tggggttcca ggtcagctgt | 1020 |
| atcactgtgg gaggtgagta tatagatgtc ctagaccatt caggctgcta tgacagaaca | 1080 |
| ccatgaactg agtggctcat gaacaacaga aatttcccac agttctgtag ctgggaaat | 1140 |
| ccaagatcaa ggtggcagca ggttcagcgt ctgctaagct cctgcttttc atggattgca | 1200 |
| tcttctcact gtgtcctcac gtgatggaca gagcaaatga gctctcaggc actagtccca | 1260 |
| gccatgagga ctctgctttc atgactcatc actccgcaaa ggcccacctc catcagaaga | 1320 |
| cagctgctaa ctgcagctgc catcctccaa gacgggagac acagaattgg gggacatata | 1380 |
| cattgagatc tgaaaggcct ggacagcaac aggtggggat cgtgggggca tcttggaggg | 1440 |
| tggctgccgc agtaacattt ctgacccatg ctttctgctt gcactcatct cctgcctttg | 1500 |
| atcttcatta tctcargcag tccccacaac gactgtatct aggagttcat tttaccctca | 1560 |
| ttttacagat gaaacgtctc agagggtaat gtgcttgccc agtgtctcac aaatgcaaag | 1620 |
| tcactgaggt aggatttcaa cctaggtcca atcatctctg cagcattagg ggttcaccat | 1680 |
| tgccatagac ttaactgtgt cccccaaaat ttgtatgttg aagccctacc agcctccccc | 1740 |
| ccccaatgtg ctgatgtttg gagaaagggc ctttgggagg taattaggtt tagatgagat | 1800 |
| catgagggtg ggactctcat aatggcatta atgccatcag gtgaagagat accagagacc | 1860 |
| ttgtgtcctc tctctctgca atgtgaggac acagtgagaa ggcagctgtc tgcaagctgg | 1920 |

```
gaagagagta ctgaccagga acttaatcag agggcatctt gatcttggac ttcccagcct    1980
ccagaactct gaaaagttaa tgnctattat ttaagccacg cagtctatgg aattttgtta    2040
gagccaaccc caagcttact                                                2060

<210> SEQ ID NO 184
<211> LENGTH: 3079
<212> TYPE: DNA
<213> ORGANISM: Homo sapiens

<400> SEQUENCE: 184
ggcacaaagt tggggccgc gaagatgagg ctgtccccgg cgcccctgaa gctgagccgg      60
actccggcac tgctggccct ggcgctgccc ctggccgcgg cgctggcctt ctccgacgag    120
accctggaca aagtgcccaa gtcagagggc tactgtagcc gtatcctgcg cgcccagggc    180
acgcggcgcg agggctacac cgagttcagc ctccgcgtgg agggcgaccc cgacttctac    240
aagccgggaa ccagctaccg cgtaacactt tcagctgctc ctccctccta cttcagagga    300
ttcacattaa ttgccctcag agaacagaga gaggtgata aggaagaaga ccatgctggg    360
accttccaga tcatagacga agaagaaact cagtttatga gcaattgccc tgttgcagtc    420
actgaaagca ctccacggag gaggacccgg atccaggtgt tttggatagc accaccagcg    480
ggaacaggct gcgtgattct gaaggccagc atcgtacaaa aacgcattat ttattttcaa    540
gatgagggct ctctgaccaa gaaactttgt gaacaagatt ccacatttga tggggtgact    600
gacaaaccca tcttagactg ctgtgcctgc ggaactgcca agtacagact cacattttat    660
gggaattggt ccgagaagac acacccaaag gattaccctc gtcgggccaa ccactggtct    720
gcgatcatcg gaggatccca ctccaagaat tatgtactgt gggaatatgg aggatatgcc    780
agcgaaggct caaacaagt tgcagaattg ggctcacccg tgaaaatgga ggaagaaatt    840
cgacaacaga gtgatgaggt cctcaccgtc atcaaagcca agcccaatg ccagcctgg    900 cagcctctca acgtgagagc agcaccttca gctgaatttt ccgtggacag aacgcgccat    960
ttaatgtcct tcctgaccat gatgggccct agtcccgact ggaacgtagg cttatctgca   1020
gaagatctgt gcaccaagga atgtggctgg gtccagaagg tggtgcaaga cctgattccc   1080
tgggacgctg gcaccgacag cggggtgacc tatgagtcac ccaacaaacc caccattccc   1140
caggagaaaa tccggcccct gaccagcctg gaccatcctc agagtccttt ctatgaccca   1200
gagggtgggt ccatcactca agtagccaga gttgtcatcg agagaatcgc acggaagggt   1260
gaacaatgca atattgtacc tgacaatgtc gatgatattg tagctgacct ggctccagaa   1320
gagaaagatg aagatgacac ccctgaaacc tgcatctact ccaactggtc cccatggtcc   1380
gcctgcagct cctccacctg tgacaaaggc aagaggatgc gacagcgcat gctgaaagca   1440
cagctggacc tcagcgtccc ctgccctgac acccaggact tccagccctg catgggccct   1500
ggctgcagtg acgaagacgg ctccacctgc accatgtccg agtggatcac ctggtcgccc   1560
tgcagcatct cctgcggcat gggcatgagg tcccgggaga ggtatgtgaa gcagttcccg   1620
gaggacggct ccgtgtgcac gctgcccact gaggaaatgg agaagtgcac ggtcaacgag   1680
gagtgctctc ccagcagctg cctgatgacc gagtggggcg agtgggacga gtgcagcgcc   1740
acctgcggca tgggcatgaa gaagcggcac cgcatgatca agatgaaccc cgcagatggc   1800
tccatgtgca aagccgagac atcacaggca gagaagtgca tgatgccaga gtgccacacc   1860
atcccatgct tgctgtcccc atggtccgag tggagtgact gcagcgtgac ctgcgggaag   1920
```

-continued

| | |
|---|---|
| ggcatgcgaa cccgacagcg gatgctcaag tctctggcag aacttggaga ctgcaatgag | 1980 |
| gatctggagc aggtggagaa gtgcatgctc cctgaatgcc ccattgactg tgagctcacc | 2040 |
| gagtggtccc agtggtcgga atgtaacaag tcatgtggga aaggccacgt gattcgaacc | 2100 |
| cggatgatcc aaatggagcc tcagtttgga ggtgcaccct gcccagagac tgtgcagcga | 2160 |
| aaaaagtgcc gcatccgaaa atgccttcga atccatccca tccaaaagcc acgctggagg | 2220 |
| gaggcccgag agagccggcg gagtgagcag ctgaaggaag agtctgaagg ggagcagttc | 2280 |
| ccaggttgta ggatgcgccc atggacggcc tggtcagaat gcaccaaact gtgcggaggt | 2340 |
| ggaattcagg aacgttacat gactgtaaag aagagattca aaagctccca gtttaccagc | 2400 |
| tgcaaagaca agaaggagat cagagcatgc aatgttcatc cttgttagca agggtacgag | 2460 |
| ttccccaggg ctgcactcta gattccagag tcaccaatgg ctggattatt gcttgtttta | 2520 |
| agacaattta aattgtgtac gctagttttc atttttgcag tgtggttcgc ccagtagtct | 2580 |
| tgtggatgcc agagacatcc tttctgaata cttcttgatg ggtacaggct gagtggggcg | 2640 |
| ccctcacctc cagccagcct cttcctgcag aggagtagtg tcagccacct tgtactaagc | 2700 |
| tgaaacatgt ccctctggag cttccacctg gccaggagg acgagactt tgacctactc | 2760 |
| cacatggaga ggcaaccatg tctggaagtg actatgcctg agtcccaggg tgcggcaggt | 2820 |
| aggaaacatt cacagatgaa gacagcagat tccccacatt ctcatctttg gcctgttcaa | 2880 |
| tgaaaccatt gtttgcccat ctcttcttag tggaacttta ggtctctttt caagtctcct | 2940 |
| cagtcatcaa tagttcctgg ggaaaaacag agctggtaga cttgaagagg agcattgatg | 3000 |
| ttgggtggct tttgttcttt cactgagaaa ttcggaatac atttgtctca ccctgatat | 3060 |
| tggttcctga tgccccagc | 3079 |

<210> SEQ ID NO 185
<211> LENGTH: 3000
<212> TYPE: DNA
<213> ORGANISM: Homo sapiens

<400> SEQUENCE: 185

| | |
|---|---|
| gtttcagggg aggagacaag gtttcttgtt tgccgtatat gctcctgcag agaagaggaa | 60 |
| gtgaccgtgg aggccatctg gccctgtgtt ttgatatggc aaaattaatg aatgcaatca | 120 |
| gaagaccttt gagcaagaaa gtaccctgga acaacccaat ttggactgca agtattagtt | 180 |
| gggtcttcca ggtgcctctc acagcagcag tcatggcagc agtgactcta gccatgtcca | 240 |
| tgaccaactg ctgcataaca aatagccccg agactcagca gcttacaaca gggtccccag | 300 |
| cccacagact ggcactggtc catggcttgt taggaacctg actgcgcagc agaaggtgag | 360 |
| tgagcattac tgcctgagct ctgcctcctg tcagatcatc aggggcatta gattctcata | 420 |
| ggagcgtgaa ccctattgca aaccgcgcat gcgaaggatg tacgttgcgt gctccttatg | 480 |
| agaatctaac taatgcctga tgatttgagg tgggggcagtt tcatccccaa accatctctc | 540 |
| tcccttcatg tccatggaaa aattgtcttc tacaaaacca gtccgtggtg ccaaaaaggt | 600 |
| tggagactgc tggtttacaa ccgcaatgaa cattcatcat cccacacagt gtcagagggt | 660 |
| cgggaacacg ggtgccctgc ctgtgtgctt ccggttccag atttctcagt gggttgtgat | 720 |
| caaggtatca gcggaggccg tattcatctg caagcttgac caggaataga agagccactt | 780 |
| catgggtggc tcactcagat gccagcaggt cagtgctggt ggctggcagg cagcctcagc | 840 |
| tcctcacctc atggatctct cctgagcaca gttttcctgt ccttacaacc tggtagctgg | 900 |
| cttctccaga gcaggtgact caggagagga caaggtgaga gccacagcac cttatggtct | 960 |

```
agtctcagaa gtcacacgcc atcatttctg caatgtcatt ttggggttcc aggtcagctg    1020
tatcactgtg ggaggtgagt atatagatgt cctagaccat tcaggctgct atgacagaac    1080
accatgaact gagtggctca tgaacaacag aaatttccca cagttctgta ggctgggaaa    1140
tccaagatca aggtggcagc aggttcagcg tctgctaagc tcctgctttt catggattgc    1200
atcttctcac tgtgtcctca cgtgatggac agagcaaatg agctctcagg cactagtccc    1260
agccatgagg actctgcttt catgactcat cactccgcaa aggcccacct ccatcagaag    1320
acagctgcta actgcagctg ccatcctcca agacgggaga cacagaattg ggggacatat    1380
acattgagat ctgaaaggcc tggacagcaa caggtgggga tcgtggggc atcttggagg     1440 gtggctgccg cagtaacatt tctgacccat gctttctgct tgcactcatc tcctgccttt    1500
gatcttcatt atctcaggca gtccccacaa cgactgtatc taggagttca ttttacccctc   1560 attttacaga tgaaacgtct cagagggtaa tgtgcttgcc cagtgtctca caaatgcaaa    1620
gtcactgagg taggatttca acctaggtcc aatcatctct gcagcattag gggttcacca    1680
ttgccataga cttaactgtg tcccccaaaa tttgtatgtt gaagccctac cagcctcccc     1740
cccccaatgt gctgatgttt ggagaaaggg cctttgggag gtaattaggt ttagatgaga    1800
tcatgagggt gggactctca taatggcatt aatgccatca ggtgaagaga taccagagac    1860
cttgtgtcct ctctctctgc aatgtgagga cacagtgaga aggcagctgt ctgcaagctg    1920
ggaagagagt actgaccagg aacttaatca gagggcatct tgatcttgga cttcccagcc    1980
tccagaactc tgaaaagtta atgtctatta tttaagccac gcagtctatg gaattttgtt    2040
agagccaacc caagcttact aagataatca gtatgctgca ctttctataa atgtaatttt    2100
tacatttata aaacaaaac aagagatttg ctgctctata caactgtac ctacattgta      2160 gatgaataa caaatctaca tacagattta gtaatctcta tgtagatata gaacatagtg     2220
tatctaatag agacatagtg tctgtggtct gatgttaatt ttaggaatta gccgtcactg    2280
attgggcctt gtccaggtat tcttctccct tgtcctggct ctgtaaccta gttatccttg    2340
tctttgctaa cccataacca actattgtat caggactatt atgccactac agatgatgca    2400
gtttgggttt actgtttctc accatttaga caatacttca tcaaatatat ttctgtatga    2460
ctttagtgat atcagttttt gattcattcc tgcatagatc tgggcaaatt gtagacctta    2520
ggaggtgtat tcaccatcca gttctctgga actgcttatg acattttttct ctgagctttc   2580 ttgtcccaaa aggagccttc ctaaaatagt ctttaagtgc ctttaaaaag agaaagagaa    2640
attaagagaa aaaaacccc aaactcattc ctttactctg atgtgacagt cctcccagga     2700
cactgcagtg gcctgagttt tgctgttaat ttcattcact tatgtttggg ctatgtaaat    2760
tctgcctaga gctggaatgt cattatgtaa agaaatattt tttgtttata ttctttaata   2820
gtaccagtaa tgtatatctt attcagcttc gagaatataa ttgggttgtt tataaaaacc    2880
acacatcatc aaactcacat tgtaacgatt atttcacttt tcaaaaaaaa tggcattaga    2940
aaaacttgaa tgatgttagt tatcttaaag aagtgtgtac tatgtttaaa aaaaaaaaa    3000
```

<210> SEQ ID NO 186
<211> LENGTH: 807
<212> TYPE: PRT
<213> ORGANISM: Homo sapiens

<400> SEQUENCE: 186

```
Met Arg Leu Ser Pro Ala Pro Leu Lys Leu Ser Arg Thr Pro Ala Leu
                 5                  10                  15
```

-continued

Leu Ala Leu Ala Leu Pro Leu Ala Ala Leu Ala Phe Ser Asp Glu
            20                  25                  30

Thr Leu Asp Lys Val Pro Lys Ser Glu Gly Tyr Cys Ser Arg Ile Leu
            35                  40                  45

Arg Ala Gln Gly Thr Arg Arg Glu Gly Tyr Thr Glu Phe Ser Leu Arg
        50                  55                  60

Val Glu Gly Asp Pro Asp Phe Tyr Lys Pro Gly Thr Ser Tyr Arg Val
65                  70                  75                  80

Thr Leu Ser Ala Ala Pro Pro Ser Tyr Phe Arg Gly Phe Thr Leu Ile
                85                  90                  95

Ala Leu Arg Glu Asn Arg Glu Gly Asp Lys Glu Glu Asp His Ala Gly
            100                 105                 110

Thr Phe Gln Ile Ile Asp Glu Glu Thr Gln Phe Met Ser Asn Cys
            115                 120                 125

Pro Val Ala Val Thr Glu Ser Thr Pro Arg Arg Thr Arg Ile Gln
        130                 135                 140

Val Phe Trp Ile Ala Pro Pro Ala Gly Thr Gly Cys Val Ile Leu Lys
145                 150                 155                 160

Ala Ser Ile Val Gln Lys Arg Ile Ile Tyr Phe Gln Asp Glu Gly Ser
            165                 170                 175

Leu Thr Lys Lys Leu Cys Glu Gln Asp Ser Thr Phe Asp Gly Val Thr
            180                 185                 190

Asp Lys Pro Ile Leu Asp Cys Cys Ala Cys Gly Thr Ala Lys Tyr Arg
            195                 200                 205

Leu Thr Phe Tyr Gly Asn Trp Ser Glu Lys Thr His Pro Lys Asp Tyr
        210                 215                 220

Pro Arg Arg Ala Asn His Trp Ser Ala Ile Ile Gly Gly Ser His Ser
225                 230                 235                 240

Lys Asn Tyr Val Leu Trp Glu Tyr Gly Gly Tyr Ala Ser Glu Gly Val
            245                 250                 255

Lys Gln Val Ala Glu Leu Gly Ser Pro Val Lys Met Glu Glu Glu Ile
            260                 265                 270

Arg Gln Gln Ser Asp Glu Val Leu Thr Val Ile Lys Ala Lys Ala Gln
        275                 280                 285

Trp Pro Ala Trp Gln Pro Leu Asn Val Arg Ala Ala Pro Ser Ala Glu
        290                 295                 300

Phe Ser Val Asp Arg Thr Arg His Leu Met Ser Phe Leu Thr Met Met
305                 310                 315                 320

Gly Pro Ser Pro Asp Trp Asn Val Gly Leu Ser Ala Glu Asp Leu Cys
            325                 330                 335

Thr Lys Glu Cys Gly Trp Val Gln Lys Val Val Gln Asp Leu Ile Pro
            340                 345                 350

Trp Asp Ala Gly Thr Asp Ser Gly Val Thr Tyr Glu Ser Pro Asn Lys
        355                 360                 365

Pro Thr Ile Pro Gln Glu Lys Ile Arg Pro Leu Thr Ser Leu Asp His
        370                 375                 380

Pro Gln Ser Pro Phe Tyr Asp Pro Glu Gly Gly Ser Ile Thr Gln Val
385                 390                 395                 400

Ala Arg Val Val Ile Glu Arg Ile Ala Arg Lys Gly Glu Gln Cys Asn
            405                 410                 415

Ile Val Pro Asp Asn Val Asp Asp Ile Val Ala Asp Leu Ala Pro Glu
            420                 425                 430

```
Glu Lys Asp Glu Asp Thr Pro Glu Thr Cys Ile Tyr Ser Asn Trp
        435                 440                 445

Ser Pro Trp Ser Ala Cys Ser Ser Thr Cys Asp Lys Gly Lys Arg
        450                 455                 460

Met Arg Gln Arg Met Leu Lys Ala Gln Leu Asp Leu Ser Val Pro Cys
465                 470                 475                 480

Pro Asp Thr Gln Asp Phe Gln Pro Cys Met Gly Pro Gly Cys Ser Asp
                485                 490                 495

Glu Asp Gly Ser Thr Cys Thr Met Ser Glu Trp Ile Thr Trp Ser Pro
            500                 505                 510

Cys Ser Ile Ser Cys Gly Met Gly Met Arg Ser Arg Glu Arg Tyr Val
        515                 520                 525

Lys Gln Phe Pro Glu Asp Gly Ser Val Cys Thr Leu Pro Thr Glu Glu
        530                 535                 540

Met Glu Lys Cys Thr Val Asn Glu Glu Cys Ser Pro Ser Ser Cys Leu
545                 550                 555                 560

Met Thr Glu Trp Gly Glu Trp Asp Glu Cys Ser Ala Thr Cys Gly Met
                565                 570                 575

Gly Met Lys Lys Arg His Arg Met Ile Lys Met Asn Pro Ala Asp Gly
            580                 585                 590

Ser Met Cys Lys Ala Glu Thr Ser Gln Ala Glu Lys Cys Met Met Pro
        595                 600                 605

Glu Cys His Thr Ile Pro Cys Leu Leu Ser Pro Trp Ser Glu Trp Ser
        610                 615                 620

Asp Cys Ser Val Thr Cys Gly Lys Gly Met Arg Thr Arg Gln Arg Met
625                 630                 635                 640

Leu Lys Ser Leu Ala Glu Leu Gly Asp Cys Asn Glu Asp Leu Glu Gln
                645                 650                 655

Val Glu Lys Cys Met Leu Pro Glu Cys Pro Ile Asp Cys Glu Leu Thr
            660                 665                 670

Glu Trp Ser Gln Trp Ser Glu Cys Asn Lys Ser Cys Gly Lys Gly His
        675                 680                 685

Val Ile Arg Thr Arg Met Ile Gln Met Glu Pro Gln Phe Gly Gly Ala
        690                 695                 700

Pro Cys Pro Glu Thr Val Gln Arg Lys Lys Cys Arg Ile Arg Lys Cys
705                 710                 715                 720

Leu Arg Asn Pro Ser Ile Gln Lys Pro Arg Trp Arg Glu Ala Arg Glu
                725                 730                 735

Ser Arg Arg Ser Glu Gln Leu Lys Glu Glu Ser Glu Gly Glu Gln Phe
            740                 745                 750

Pro Gly Cys Arg Met Arg Pro Trp Thr Ala Trp Ser Glu Cys Thr Lys
        755                 760                 765

Leu Cys Gly Gly Gly Ile Gln Glu Arg Tyr Met Thr Val Lys Lys Arg
        770                 775                 780

Phe Lys Ser Ser Gln Phe Thr Ser Cys Lys Asp Lys Lys Glu Ile Arg
785                 790                 795                 800

Ala Cys Asn Val His Pro Cys
                805

<210> SEQ ID NO 187
<211> LENGTH: 892
<212> TYPE: DNA
<213> ORGANISM: Homo sapiens

<400> SEQUENCE: 187
```

```
tttattgatg tttcaacagg cacttattca aataagttat atatttgaaa acagccatgg    60
taagcatcct tggcttctca cccattcctc atgtggcatg ctttctagac tttaaaatga   120
ggtaccctga atagcactaa gtgctctgta agctcaagga atctgtgcag tgctacaaag   180
cccacaggca gagaaagaac tcctcaagtg cttgtggtca gagactaggt tccatatgag   240
gcacacctat gatgaaggtc ttcacctcca gaaggtgaca ctgttcagag atcctcattt   300
cctggagagt gggagaaaat ccctcctttg ggaaatccct tttcccagca gcagagccca   360
cctcattgct tagtgatcat ttggaaggca ctgagagcct tcaggggctg acagcagaga   420
aatgaaaatg agtacagttc agatggtgga agaagcatgg cagtgacatc ttccatgctc   480
tttttctcag tgtctgcaac tccaaagatc aaggccataa cccaggagac catcaacgga   540
agattagttc tttgtcaagt gaatgaaatc caaaagcacg catgagacca atgaaagttt   600
ccgcctgttg taaaatctat ttccccccaa ggaaagtcct tgcacagaca ccagtgagtg   660
agttctaaaa gatacccttg gaattatcag actcagaaac ttttattttt tttttctgta   720
acagtctcac cagacttctc ataatgctct taatatattg cacttttcta atcaaagtgc   780
gagtttatga gggtaaagct ctactttcct actgcagcct tcagattctc atcattttgc   840
atctattttg tagccaataa aactccgcac tagcaaaaaa aaaaaaaaaa aa            892

<210> SEQ ID NO 188
<211> LENGTH: 1448
<212> TYPE: DNA
<213> ORGANISM: Homo sapiens
<220> FEATURE:
<221> NAME/KEY: misc_feature
<222> LOCATION: (1)...(1448)
<223> OTHER INFORMATION: n = A,T,C or G

<400> SEQUENCE: 188
tgtgactcac atttctttta ctgtgacaca ataatgtgat cctaaaactg gcttatcctt    60
gagtgtttac aactcaaaca acttttttgaa tgcagtagtt ttttttttttt aaaaacaaac   120 ttttatgtca aattttttttt cttagaagta gtcttcatta ttataaattt gtacaccaaa   180
aggccatggg gaactttgtg caagtacctc atcgctgagc aaatggagct tgctatgttt   240
taatttcaga aaatttcctc atatacgtag tgtgtagaat caagtctttt aataattcat   300
tttttcttca taatatttac tcaaagttaa gcttaaaaat aagttttatc ttaaaatcat   360
atttgaagac agtaagacag taaactattt taggaagtca accccattg cactctgtgg    420 cagttattct ggtaaaaata ggcaaaagtg acctgaatct acaatggtgt cccaaagtaa   480
ccaagtaaga gagattgtaa atgataaacc gagctttaaa ggataaagtg ttaataaaga   540
aaggaagctg ggcacatgtc aaaaagggag atcgaaatgt taggtaatca tttagaaagg   600
acagaaaata tttaaagtgg ctcataggta atgaatattt ctgacttaga tgtaaatcca   660
tctggaatct ttacatcctt tgccagctga aacaagaaag tgaagggaca atgatatttc   720
atggtcagtt tattttgtaa gagacagaag aaattatatc tatacattac cttgtagcag   780
cagtacctgg aagccccagc ccgtcacaga agtgtggagg ggggctcctg actagacaat   840
ttccctagcc cttgtgattt gaagcatgaa agttctggca ggttatgagc agcactaggg   900
ataaagtatg gtttatttttt ggtgtaattt aggttttttca acaaagccct tgtctaaaat   960
aaaaggcatt attggaaata tttgaaaact agaaaatgat ggataaaagg gctgataaga  1020
aaatttctga ctgtcagtag aagtgagata agatcctcag aggaaacagt aagaagggat  1080
```

```
aatcattaag ataqtaaaac aggcaaagca gaatcacatg tgcncacaca catacacatg      1140
taaacattgg aatgcataag ttttaatatt ttagcgctat cagtttctaa atgcattaat      1200
tactaactgc cctctcccaa gattcattta gttcaaacag tatccgtaaa ctaggaataa      1260
tgccacatgc attcaatggg atcttttaag tactcttcag tttgttccaa gaaatgtgcc      1320
tactgaaatc aaattaattt gtattcaatg tgtacttcaa gactgctaat tgtttcatct      1380
gaaagcctac aatgaatcat tgttcamcct tgaaaaataa aattttgtaa atcaaaaaaa      1440
aaaaaaaa                                                              1448

<210> SEQ ID NO 189
<211> LENGTH: 460
<212> TYPE: DNA
<213> ORGANISM: Homo sapiens

<400> SEQUENCE: 189
ttttgggagc acggactgtc agttctctgg gaagtggtca gcgcatcctg cagggcttct       60
cctcctctgt cttttggaga accagggctc ttctcagggg ctctagggac tgccaggctg      120
tttcagccag gaaggccaaa atcaagagtg agatgtagaa agttgtaaaa tagaaaaagt      180
ggagttggtg aatcggttgt tctttcctca catttggatg attgtcataa ggttttttagc     240 atgttcctcc ttttcttcac cctccccttt tttcttctat taatcaagag aaacttcaaa      300
gttaatggga tggtcggatc tcacaggctg agaactcgtt cacctccaag catttcatga      360
aaaagctgct tcttattaat catacaaact ctcaccatga tgtgaagagt ttcacaaatc      420
cttcaaaata aaaagtaatg acttaaaaaa aaaaaaaaaa                            460

<210> SEQ ID NO 190
<211> LENGTH: 481
<212> TYPE: DNA
<213> ORGANISM: Homo sapiens

<400> SEQUENCE: 190
aggtggtgga agaaactgtg gcacgaggtg actgaggtat ctgtgggagc taatcctgtc       60
caggtggaag taggagaatt tgatgatggt gcagaggaaa ccgaagagga ggtggtggcg      120
gaaaatccct gccagaacca ccactgcaaa cacggcaagg tgtgcgagct ggatgagaac      180
aacaccccca tgtgcgtgtg ccaggacccc accagctgcc cagcccccat tggcgagttt      240
gagaaggtgt gcagcaatga caacaagacc ttcgactctt cctgccactt ctttgccaca      300
aagtgcaccc tggagggcac caagaagggc cacaagctcc acctggacta catcgggcct      360
tgcaaataca tccccccttg cctggactct gagctgaccg aattccccct gcgcatgcgg      420
gactggctca agaacgtcct ggtcaccctg tatgagaggg atgaggacaa caaccttctg      480
a                                                                     481

<210> SEQ ID NO 191
<211> LENGTH: 489
<212> TYPE: DNA
<213> ORGANISM: Homo sapiens
<220> FEATURE:
<221> NAME/KEY: misc_feature
<222> LOCATION: (1)...(489)
<223> OTHER INFORMATION: n = A,T,C or G

<400> SEQUENCE: 191
atataaatta gactaagtgt tttcaaataa atctaaatct tcagcatgat gtgttgtgta       60
taattggagt agatattaat taagtcccct gtataatgtt ttgtaatttt gcaaaacata     120
```

```
tcttgagttg tttaaacagt caaaatgttt gatattttat accagcttat gagctcaaag      180
tactacagca aagcctagcc tgcatatcat tcacccaaaa caaagtaata gcgcctcttt      240
tattattttg actgaatgtt ttatggaatt gaaagaaaca tacgttcttt tcaagacttc      300
ctcatgaatc tntcaattat aggaaaagtt attgtgataa aataggaaca gctgaaagat      360
tgattaatga actattgtta attcttccta ttttaatgaa tgacattgaa ctgaattttt      420
tgtctgttaa atgaacttga tagctaataa aagncaact agccatcaaa aaaaaaaaa      480 aaaaaaaaa                                                               489

<210> SEQ ID NO 192
<211> LENGTH: 516
<212> TYPE: DNA
<213> ORGANISM: Homo sapiens

<400> SEQUENCE: 192
acttcaaagc cagctgaagg aaagaggaag tgctagagag agccccttc agtgtgcttc        60 tgacttttac ggacttggct tgttagaagg ctgaaagatg atggcaggaa tgaaaatcca      120
gcttgtatgc atgctactcc tggctttcag ctcctggagt ctgtgctcag attcagaaga      180
ggaaatgaaa gcattagaag cagatttctt gaccaatatg catacatcaa agattagtaa      240
agcacatgtt ccctcttgga agatgactct gctaaatgtt tgcagtcttg taaataattt      300
gaacagccca gctgaggaaa caggagaagt tcatgaagag gagcttgttg caagaaggaa      360
cttcttactg ctttagatgg ctttagcttg gaagcaatgt tgacaatata ccagctccac      420
aaaatctgtc acagcagggc ttttcaacac tgggagttaa tccaggaaga tattcttgat      480
actggaaatg acaaaaatgg aaaggaagaa gtcata                                516

<210> SEQ ID NO 193
<211> LENGTH: 1409
<212> TYPE: DNA
<213> ORGANISM: Homo sapiens

<400> SEQUENCE: 193
tgattctttt ccaaaacttt tagccatagg gtcttttata gacagggata gtaaaatgaa       60
aattgagaaa tataagatga aaaggaatgg taaaaatatc ttttaggggg cttttaattg      120
gtgatctgaa atcttgggag aagctgttct tttcaggcct gaggtgctct tgactgtcgc      180
ctgcgcactg tgtaccccga gcaacattct aagggtgtgc tttcgccttg gctaactcct      240
ttgacctcat tcttcatata gtagtctagg aaaaagttgc aggtaattta aactgtctag      300
tggtacatag taactgaatt tctattccta tgagaaatga gaattattta tttgccatca      360
acacatttta tactttgcat ctccaaattt attgcggcga gacttgtcca ttgtgaaagt      420
tagagaacat tatgtttgta tcatttcttt cataaaacct caagagcatt tttaagcccc      480
tttcatcaga cccagtgaaa actaaggata gatgtttttt aactggaggt ctcctgataa      540
ggagaacaca atccaccatt gtcatttaag taataagaca ggaaattgac cttgacgctt      600
tcttgttaaa tagatttaac aggaacatct gcacatcttt tttccttgtg cactatttgt      660
ttaattgcag tggattaata cagcaagagt gccacattat aactaggcaa ttatccattc      720
ttcaagactt agttattgtc acactaattg atcgtttaag gcataagatg gtctagcatt      780
aggaacatgt gaagctaatc tgctcaaaaa gatcaacaaa ttaatattgt tgctgatatt      840
tgcataattg gctgcaatta tttaatgttt aattgggttg atcaaatgag attcagcaat      900
```

-continued

| | |
|---|---|
| tcacaagtgc attaatataa acagaactgg ggcacttaaa atgataatga ttaacttata | 960 |
| ttgcatgttc tcttcctttc acttttttca gtgtctacat ttcagaccga gtttgtcagc | 1020 |
| tttttttgaaa acacatcagt agaaaccaag attttaaaat gaagtgtcaa gacgaaggca | 1080 |
| aaacctgagc agttcctaaa aagatttgct gttagaaatt ttctttgtgg cagtcattta | 1140 |
| ttaaggattc aactcgtgat acaccaaaag aagagttgac ttcagagatg tgttccatgc | 1200 |
| tctctagcac aggaatgaat aaatttataa cacctgcttt agcctttgtt ttcaaaagca | 1260 |
| caaaggaaaa gtgaaaggga aagagaaaca agtgactgag aagtcttgtt aaggaatcag | 1320 |
| gtttttttcta cctggtaaac attctctatt cttttctcaa aagattgttg taagaaaaaa | 1380 |
| tgtaagmcaa aaaaaaaaaa aaaaaaaaa | 1409 |

<210> SEQ ID NO 194
<211> LENGTH: 441
<212> TYPE: DNA
<213> ORGANISM: Homo sapiens

<400> SEQUENCE: 194

| | |
|---|---|
| cagatttcgg tagccatctc cctccaaata tgtctctttc tgctttctta gtgcccatta | 60 |
| tttccccttc tcctttcttc tgtcactgcc atctccttct tggtcttccc attgttcttt | 120 |
| aactggccgt aatgtggaat tgatatttac attttgatac ggttttttttc ttggcctgtg | 180 |
| tacgggattg cctcatttcc tgctctgaat tttaaaatta gatattaaag ctgtcatatg | 240 |
| gtttcctcac aaaagtcaac aaagtccaaa caaaaatagt ttgccgtttt actttcatcc | 300 |
| attgaaaaag gaaattgtgc ctcttgcagc ctaggcaaag gacatttagt actatcgatt | 360 |
| ctttccaccc tcacgatgac ttgcggttct ctctgtagaa aagggatggc ctaagaaata | 420 |
| caactaaaaa aaaaaaaaa a | 441 |

<210> SEQ ID NO 195
<211> LENGTH: 707
<212> TYPE: DNA
<213> ORGANISM: Homo sapiens

<400> SEQUENCE: 195

| | |
|---|---|
| cagaaaaata tttggaaaaa atataccact tcatagctaa gtcttacaga gaagaggatt | 60 |
| tgctaataaa acttaagttt tgaaaattaa gatgcaggta gagcttctga actaatgccc | 120 |
| acagctccaa ggaagacatg tcctatttag ttattcaaat acaagttgag ggcattgtga | 180 |
| ttaagcaaac aatatatttg ttagaacttt gttttttaaat tactgttcct tgacattact | 240 |
| tataaagagt ctctaacttt cgatttctaa aactatgtaa tacaaaagta tagttttcccc | 300 |
| atttgataaa aggccaatga tactgagtag gatatatgcg tatcatgcta cttcattcag | 360 |
| tgtgtctgtt tttaatacta ataaggcagt ttgacagaaa ttatttctttt gggactaagg | 420 |
| tgattatcat ttttttcccc ttcaaaattg tgctttaagt gctgataacc acaggcagat | 480 |
| tgcaaagaac tgataaggca acaaaagtag agaatttttag gatcaaaggc atgtaactga | 540 |
| aaggtaacaa cagtacataa gcgacaactg gggaaggcag cagtgaaaca tgtttgtggg | 600 |
| gttaagtgag tcattgtaaa taaggaattt gcacatttat tttctgtcga cgcggccgcc | 660 |
| actgtgctgg atatctgcag aattccacca cactggacta gtggatc | 707 |

<210> SEQ ID NO 196
<211> LENGTH: 552
<212> TYPE: DNA
<213> ORGANISM: Homo sapiens

```
<220> FEATURE:
<221> NAME/KEY: misc_feature
<222> LOCATION: (1)...(552)
<223> OTHER INFORMATION: n = A,T,C or G

<400> SEQUENCE: 196
tggccagcca gcctgatgtg gatggcttcc ttggggtggt gcttccctca agcccgaatt      60
ngtggacatc atcaatgcca aacaatgagc cccatccatt ttccctaccc ttcctgccaa     120
gccagggant aagcagccca gaagcccagt aactgccctt tccctgcata tgcttttgat     180
ggtgtcatnt gctccttcct gtggcctcat ccaaactgta tnttccttta ctgtttatat     240
nttcaccctg taatggttgg gaccaggcca atcccttntc cacttactat aatggttgga     300
actaaacgtc accaaggtgg cttntccttg gctgaganat ggaaggcgtg gtgggatttg     360
ctnctgggtt ccctaggccc tagtgagggc agaagagaaa ccatcctntc ccttnttaca     420
ccgtgaggcc aagatcccct cagaaggcag gagtgctgcc ctntcccatg gtgcccgtgc     480
ctntgtgctg tgtatgtgaa ccacccatgt gagggaataa acctggcact aggaaaaaaa     540
aaaaaaaaaa aa                                                         552

<210> SEQ ID NO 197
<211> LENGTH: 449
<212> TYPE: DNA
<213> ORGANISM: Homo sapiens
<220> FEATURE:
<221> NAME/KEY: misc_feature
<222> LOCATION: (1)...(449)
<223> OTHER INFORMATION: n = A,T,C or G

<400> SEQUENCE: 197
ctccagagac aacttcgcgg tgtggtgaac tctctgagga aaaacacgtg cgtggnanca      60
agtgactgag acctanaaat ccaagcgttg gaggtcctga ggccagccta agtcgcttca     120
aaatggaacg aaggcgtttg cggggttcca ttcagagccg atacatcagc atgagtgtgt     180
ggacaagccc acggagactt gtggagctgg cagggcagag cctgctgaag gatgaggccc     240
tggccattgc ccgccctgga gttgctgccc agggagctct tcccgccact cttcatggca     300
gcctttgacg ggagacacag ccagaccctg aaggcaatgg tgcaggcctg gcccttcacc     360
tgcctccctc tgggagtgct gatgaaggga caacatcttc acctggagac cttcaaagct     420
gtgcttgatg gacttgatgt gctccttgc                                       449

<210> SEQ ID NO 198
<211> LENGTH: 606
<212> TYPE: DNA
<213> ORGANISM: Homo sapiens

<400> SEQUENCE: 198
tgagtttgcc cccttacccc catcccagtg aatatttgca attcctaaag acgtgttttg      60
attgtcacac ctgggtgggg aacatgctac tggcatctaa tgcatagagg gcagtaatgc     120
tgctaaacat ctttcaacgc acaggacaga gccccacaaa agagaattat ctagccccaa     180
atgtccataa cactgctgtt gagaaaacct accgcaggat cttactgggc ttcataggta     240
agcttgcctt tgttctggct tctgtagata tataaaataa agacactgcc cagtccctcc     300
ctcaacgtcc cgagccaggg ctcaaggcaa ttccaataac agtagaatga acactaaata     360
ttgatttcaa aatctcagca actagaagaa tgaccaacca tcctggttgg cctgggactg     420
tcctagtttt agcattgaaa gtttcaggtt ccaggaaagc cctcaggcct gggctgctgg     480
```

-continued

```
tcaccctagc agctgaggga ctcttcaata cagaattagt ctttgtgcac tggagatgaa    540
tatactttaa tttgtaacat gtgaaaacat ctataaacat ctactgaagc ctgttcttgt    600
ctgcac                                                                606
```

<210> SEQ ID NO 199
<211> LENGTH: 369
<212> TYPE: DNA
<213> ORGANISM: Homo sapiens
<220> FEATURE:
<221> NAME/KEY: misc_feature
<222> LOCATION: (1)...(369)
<223> OTHER INFORMATION: n = A,T,C or G

<400> SEQUENCE: 199

```
ggcaactttt tgcggattgt tcttgcttnc aggctttgcg ctgcaaatcc agtgctacca     60
gtgtgaagaa ttccagctga caacgactg ctcctccccc gagttcattg tgaattgcac    120
ggtgaacgtt caagacatgt gtcagaaaga agtgatgag caaagtgccg ggatcatgta    180
ccgcaagtcc tgtgcatcat cagcggcctg tctcatcgcc tctgccgggt accagtcctt    240
ctgctcccca gggaaactga actcagtttg catcagctgc tgcaacaccc ctctttgtaa    300
cgggccaagg cccaagaaaa ggggaagttc tgcctcggcc ctcangccat ggctccgcac    360
caccatcct                                                             369
```

<210> SEQ ID NO 200
<211> LENGTH: 55
<212> TYPE: PRT
<213> ORGANISM: Homo sapiens

<400> SEQUENCE: 200

```
Met Tyr Arg Asn Trp Ser Gly Cys Phe Gly Leu Gln Val Thr Leu Cys
                 5                  10                  15

His Thr Phe Glu Thr Arg Asp Leu Ser Arg Leu Ser Ser Asp Ser Gln
             20                  25                  30

Pro Thr Ser Asn Val Ser Gln Ser Ile Ser His Lys Val Leu Ser Phe
         35                  40                  45

Ser Gly Val Ile Val Thr Pro
     50                  55
```

<210> SEQ ID NO 201
<211> LENGTH: 67
<212> TYPE: PRT
<213> ORGANISM: Homo sapiens

<400> SEQUENCE: 201

```
Met Gln Leu Leu Ser Pro Asn Thr Lys Phe Thr Ser Cys Leu Ser Arg
                 5                  10                  15

Gln Arg Gly Asn Leu Val Phe Leu Gly Asp Leu Lys Gly Cys Ser Glu
             20                  25                  30

Leu Lys Asn Phe Gln Glu Leu Ile Asn Gln Ser Ala Leu Val His Pro
         35                  40                  45

Arg Val Asp Val Trp Trp Tyr Cys Gly Gly Pro Leu Leu Gly Thr Leu
     50                  55                  60

Pro Asn Asn
 65
```

<210> SEQ ID NO 202
<211> LENGTH: 73
<212> TYPE: PRT

<213> ORGANISM: Homo sapiens

<400> SEQUENCE: 202

| Met | Thr | Pro | Glu | Lys | Leu | Arg | Thr | Leu | Cys | Glu | Ile | Asp | Trp | Leu | Thr |
|---|---|---|---|---|---|---|---|---|---|---|---|---|---|---|---|
| | | | | 5 | | | | | 10 | | | | | 15 | |

| Leu | Glu | Val | Gly | Trp | Leu | Ser | Glu | Ser | Leu | Glu | Arg | Ser | Leu | Val |
|---|---|---|---|---|---|---|---|---|---|---|---|---|---|---|
| | | | | 20 | | | | | 25 | | | | | 30 |

| Ser | Lys | Val | Trp | His | Lys | Val | Thr | Cys | Lys | Pro | Lys | His | Pro | Asp | Gln |
|---|---|---|---|---|---|---|---|---|---|---|---|---|---|---|---|
| | | | | 35 | | | | | 40 | | | | | 45 | |

| Phe | Leu | Tyr | Ile | Asp | Ser | Tyr | Ser | Trp | Phe | Arg | Pro | Leu | Pro | Pro | Leu |
|---|---|---|---|---|---|---|---|---|---|---|---|---|---|---|---|
| | | 50 | | | | | 55 | | | | | 60 | | | |

| Pro | Thr | Val | Val | Lys | Arg | Thr | Ala | Ala |
|---|---|---|---|---|---|---|---|---|
| 65 | | | | | 70 | | | |

<210> SEQ ID NO 203
<211> LENGTH: 2008
<212> TYPE: DNA
<213> ORGANISM: Homo sapiens

<400> SEQUENCE: 203

```
ctccagagac aacttcgcgg tgtggtgaac tctctgagga aaaacacgtg cgtggtaaca      60
agtgactgag acctagaaat ccaagcgttg gaggtcctga ggccagccta agtcgcttca     120
aaatggaacg aaggcgtttg cggggttcca ttcagagccg atacatcagc atgagtgtgt     180
ggacaagccc acggagactt gtggagctgg cagggcagag cctgctgaag gatgaggccc     240
tggccattgc ccgccctgga gttgctgccc agggagctct tcccgccact cttcatggca     300
gcctttgacg ggagacacag ccagaccctg aaggcaatgg tgcaggcctg gcccttcacc     360
tgcctcccte tgggagtgct gatgaaggga caacatcttc acctggagac cttcaaagct     420
gtgcttgatg gacttgatgt gctccttgcc caggaggttc gccccaggag gtggaaactt     480
caagtgctgg atttacggaa gaactctcat caggacttct ggactgtatg gtctggaaac     540
agggccagtc tgtactcatt tccagagcca gaagcagctc agcccatgac aaagaagcga     600
aaagtagatg gtttgagcac agaggcagag cagcccttca ttccagtaga ggtgctcgta     660
gacctgttcc tcaaggaagg tgcctgtgat gaattgttct cctacctcat tgagaaagtg     720
aagcgaaaga aaaatgtact acgcctgtgc tgtaagaagc tgaagatttt tgcaatgccc     780
atgcaggata tcaagatgat cctgaaaatg gtgcagctgg actctattga agatttggaa     840
gtgacttgta cctggaagct acccaccttg gcgaaatttt ctccttacct gggccagatg     900
attaatctgc gtagactcct cctctcccac atccatgcat cttcctacat ttccccggag     960
aaggaagagc agtatatcgc ccagttcacc tctcagttcc tcagtctgca gtgcctgcag    1020
gctctctatg tggactcttt attttttcctt agaggccgcc tggatcagtt gctcaggcac    1080
gtgatgaacc ccttggaaac cctctcaata actaactgcc ggctttcgga aggggatgtg    1140
atgcatctgt cccagagtcc cagcgtcagt cagctaagtg tcctgagtct aagtggggtc    1200
atgctgaccg atgtaagtcc cgagcccctc caagctctgc tggagagagc ctctgccacc    1260
ctccaggacc tggtctttga tgagtgtggg atcacggatg atcagctcct gccctcctg    1320
ccttccctga gccactgctc ccagcttaca accttaagct tctacgggaa ttccatctcc    1380
atatctgcct tgcagagtct cctgcagcac ctcatcgggc tgagcaatct gacccacgtg    1440
ctgtatcctg tcccctgga gagttatgag acatccatg gtaccctcca cctgagagg    1500
cttgcctatc tgcatgccag gctcagggag ttgctgtgtg agttggggcg gcccagcatg    1560
```

| | | | | |
|---|---|---|---|---|
| gtctggctta | gtgccaaccc | ctgtcctcac | tgtggggaca | gaaccttcta | tgacccggag | 1620 |
| cccatcctgt | gcccctgttt | catgcctaac | tagctgggtg | cacatatcaa | atgcttcatt | 1680 |
| ctgcatactt | ggacactaaa | gccaggatgt | gcatgcatct | tgaagcaaca | aagcagccac | 1740 |
| agtttcagac | aaatgttcag | tgtgagtgag | gaaaacatgt | tcagtgagga | aaaaacattc | 1800 |
| agacaaatgt | tcagtgagga | aaaaagggg | aagttgggga | taggcagatg | ttgacttgag | 1860 |
| gagttaatgt | gatctttggg | gagatacatc | ttatagagtt | agaaatagaa | tctgaatttc | 1920 |
| taaagggaga | ttctggcttg | ggaagtacat | gtaggagtta | atccctgtgt | agactgttgt | 1980 |
| aaagaaactg | ttgaaaaaaa | aaaaaaaa | | | | 2008 |

<210> SEQ ID NO 204
<211> LENGTH: 923
<212> TYPE: DNA
<213> ORGANISM: Homo sapiens

<400> SEQUENCE: 204

| | | | | | | |
|---|---|---|---|---|---|---|
| tgagtttgcc | cccttacccc | catcccagtg | aatatttgca | attcctaaag | acgtgttttg | 60 |
| attgtcacac | ctgggtgggg | aacatgctac | tggcatctaa | tgcatagagg | gcagtaatgc | 120 |
| tgctaaacat | ctttcaacgc | acaggacaga | gccccacaaa | agagaattat | ctagccccaa | 180 |
| atgtccataa | cactgctgtt | gagaaaacct | accgcaggat | cttactgggc | ttcataggta | 240 |
| agcttgcctt | tgttctggct | tctgtagata | tataaaataa | agacactgcc | cagtccctcc | 300 |
| ctcaacgtcc | cgagccaggg | ctcaaggcaa | ttccaataac | agtagaatga | acactaaata | 360 |
| ttgatttcaa | aatctcagca | actagaagaa | tgaccaacca | tcctggttgg | cctgggactg | 420 |
| tcctagtttt | agcattgaaa | gtttcaggtt | ccaggaaagc | cctcaggcct | gggctgctgg | 480 |
| tcaccctagc | agctgaggga | ctcttcaata | cagaattagt | ctttgtgcac | tggagatgaa | 540 |
| tatactttaa | tttgtaacat | gtgaaaacat | ctataaacat | ctactgaagc | ctgttctgtc | 600 |
| tgcaccgaca | ttttcattga | gtacggattc | ttcctaccag | atacagctgc | tctacaactt | 660 |
| tcgagggctg | gtataaaact | agcttttacc | tattttttaaa | aattacatga | atagtaaaaa | 720 |
| cttggattaa | cccagtattc | gggtattttc | aatttccttg | ggagcttaga | ggacggacaa | 780 |
| ataaaaagat | tatttcaaca | tcaaatatat | gctattgttt | acatatgaag | ataaccacat | 840 |
| atatgtataa | attcaccgtt | acttttttagc | aatactataa | aatccaacag | aaaaaaatag | 900 |
| catttactaa | aaaaaaaaaa | aaa | | | | 923 |

<210> SEQ ID NO 205
<211> LENGTH: 1619
<212> TYPE: DNA
<213> ORGANISM: Homo sapiens

<400> SEQUENCE: 205

| | | | | | | |
|---|---|---|---|---|---|---|
| ggcaactttt | tgcggattgt | tcttgcttcc | aggctttgcg | ctgcaaatcc | agtgctacca | 60 |
| gtgtgaagaa | ttccagctga | caacgactgc | ctcctccccc | gagttcattg | tgaattgcac | 120 |
| ggtgaacgtt | caagacatgt | gtcagaaaga | agtgatggag | caaagtgccg | ggatcatgta | 180 |
| ccgcaagtcc | tgtgcatcat | cagcggcctg | tctcatcgcc | tctgccgggt | accagtcctt | 240 |
| ctgctcccca | gggaaactga | actcagtttg | catcagctgc | tgcaacaccc | ctctttgtaa | 300 |
| cgggccaagg | cccaagaaaa | ggggaagttc | tgcctcggcc | tcaggccag | gctccgcac | 360 |
| caccatcctg | ttcctcaaat | tagccctctt | ctcggcacac | tgctgaagct | gaaggagatg | 420 |
| ccaccccctc | ctgcattgtt | cttccagccc | tcgcccccaa | ccccccacct | ccctgagtga | 480 |

```
gtttcttctg ggtgtcctttt tattctgggt agggagcggg agtccgtgtt ctcttttgtt      540
cctgtgcaaa taatgaaaga gctcggtaaa gcattctgaa taaattcagc ctgactgaat      600
tttcagtatg tacttgaagg aaggaggtgg agtgaaagtt caccccatg tctgtgtaac       660 cggagtcaag gccaggctgg cagagtcagt ccttagaagt cactgaggtg ggcatctgcc      720
ttttgtaaag cctccagtgt ccattccatc cctgatgggg gcatagtttg agactgcaga     780
gtgagagtga cgttttctta gggctggagg gccagttccc actcaaggct ccctcgcttg      840
acattcaaac ttcatgctcc tgaaaaccat tctctgcagc agaattggct ggtttcgcgc      900
ctgagttggg ctctagtgac tcgagactca atgactggga cttagactgg ggctcggcct     960
cgctctgaaa agtgcttaag aaaatcttct cagttctcct tgcagaggac tggcgccggg     1020
acgcgaagag caacgggcgc tgcacaaagc gggcgctgtc ggtggtggag tgcgcatgta     1080
cgcgcaggcg cttctcgtgg ttggcgtgct gcagcgacag gcggcagcac agcaccttgc     1140
acgaacaccc gccgaaactg ctgcgaggac accgtgtaca ggagcgggtt gatgaccgag     1200
ctgaggtaga aaacgtctc cgagaagggg aggaggatca tgtacgcccg gaagtaggac      1260
ctcgtccagt cgtgcttggg tttggccgca gccatgatcc tccgaatctg gttgggcatc     1320
cagcatacgg ccaatgtcac aacaatcagc cctgggcaga cacgagcagg agggagagac     1380
agagaaaaga aaaacacagc atgagaacac agtaaatgaa taaaaccata aaatatttag     1440
cccctctgtt ctgtgcttac tggccaggaa atggtaccaa tttttcagtg ttggacttga     1500
cagcttcttt tgccacaagc aagagagaat ttaacactgt ttcaaacccg ggggagttgg     1560
ctgtgttaaa gaaagaccat taaatgcttt agacagtgta aaaaaaaaaa aaaaaaaaa     1619
```

COMPOSITIONS AND METHODS FOR THE THERAPY AND DIAGNOSIS OF OVARIAN CANCER

CROSS REFERENCE TO RELATED APPLICATIONS

This application is a continuation-in-part of U.S. patent application Ser. No. 09/656,668, filed Sep. 7, 2000, which is a CIP of U.S. application Ser. No. 09/640,173, filed Aug. 15, 2000, which is a is a CIP of U.S. application Ser. No. 09/561,778, filed May 1, 2000, now abandoned which is a CIP of U.S. application Ser. No. 09/394,374, filed Sep. 10, 1999, now abandoned all pending and incorporated by reference in their entirety herein.

TECHNICAL FIELD

The present invention relates generally to ovarian cancer therapy. The invention is more specifically related to polypeptides comprising at least a portion of an ovarian carcinoma protein, and to polynucleotides encoding such polypeptides, as well as antibodies and immune system cells that specifically recognize such polypeptides. Such polypeptides, polynucleotides, antibodies and cells may be used in vaccines and pharmaceutical compositions for treatment of ovarian cancer.

BACKGROUND OF THE INVENTION

Ovarian cancer is a significant health problem for women in the United States and throughout the world. Although advances have been made in detection and therapy of this cancer, no vaccine or other universally successful method for prevention or treatment is currently available. Management of the disease currently relies on a combination of early diagnosis and aggressive treatment, which may include one or more of a variety of treatments such as surgery, radiotherapy, chemotherapy and hormone therapy. The course of treatment for a particular cancer is often selected based on a variety of prognostic parameters, including an analysis of specific tumor markers. However, the use of established markers often leads to a result that is difficult to interpret, and high mortality continues to be observed in many cancer patients.

Immunotherapies have the potential to substantially improve cancer treatment and survival. Such therapies may involve the generation or enhancement of an immune response to an ovarian carcinoma antigen. However, to date, relatively few ovarian carcinoma antigens are known and the generation of an immune response against such antigens has not been shown to be therapeutically beneficial.

Accordingly, there is a need in the art for improved methods for identifying ovarian tumor antigens and for using such antigens in the therapy of ovarian cancer. The present invention fulfills these needs and further provides other related advantages.

SUMMARY OF THE INVENTION

Briefly stated, this invention provides compositions and methods for the therapy of cancer, such as ovarian cancer.

In one aspect, the present invention provides polynucleotide compositions comprising a sequence selected from the group consisting of:

(a) sequences provided in SEQ ID NOs: 1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185, 193–199, and 203–205;

(b) complements of the sequences provided in SEQ ID NOs: 1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185, 193–199, and 203–205;

(c) sequences consisting of at least 20 contiguous residues of a sequence provided in SEQ ID NOs: 1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185, 193–199, and 203–205;

(d) sequences that hybridize to a sequence provided in SEQ ID NOs: 1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185, 193–199, and 203–205 under moderately stringent conditions;

(e) sequences having at least 75% identity to a sequence provided in SEQ ID NOs: 1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185, 193–199, and 203–205;

(f) sequences having at least 90% identity to a sequence provided in SEQ ID NOs: 1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185, 193–199, and 203–205; and (g) degenerate variants of a sequence provided in SEQ ID NOs: 1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185, 193–199, and 203–205.

In one preferred embodiment, the polynucleotide compositions of the invention are expressed in at least about 20%, more preferably in at least about 30%, and most preferably in at least about 50% of ovarian tumors samples tested, at a level that is at least about 2-fold, preferably at least about 5-fold, and most preferably at least about 10-fold higher than that for normal tissues.

In one aspect, the present invention provides polypeptides comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished. Within certain embodiments, the ovarian carcinoma protein comprises a sequence that is encoded by a polynucleotide sequence selected from the group consisting of SEQ ID NOs: 1, 2, 5, 9, 10, 13, 16, 19, 23, 27, 28, 32, 33, 35, 38, 4–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185, 193–199, and 203–205, and complements of such polynucleotides.

The present invention further provides polynucleotides that encode a polypeptide as described above or a portion thereof, expression vectors comprising such polynucleotides and host cells transformed or transfected with such expression vectors.

The present invention further provides polypeptide compositions comprising an amino acid sequence selected from the group consisting of sequences recited in SEQ ID NOs: 200–202.

In certain preferred embodiments, the polypeptides of the present invention are immunogenic, i.e., they are capable of eliciting an immune response, particularly a humoral and/or cellular immune response, as further described herein.

The present invention further provides fragments, variants and/or derivatives of the disclosed polypeptide sequences, wherein the fragments, variants and/or derivatives preferably have a level of immunogenic activity of at least about 50%, preferably at least about 70% and more preferably at least about 90% of the level of immunogenic activity of a the ovarian carcinoma protein comprises an amino acid sequence encoded by a polynucleotide that comprises a sequence recited in any one of SEQ ID NOs: 1–185, 187–199, and 203–205.

Within other aspects, the present invention provides pharmaceutical compositions comprising a polypeptide and/or polynucleotide as described above and a physiologically acceptable carrier.

Within a related aspect of the present invention, the pharmaceutical compositions, e.g., vaccine compositions, are provided for prophylactic or therapeutic applications. Such compositions generally comprise an immunogenic polypeptide or polynucleotide of the invention and an immunostimulant, such as an adjuvant.

The present invention further provides pharmaceutical compositions that comprise: (a) an antibody or antigen-binding fragment thereof that specifically binds to a polypeptide of the present invention, or a fragment thereof, and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Illustrative antigen presenting cells include dendritic cells, macrophages, monocytes, fibroblasts and B cells.

Within related aspects, pharmaceutical compositions are provided that comprise: (a) an antigen presenting cell that expresses a polypeptide as described above and (b) an immunostimulant.

The present invention further provides, in other aspects, fusion proteins that comprise at least one polypeptide as described above, as well as polynucleotides encoding such fusion proteins, typically in the form of pharmaceutical compositions, e.g., vaccine compositions, comprising a physiologically acceptable carrier and/or an immunostimulant. The fusions proteins may comprise multiple immunogenic polypeptides or portions/variants thereof, as described herein, and may further comprise one or more polypeptide segments for facilitating the expression, purification and/or immunogenicity of the polypeptide(s).

Within further aspects, the present invention provides methods for stimulating an immune response in a patient, preferably a T cell response in a human patient, comprising administering a pharmaceutical composition described herein. The patient may be afflicted with ovarian cancer, in which case the methods provide treatment for the disease, or patient considered at risk for such a disease may be treated prophylactically.

Within further aspects, the present invention provides methods for inhibiting the development of a cancer in a patient, comprising administering to a patient a pharmaceutical composition as recited above. The patient may be afflicted with ovarian cancer, in which case the methods provide treatment for the disease, or patient considered at risk for such a disease may be treated prophylactically.

The present invention further provides, within other aspects, methods for removing tumor cells from a biological sample, comprising contacting a biological sample with T cells that specifically react with a polypeptide of the present invention, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a polypeptide of the present invention, comprising contacting T cells with one or more of: (i) an ovarian carcinoma polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating $CD4^+$ and/or $CD8^+$ T cells isolated from a patient with one or more of: (i) a polypeptide comprising at least an immunogenic portion of polypeptide disclosed herein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer, preferably an ovarian cancer, in a patient comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a polypeptide of the present invention; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a polypeptide of the present invention; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description. All references disclosed herein are hereby incorporated by reference in their entirety as if each was incorporated individually.

BRIEF DESCRIPTION OF THE SEQUENCE IDENTIFIERS

SEQ ID NOs: 1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185, and 193–199 are described in Tables III–VII below.

SEQ ID NO: 200 is the amino acid sequence of a polypeptide encoded by the polynucleotide recited in SEQ ID NO: 182;

SEQ ID NO: 201 is the amino acid sequence of a polypeptide encoded by the polynucleotide recited in SEQ ID NO: 182;

SEQ ID NO: 202 is the amino acid sequence of a polypeptide encoded by the polynucleotide recited in SEQ ID NO: 182.

SEQ ID NO: 203 is the determined extended cDNA sequence for SEQ ID NO: 197.

SEQ ID NO: 204 is the determined extended cDNA sequence for SEQ ID NO: 198.

SEQ ID NO: 205 is the determined extended cDNA sequence for SEQ ID NO: 199.

DETAILED DESCRIPTION OF THE INVENTION

The present invention is directed generally to compositions and their use in the therapy and diagnosis of cancer, particularly ovarian cancer. As described further below, illustrative compositions of the present invention include, but are not restricted to, polypeptides, particularly immunogenic polypeptides, polynucleotides encoding such polypeptides, antibodies and other binding agents, antigen presenting cells (APCs) and immune system cells (e.g., T cells).

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

Polypeptide Compositions

As used herein, the term "polypeptide" is used in its conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof Particular polypeptides of interest in the context of this invention are amino acid subsequences comprising epitopes, i.e., antigenic determinants substantially responsible for the immunogenic properties of a polypeptide and being capable of evoking an immune response.

Particularly illustrative polypeptides of the present invention comprise those encoded by a polynucleotide sequence set forth in any one of SEQ ID NOs: 1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185 and 193–199 or a sequence that hybridizes under moderately stringent conditions, or, alternatively, under highly stringent conditions, to a polynucleotide sequence identified above. Certain other illustrative polypeptides of the invention comprise amino acid sequences as set forth in any one of SEQ ID NOs: 200–202.

The polypeptides of the present invention are sometimes herein referred to as ovarian tumor proteins or ovarian tumor polypeptides, as an indication that their identification has been based at least in part upon their increased levels of expression in ovarian tumor samples. Thus, a "ovarian tumor polypeptide" or "ovarian tumor protein," refers generally to a polypeptide sequence of the present invention, or a polynucleotide sequence encoding such a polypeptide, that is expressed in a substantial proportion of ovarian tumor samples, for example preferably greater than about 20%, more preferably greater than about 30%, and most preferably greater than about 50% or more of ovarian tumor samples tested, at a level that is at least two fold, and preferably at least five fold, greater than the level of expression in normal tissues, as determined using a representative assay provided herein. An ovarian tumor polypeptide sequence of the invention, based upon its increased level of expression in tumor cells, has particular utility both as a diagnostic marker as well as a therapeutic target, as further described below.

In certain preferred embodiments, the polypeptides of the invention are immunogenic, i.e., they react detectably within an immunoassay (such as an ELISA or T-cell stimulation assay) with antisera and/or T-cells from a patient with ovarian cancer. Screening for immunogenic activity can be performed using techniques well known to the skilled artisan. For example, such screens can be performed using methods such as those described in Harlow and Lane, *Antibodies: A Laboratory Manual*, Cold Spring Harbor Laboratory, 1988. In one illustrative example, a polypeptide may be immobilized on a solid support and contacted with patient sera to allow binding of antibodies within the sera to the immobilized polypeptide. Unbound sera may then be removed and bound antibodies detected using, for example, $^{125}$I–labeled Protein A.

As would be recognized by the skilled artisan, immunogenic portions of the polypeptides disclosed herein are also encompassed by the present invention. An "immunogenic portion," as used herein, is a fragment of an immunogenic polypeptide of the invention that itself is immunologically reactive (i.e., specifically binds) with the B-cells and/or T-cell surface antigen receptors that recognize the polypeptide. Immunogenic portions may generally be identified using well known techniques, such as those summarized in Paul, *Fundamental Immunology*, 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well-known techniques.

In one preferred embodiment, an immunogenic portion of a polypeptide of the present invention is a portion that reacts with antisera and/or T-cells at a level that is not substantially less than the reactivity of the full-length polypeptide (e.g., in an ELISA and/or T-cell reactivity assay). Preferably, the level of immunogenic activity of the immunogenic portion is at least about 50%, preferably at least about 70% and most preferably greater than about 90% of the immunogenicity for the full-length polypeptide. In some instances, preferred immunogenic portions will be identified that have a level of immunogenic activity greater than that of the corresponding full-length polypeptide, e.g., having greater than about 100% or 150% or more immunogenic activity.

In certain other embodiments, illustrative immunogenic portions may include peptides in which an N-terminal leader sequence and/or transmembrane domain have been deleted. Other illustrative immunogenic portions will contain a small N- and/or C-terminal deletion (e.g., 1–30 amino acids, preferably 5–15 amino acids), relative to the mature protein.

In another embodiment, a polypeptide composition of the invention may also comprise one or more polypeptides that are immunologically reactive with T cells and/or antibodies generated against a polypeptide of the invention, particularly a polypeptide having an amino acid sequence disclosed herein, or to an immunogenic fragment or variant thereof.

In another embodiment of the invention, polypeptides are provided that comprise one or more polypeptides that are capable of eliciting T cells and/or antibodies that are immunologically reactive with one or more polypeptides described herein, or one or more polypeptides encoded by contiguous nucleic acid sequences contained in the polynucleotide sequences disclosed herein, or immunogenic fragments or variants thereof, or to one or more nucleic acid sequences which hybridize to one or more of these sequences under conditions of moderate to high stringency.

The present invention, in another aspect, provides polypeptide fragments comprising at least about 5, 10, 15, 20, 25, 50, or 100 contiguous amino acids, or more, including all intermediate lengths, of a polypeptide compositions set forth herein, such as those set forth in SEQ ID NOs: 200–202, or those encoded by a polynucleotide sequence set forth in any one of SEQ ID NOs: 1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185 and 193–199.

In another aspect, the present invention provides variants of the polypeptide compositions described herein. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequences set forth herein.

In one preferred embodiment, the polypeptide fragments and variants provide by the present invention are immunologically reactive with an antibody and/or T-cell that reacts with a full-length polypeptide specifically set for the herein.

In another preferred embodiment, the polypeptide fragments and variants provided by the present invention exhibit a level of immunogenic activity of at least about 50%, preferably at least about 70%, and most preferably at least about 90% or more of that exhibited by a full-length polypeptide sequence specifically set forth herein.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating their immunogenic activity as described herein and/or using any of a number of techniques well known in the art.

For example, certain illustrative variants of the polypeptides of the invention include those in which one or more portions, such as an N-terminal leader sequence or transmembrane domain, have been removed. Other illustrative variants include variants in which a small portion (e.g., 1–30 amino acids, preferably 5–15 amino acids) has been removed from the N- and/or C-terminal of the mature protein.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics, e.g., with immunogenic characteristics. When it is desired to alter the amino acid sequence of a polypeptide to create an equivalent, or even an improved, immunogenic variant or portion of a polypeptide of the invention, one skilled in the art will typically change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

TABLE 1

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726–730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389–3402 and Altschul et al. (1990) *J. Mol. Biol.* 215:403–410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

Within other illustrative embodiments, a polypeptide may be a fusion polypeptide that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39–46, 1985; Murphy et al., Proc. Natl. Acad. Sci. USA 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The fusion polypeptide can comprise a polypeptide as described herein together with an unrelated immunogenic protein, such as an immunogenic protein capable of eliciting a recall response. Examples of such proteins include tetanus, tuberculosis and hepatitis proteins (see, for example, Stoute et al. New Engl. J. Med., 336:86–91, 1997).

In one preferred embodiment, the immunological fusion partner is derived from a Mycobacterium sp., such as a Mycobacterium tuberculosis-derived Ra12 fragment. Ra12 compositions and methods for their use in enhancing the expression and/or immunogenicity of heterologous polynucleotide/polypeptide sequences is described in U.S. patent application Ser. No. 60/158,585, the disclosure of which is incorporated herein by reference in its entirety. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis*. The nucleotide sequence and amino acid sequence of MTB32A have been described (for example, U.S. patent application Ser. No. 60/158,585; see also, Skeiky et al., *Infection and Immun.* (1999) 67:3998–4007, incorporated herein by reference). C-terminal fragments of the MTB32A coding sequence express at high levels and remain as a soluble polypeptides throughout the purification process. Moreover, Ra12 may enhance the immunogenicity of heterologous immunogenic polypeptides with which it is fused. One preferred Ra12 fusion polypeptide comprises a 14 KD C-terminal fragment corresponding to amino acid residues 192 to 323 of MTB32A. Other preferred Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/ or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Within other preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from Streptococcus pneumoniae, which synthesizes an N-acetyl-L-alanine amidase known as amidase LYTA (encoded by the LytA gene; Gene 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion polypeptide. A repeat portion is found in the C-terminal region starting at residue 178. A particularly preferred repeat portion incorporates residues 188–305.

Yet another illustrative embodiment involves fusion polypeptides, and the polynucleotides encoding them, wherein the fusion partner comprises a targeting signal capable of directing a polypeptide to the endosomal/ lysosomal compartment, as described in U.S. Pat. No. 5,633, 234. An immunogenic polypeptide of the invention, when fused with this targeting signal, will associate more efficiently with MHC class II molecules and thereby provide enhanced in vivo stimulation of $CD4^+$ T-cells specific for the polypeptide.

Polypeptides of the invention are prepared using any of a variety of well known synthetic and/or recombinant techniques, the latter of which are further described below. Polypeptides, portions and other variants generally less than about 150 amino acids can be generated by synthetic means, using techniques well known to those of ordinary skill in the art. In one illustrative example, such polypeptides are synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division (Foster City, Calif.), and may be operated according to the manufacturer's instructions.

In general, polypeptide compositions (including fusion polypeptides) of the invention are isolated. An "isolated" polypeptide is one that is removed from its original environment. For example, a naturally-occurring protein or polypeptide is isolated if it is separated from some or all of the coexisting materials in the natural system. Preferably, such polypeptides are also purified, e.g., are at least about 90% pure, more preferably at least about 95% pure and most preferably at least about 99% pure.

Polynucleotide Compositions

The present invention, in other aspects, provides polynucleotide compositions. The terms "DNA" and "polynucleotide" are used essentially interchangeably herein to refer to a DNA molecule that has been isolated free of total genomic DNA of a particular species. "Isolated," as used herein, means that a polynucleotide is substantially away from other coding sequences, and that the DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man.

As will be understood by those skilled in the art, the polynucleotide compositions of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be also recognized by the skilled artisan, polynucleotides of the invention may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a polypeptide/protein of the invention or a portion thereof) or may comprise a sequence that encodes a variant or derivative, preferably and immunogenic variant or derivative, of such a sequence.

Therefore, according to another aspect of the present invention, polynucleotide compositions are provided that comprise some or all of a polynucleotide sequence set forth in any one of SEQ ID NOs: 1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185 and 193–199, complements of a polynucleotide sequence set forth as described above, and degenerate variants of a polynucleotide sequence set forth as described above. In certain preferred embodiments, the polynucleotide sequences set forth herein encode immunogenic polypeptides, as described above.

In other related embodiments, the present invention provides polynucleotide variants having substantial identity to the sequences disclosed herein in SEQ ID NOs: 1, 2, 5, 9, 10, 13, 16, 19, 23, 27, 28, 32, 33, 35, 38, 41–50, 52, 53, 56, 57, 63, 65, 69–72, 75, 78, 80–82, 84, 86, 89–93, 95, 97–100, 103, 107, 111, 114, 117, 120, 121, 125, 128, 132–134, 136, 137, 140, 143–146, 148–151, 156, 158, 160–162, 166–168, 171, 174–183, 185 and 193–199, for example those comprising at least 70% sequence identity, preferably at least 75%, 80%, 85%, 90%, 95%, 96%, 97%, 98%, or 99% or higher, sequence identity compared to a polynucleotide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the immunogenicity of the polypeptide encoded by the variant polynucleotide is not substantially diminished relative to a polypeptide encoded by a polynucleotide sequence specifically set forth herein). The term "variants" should also be understood to encompasses homologous genes of xenogenic origin.

In additional embodiments, the present invention provides polynucleotide fragments comprising various lengths of contiguous stretches of sequence identical to or complementary to one or more of the sequences disclosed herein. For example, polynucleotides are provided by this invention that comprise at least about 10, 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200–500; 500–1,000, and the like.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.–60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60–65° C. or 65–70° C.

In certain preferred embodiments, the polynucleotides described above, e.g., polynucleotide variants, fragments and hybridizing sequences, encode polypeptides that are immunologically cross-reactive with a polypeptide sequence specifically set forth herein. In other preferred embodiments, such polynucleotides encode polypeptides that have a level of immunogenic activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor.* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726–730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389–3402 and Altschul et al. (1990) *J. Mol. Biol.* 215:403–410, respectively. BLAST and BLAST 2.0 can be used, for example with the parameters described herein, to determine percent sequence identity for the polynucleotides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Therefore, in another embodiment of the invention, a mutagenesis approach, such as site-specific mutagenesis, is employed for the preparation of immunogenic variants and/ or derivatives of the polypeptides described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nuclcotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the immunogenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants of the present invention, recursive sequence recombination, as described in U.S. Pat. No. 5,837,458, may be employed. In this approach, iterative cycles of recombination and screening or selection are performed to "evolve" individual polynucleotide variants of the invention having, for example, enhanced immunogenic activity.

In other embodiments of the present invention, the polynucleotide sequences provided herein can be advantageously used as probes or primers for nucleic acid hybridization. As such, it is contemplated that nucleic acid segments that comprise a sequence region of at least about 15 nucleotide long contiguous sequence that has the same sequence as, or is complementary to, a 15 nucleotide long contiguous sequence disclosed herein will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions.

Polynucleotide molecules having sequence regions consisting of contiguous nucleotide stretches of 10–14, 15–20, 30, 50, or even of 100–200 nucleotides or so (including intermediate lengths as well), identical or complementary to a polynucleotide sequence disclosed herein, are particularly contemplated as hybridization probes for use in, e.g., Southern and Northern blotting. This would allow a gene product, or fragment thereof, to be analyzed, both in diverse cell types and also in various bacterial cells. The total size of fragment, as well as the size of the complementary stretch (es), will ultimately depend on the intended use or application of the particular nucleic acid segment. Smaller fragments will generally find use in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15–25 nucleotides in length allows the formation of a duplex molecule that is both stable and selective. Molecules having contiguous complementary sequences over stretches greater than 15 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequences set forth herein, or to any continuous portion of the sequences, from about 15–25 nucleotides in length up to and including the full length sequence, that one wishes to utilize as a probe or primer. The choice of probe and primer sequences may be governed by various factors. For example, one may wish to employ primers from towards the termini of the total sequence.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

The nucleotide sequences of the invention may be used for their ability to selectively form duplex molecules with complementary stretches of the entire gene or gene fragments of interest. Depending on the application envisioned, one will typically desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related sequences.

Of course, for some applications, for example, where one desires to prepare mutants employing a mutant primer strand hybridized to an underlying template, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

According to another embodiment of the present invention, polynucleotide compositions comprising antisense oligonucleotides are provided. Antisense oligonucleotides have been demonstrated to be effective and targeted inhibitors of protein synthesis, and, consequently, provide a therapeutic approach by which a disease can be treated by inhibiting the synthesis of proteins that contribute to the disease. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (U.S. Pat. No. 5,739,119 and U.S. Pat. No. 5,759,829). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., Science. Jun. 10, 1988;240(4858):1544–6; Vasanthakumar and Ahmed, Cancer Commun. 1989;1(4):225–32; Peris et al., Brain Res Mol Brain Res. Jun. 15, 1998;57(2):310–20; U.S. Pat. No. 5,801,154; U.S. Pat. No. 5,789,573; U.S. Pat. No. 5,718,709 and U.S. Pat. No. 5,610,288). Antisense constructs have also been described that inhibit and can be used to treat a variety of abnormal cellular proliferations, e.g. cancer (U.S. Pat. No. 5,747,470; U.S. Pat. No. 5,591,317 and U.S. Pat. No. 5,783,683).

Therefore, in certain embodiments, the present invention provides oligonucleotide sequences that comprise all, or a portion of, any sequence that is capable of specifically binding to polynucleotide sequence described herein, or a complement thereof. In one embodiment, the antisense oligonucleotides comprise DNA or derivatives thereof In another embodiment, the oligonucleotides comprise RNA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof. In each case, preferred compositions comprise a sequence region that is complementary, and more preferably substantially-complementary, and even more preferably, completely complementary to one or more portions of polynucleotides disclosed herein. Selection of antisense compositions specific for a given gene sequence is based upon analysis of the chosen target sequence and determination of secondary structure, $T_m$, binding energy, and relative stability. Antisense compositions may be selected based upon their relative inability to form dimers, hairpins, or other secondary structures that would reduce or prohibit specific binding to the target mRNA in a host cell. Highly preferred target regions of the mRNA, are those which are at or near the AUG translation initiation codon, and those sequences which are substantially complementary to 5' regions of the mRNA. These secondary structure analyses and target site selection considerations can be performed, for example, using v.4 of the OLIGO primer analysis software and/or the BLASTN 2.0.5 algorithm software (Altschul et al., Nucleic Acids Res. 1997, 25(17):3389–402).

The use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., Nucleic Acids Res. Jul. 15, 1997;25(14):2730–6). It has been demonstrated that several molecules of the MPG peptide coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane.

According to another embodiment of the invention, the polynucleotide compositions described herein are used in the design and preparation of ribozyme molecules for inhibiting expression of the tumor polypeptides and proteins of the present invention in tumor cells. Ribozymes are RNA-protein complexes that cleave nucleic acids in a site-specific fashion. Ribozymes have specific catalytic domains that possess endonuclease activity (Kim and Cech, Proc Natl Acad Sci USA. December 1987;84(24):8788–92; Forster and Symons, Cell. Apr. 24, 1987;49(2):211–20). For example, a large number of ribozymes accelerate phosphoester transfer reactions with a high degree of specificity, often cleaving only one of several phosphoesters in an oligonucleotide substrate (Cech et al., Cell. December 1981;27(3 Pt 2):487–96; Michel and Westhof, J. Mol Biol. Dec. 5, 1990;216(3):585–610; Reinhold-Hurek and Shub, Nature. May 14, 1992;357(6374):173–6). This specificity has been attributed to the requirement that the substrate bind via specific base-pairing interactions to the internal guide sequence ("IGS") of the ribozyme prior to chemical reaction.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., Proc Natl Acad Sci USA. Aug. 15, 1992;89(16):7305–9). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif Examples of hammerhead motifs are described by Rossi et al. Nucleic Acids Res. Sep. 11, 1992;20(17):4559–65. Examples of hairpin motifs are described by Hampel et al. (Eur. Pat. Appl. Publ. No. EP 0360257), Hampel and Tritz, Biochemistry Jun. 13, 1989;28 (12):4929–33; Hampel et al., Nucleic Acids Res. Jan. 25, 1990;18(2):299–304 and U.S. Pat. No. 5,631,359. An example of the hepatitis δ virus motif is described by Perrotta and Been, Biochemistry. Dec. 1, 1992;31(47):11843–52; an example of the RNaseP motif is described by Guerrier-Takada et al., Cell. December 1983;35(3 Pt 2):849–57; Neurospora VS RNA ribozyme motif is described by Collins (Saville and Collins, Cell. May 18, 1990;61(4):685–96; Saville and Collins, Proc Natl Acad Sci USA. Oct. 1, 1991;88(19):8826–30; Collins and Olive, Biochemistry. Mar. 23, 1993;32(11):2795–9); and an example of the Group I intron is described in (U.S. Pat. No. 4,987,071). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells Ribozymes expressed from such promoters have been shown to function in mammalian cells. Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

In another embodiment of the invention, peptide nucleic acids (PNAs) compositions are provided. PNA is a DNA mimic in which the nucleobases are attached to a pseudopeptide backbone (Good and Nielsen, Antisense Nucleic Acid Drug Dev. 1997 7(4) 431–37). PNA is able to be utilized in a number methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (*Trends Biotechnol* June 1997;15(6):224–9). As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

PNAs have 2-aminoethyl-glycine linkages replacing the normal phosphodiester backbone of DNA (Nielsen et al., *Science* Dec. 6, 1991;254(5037):1497–500; Hanvey et al., *Science*. Nov. 27, 1992;258(5087):1481–5; Hyrup and Nielsen, Bioorg Med Chem. January 1996;4(1):5–23). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc or Fmoc protocols for solid-phase peptide synthesis, although other methods, including a modified Merrifield method, have been used.

PNA monomers or ready-made oligomers are commercially available from PerSeptive Biosystems (Framingham, Mass.). PNA syntheses by either Boc or Fmoc protocols are straightforward using manual or automated protocols (Norton et al., Bioorg Med Chem. April 1995;3(4):437–45). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography, providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (for example, Norton et al., Bioorg Med Chem. April 1995;3(4):437–45; Petersen et al., J Pept Sci. 1995 May-June;1(3):175–83; Orum et al., Biotechniques. September 1995;19(3):472–80; Footer et al., Biochemistry. Aug. 20, 1996;35(33):10673–9; Griffith et a Nucleic Acids Res. Aug. 11, 1995;23(15):3003–8; Pardridge et al., Proc Natl Acad Sci U.S. A. Jun. 6, 1995;92(12):5592–6; Boffa et al., Proc Natl Acad Sci U.S.A. Mar. 14, 1995;92(6):1901–5; Gambacorti-Passerini et al., Blood. Aug. 15, 1996;88(4):1411–7; Armitage et al., Proc Natl Acad Sci U.S.A. Nov. 11, 1997;94(23):12320–5; Seeger et al, Biotechniques. September 1997;23(3):512–7). U.S. Pat. No. 5,700,922 discusses PNA-DNA-PNA chimeric molecules and their uses in diagnostics, modulating protein in organisms, and treatment of conditions susceptible to therapeutics.

Methods of characterizing the antisense binding properties of PNAs are discussed in Rose (Anal Chem. Dec. 15, 1997;65(24):3545–9) and Jensen et al. (Biochemistry. Apr. 22, 1997;36(16):5072–7). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs that have been described and will be apparent to the skilled artisan include use in DNA strand invasion, antisense inhibition, mutational analysis, enhancers of transcription, nucleic acid purification, isolation of transcriptionally active genes, blocking of transcription factor binding, genome cleavage, biosensors, in situ hybridization, and the like.

Polynucleotide Identification, Characterization and Expression

Polynucleotides compositions of the present invention may be identified, prepared and/or manipulated using any of a variety of well established techniques (see generally, Sambrook et al., *Molecular Cloning. A Laboratory Manual*, Cold Spring Harbor Laboratories, Cold Spring Harbor, N.Y., 1989, and other like references). For example, a polynucleotide may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using the microarray technology of Affymetrix, Inc. (Santa Clara, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). Alternatively, polynucleotides may be amplified from cDNA prepared from cells expressing the proteins described herein, such as tumor cells.

Many template dependent processes are available to amplify a target sequences of interest present in a sample.

One of the best known amplification methods is the polymerase chain reaction (™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Any of a number of other template dependent processes, many of which are variations of the PCR Tm amplification technique, are readily known and available in the art. Illustratively, some such methods include the ligase chain reaction (referred to as LCR), described, for example, in Eur. Pat. Appl. Publ. No. 320,308 and U.S. Pat. No. 4,883,750; Qbeta Replicase, described in PCT Intl. Pat. Appl. Publ. No. PCT/US87/00880; Strand Displacement Amplification (SDA) and Repair Chain Reaction (RCR). Still other amplification methods are described in Great Britain Pat. Appl. No. 2 202 328, and in PCT Intl. Pat. Appl. Publ. No. PCT/US89/01025. Other nucleic acid amplification procedures include transcription-based amplification systems (TAS) (PCT Intl. Pat. Appl. Publ. No. WO 88/10315), including nucleic acid sequence based amplification (NASBA) and 3SR. Eur. Pat. Appl. Publ. No. 329,822 describes a nucleic acid amplification process involving cyclically synthesizing single-stranded RNA ("ssRNA"), ssDNA, and double-stranded DNA (dsDNA). PCT Intl. Pat. Appl. Publ. No. WO 89/06700 describes a nucleic acid sequence amplification scheme based on the hybridization of a promoter/primer sequence to a target single-stranded DNA ("ssDNA") followed by transcription of many RNA copies of the sequence. Other amplification methods such as "RACE" (Frohman, 1990), and "one-sided PCR" (Ohara, 1989) are also well-known to those of skill in the art.

An amplified portion of a polynucleotide of the present invention may be used to isolate a full length gene from a suitable library (e.g., a tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full length cDNA molecule can be generated by ligating suitable fragments, using well known techniques.

Alternatively, amplification techniques, such as those described above, can be useful for obtaining a full length coding sequence from a partial cDNA sequence. One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a poly A region or vector sequence, to identify sequences that are 5' and 3' of a known sequence. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980) *Nucl. Acids Res. Symp. Ser*. 215–223, Horn, T. et al. (1980) *Nucl. Acids Res. Symp. Ser*. 225–232). Alternatively, the protein itself may be produced using chemical methods to synthesize the amino acid sequence of a polypeptide, or a portion thereof. For example, peptide synthesis can be performed using various solid-phase techniques (Roberge, J. Y. et al. (1995) *Science* 269:202–204) and automated synthesis may be achieved, for example, using the ABI 431A Peptide Synthesizer (Perkin Elmer, Palo Alto, Calif.).

A newly synthesized peptide may be substantially purified by preparative high performance liquid chromatography (e.g., Creighton, T. (1983) Proteins, Structures and Molecular Principles, WH Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORTI plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, any of a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) *J. Biol. Chem*. 264:5503–5509); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH may be used. For reviews, see Ausubel et al. (supra) and Grant et al. (1987) *Methods Enzymol*. 153:516–544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) *EMBO J*. 6:307–311. Alternatively, plant promoters such as the small subunit of RUBISCO or heat shock promoters may be used (Coruzzi, G. et al. (1984) *EMBO J*. 3:1671–1680; Broglie, R. et al. (1984) *Science* 224:838–843; and Winter, J. et al. (1991) *Results Probl. Cell Differ*. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196).

An insect system may also be used to express a polypeptide of interest. For example, in one such system, *Autographa californica* nuclear polyhedrosis virus (AcNPV) is used as a vector to express foreign genes in *Spodoptera frugiperda* cells or in Trichoplusia larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or Trichoplusia larvae in which the polypeptide of interest may be expressed (Engelhard, E. K. et al. (1994) *Proc. Natl. Acad. Sci.* 91 :3224–3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, COS, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223–32) and adenine phosphoribosyltransferase (Lowy, I. et al. (1990) *Cell* 22:817–23) genes which can be employed in tk.sup.- or aprt.sup.- cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567–70); npt, which confers resistance to the aminoglycosides, neomycin and G-418 (Colbere-Garapin, F. et al (1981) *J. Mol. Biol.* 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) *Proc. Natl. Acad. Sci.* 85:8047–51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121–131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence may be identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211–1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, *Prot. Exp. Purif.* 3:263–281) while the enterokinase cleavage site provides a means for purifying the desired polypeptide from the fusion protein. A discussion of vectors which contain fusion proteins is provided in Kroll, D. J. et al. (1993; *DNA Cell Biol.* 12:441–453).

In addition to recombinant production methods, polypeptides of the invention, and fragments thereof, may be produced by direct peptide synthesis using solid-phase techniques (Merrifield J. (1963) *J. Am. Chem. Soc.* 85:2149–2154). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

Antibody Compositions, Fragments Thereof and Other Binding Agents

According to another aspect, the present invention further provides binding agents, such as antibodies and antigen-binding fragments thereof, that exhibit immunological binding to a tumor polypeptide disclosed herein, or to a portion, variant or derivative thereof. An antibody, or antigen-binding fragment thereof, is said to "specifically bind," "immunogically bind," and/or is "immunologically reactive" to a polypeptide of the invention if it reacts at a detectable level (within, for example, an ELISA assay) with the polypeptide, and does not react detectably with unrelated polypeptides under similar conditions.

Immunological binding, as used in this context, generally refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) Annual Rev. Biochem. 59:439–473.

An "antigen-binding site," or "binding portion" of an antibody refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

Binding agents may be further capable of differentiating between patients with and without a cancer, such as ovarian cancer, using the representative assays provided herein. For example, antibodies or other binding agents that bind to a tumor protein will preferably generate a signal indicating the presence of a cancer in at least about 20% of patients with the disease, more preferably at least about 30% of patients. Alternatively, or in addition, the antibody will generate a negative signal indicating the absence of the disease in at least about 90% of individuals without the cancer. To determine whether a binding agent satisfies this requirement, biological samples (e.g., blood, sera, sputum, urine and/or tumor biopsies) from patients with and without a cancer (as determined using standard clinical tests) may be assayed as described herein for the presence of polypeptides that bind to the binding agent. Preferably, a statistically significant number of samples with and without the disease will be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "F(ab')$_2$" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H::V_L$ heterodimer including an antigen-binding site which retains much of the antigen recognition and binding capabilities of the native antibody molecule. Inbar et al. (1972) Proc. Nat. Acad. Sci. USA 69:2659–2662; Hochman et al. (1976) Biochem 15:2706–2710; and Ehrlich et al. (1980) Biochem 19:4091–4096.

A single chain Fv ("sFv") polypeptide is a covalently linked $V_H::V_L$ heterodimer which is expressed from a gene fusion including $V_H$- and $V_L$-encoding genes linked by a peptide-encoding linker. Huston et al. (1988) Proc. Nat. Acad. Sci. USA 85(16):5879–5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) Nature 349:293–299; Lobuglio et al. (1989) Proc. Nat. Acad. Sci. USA 86:4220–4224; Shaw et al. (1987) J. Immunol. 138:4534–4538; and Brown et al. (1987) Cancer Res. 47:3577–3583), rodent CDRs grafted into a human supporting FR prior to fusion with an appropriate human antibody constant domain (Riechmann et al. (1988) Nature 332:323–327; Verhoeyen et al. (1988) Science 239:1534–1536; and Jones et al. (1986) Nature 321:522–525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al. (1990) Ann. Rev. Biochem. 59:439–473. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

The process of veneering makes use of the available sequence data for human antibody variable domains compiled by Kabat et al., in Sequences of Proteins of Immunological Interest, 4th ed., (U.S. Dept. of Health and Human Services, U.S. Government Printing Office, 1987), updates to the Kabat database, and other accessible U.S. and foreign databases (both nucleic acid and protein). Solvent accessibilities of V region amino acids can be deduced from the known three-dimensional structure for human and murine antibody fragments. There are two general steps in veneering a murine antigen-binding site. Initially, the FRs of the variable domains of an antibody molecule of interest are compared with corresponding FR sequences of human variable domains obtained from the above-identified sources. The most homologous human V regions are then compared residue by residue to corresponding murine amino acids. The residues in the murine FR which differ from the human counterpart are replaced by the residues present in the human moiety using recombinant techniques well known in the art. Residue switching is only carried out with moieties which are at least partially exposed (solvent accessible), and care is exercised in the replacement of amino acid residues which may have a significant effect on the tertiary structure of V region domains, such as proline, glycine and charged amino acids.

In this manner, the resultant "veneered" murine antigen-binding sites are thus designed to retain the murine CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FRs which are believed to influence the "canonical" tertiary structures of the CDR loops. These design criteria are then used to prepare recombinant nucleotide sequences which combine the CDRs of both the heavy and light chain of a murine antigen-binding site into human-appearing FRs that can be used to transfect mammalian cells for the expression of recombinant human antibodies which exhibit the antigen specificity of the murine antibody molecule.

In another embodiment of the invention, monoclonal antibodies of the present invention may be coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, 188Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

T Cell Compositions

The present invention, in another aspect, provides T cells specific for a tumor polypeptide disclosed herein, or for a variant or derivative thereof. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a polypeptide, polynucleotide encoding a polypeptide and/or an antigen presenting cell (APC) that expresses such a polypeptide. Such stimulation is performed under conditions and for a time sufficient to permit the generation of T cells that are specific for the polypeptide of interest. Preferably, a tumor polypeptide or polynucleotide of the invention is present within a delivery vehicle, such as a microsphere, to facilitate the generation of specific T cells.

T cells are considered to be specific for a polypeptide of the present invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., Cancer Res. 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a tumor polypeptide (100 ng/ml–100 $\mu$g/ml, preferably 200 ng/ml–25 $\mu$g/ml) for 3–7 days will typically result in at least a two fold increase in proliferation of the T cells. Contact as described above for 2–3 hours should result in activation of the T cells, as measured using standard cytokine assays in which a two fold increase in the level of cytokine release (e.g., TNF or IFN-$\gamma$) is indicative of T cell activation (see Coligan et al., Current Protocols in Immunology, vol. 1, Wiley Interscience (Greene 1998)). T cells that have been activated in response to a tumor polypeptide, polynucleotide or polypeptide-expressing APC may be $CD4^+$ and/or $CD8^+$. Tumor polypeptide-specific T cells may be expanded using standard techniques. Within preferred embodiments, the T cells are derived from a patient, a related donor or an unrelated donor, and are administered to the patient following stimulation and expansion.

For therapeutic purposes, $CD4^+$ or $CD8^+$ T cells that proliferate in response to a tumor polypeptide, polynucleotide or APC can be expanded in number either in vitro or in vivo. Proliferation of such T cells in vitro may be accomplished in a variety of ways. For example, the T cells can be re-exposed to a tumor polypeptide, or a short peptide corresponding to an immunogenic portion of such a polypeptide, with or without the addition of T cell growth factors, such as interleukin-2, and/or stimulator cells that synthesize a tumor polypeptide. Alternatively, one or more T cells that proliferate in the presence of the tumor polypeptide can be expanded in number by cloning. Methods for cloning cells are well known in the art, and include limiting dilution.

Pharmaceutical Compositions

In additional embodiments, the present invention concerns formulation of one or more of the polynucleotide, polypeptide, T-cell and/or antibody compositions disclos ed herein in pharmaceutically-acceptable carriers f or admini stration to a cell or an animal, either alone, or in combination with one or more other modalities of therapy.

It will be understood that, if desired, a composition as disclosed herein may be administered in combination with other agents as well, such as, e.g., other proteins or polypeptides or various pharmaceutically-active agents. In fact, there is virtually no limit to other components that may also be included, given that the additional agents do not cause a signficant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Therefore, in another aspect of the present invention, pharmaceutical compositions are provided comprising one or more of the polynucleotide, polypeptide, antibody, and/or T-cell compositions described herein in combination with a physiologically acceptable carrier. In certain preferred embodiments, the pharmaceutical compositions of the invention comprise immunogenic polynucleotide and/or polypeptide compositions of the invention for use in prophylactic and theraputic vaccine applications. Vaccine preparation is generally described in, for example, M. F. Powell and M. J. Newman, eds., "Vaccine Design (the subunit and adjuvant approach)," Plenum Press (N.Y., 1995). Generally, such compositions will comprise one or more polynucleotide and/or polypeptide compositions of the present invention in combination with one or more immunostimulants.

It will be apparent that any of the pharmaceutical compositions described herein can contain pharmaceutically acceptable salts of the polynucleotides and polypeptides of the invention. Such salts can be prepared, for example, from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

In another embodiment, illustrative immunogenic compositions, e.g., vaccine compositions, of the present invention comprise DNA encoding one or more of the polypeptides as described above, such that the polypeptide is generated in situ. As noted above, the polynucleotide may be administered within any of a variety of delivery systems known to those of ordinary skill in the art. Indeed, numerous gene delivery techniques are well known in the art, such as those described by Rolland, *Crit. Rev. Therap. Drug Carrier Systems* 15:143–198, 1998, and references cited therein. Appropriate polynucleotide expression systems will, of course, contain the necessary regulatory DNA regulatory sequences for expression in a patient (such as a suitable promoter and terminating signal). Alternatively, bacterial delivery systems may involve the administration of a bacterium (such as *Bacillus-Calmette-Guerrin*) that expresses an immunogenic portion of the polypeptide on its cell surface or secretes such an epitope.

Therefore, in certain embodiments, polynucleotides encoding immunogenic polypeptides described herein are introduced into suitable mammalian host cells for expression using any of a number of known viral-based systems. In one illustrative embodiment, retroviruses provide a convenient and effective platform for gene delivery systems. A selected nucleotide sequence encoding a polypeptide of the present invention can be inserted into a vector and packaged in retroviral particles using techniques known in the art. The recombinant virus can then be isolated and delivered to a subject. A number of illustrative retroviral systems have been described (e.g., U.S. Pat. No. 5,219,740; Miller and Rosman (1989) BioTechniques 7:980–990; Miller, A. D. (1990) Human Gene Therapy 1:5–14; Scarpa et al. (1991) Virology 180:849–852; Burns et al. (1993) Proc. Natl. Acad. Sci. USA 90:8033–8037; and Boris-Lawrie and Temin (1993) Cur. Opin. Genet. Develop. 3:102–109).

In addition, a number of illustrative adenovirus-based systems have also been described. Unlike retroviruses which integrate into the host genome, adenoviruses persist extrachromosomally thus minimizing the risks associated with insertional mutagenesis (Haj-Ahmad and Graham (1986) J. Virol. 57:267–274; Bett et al. (1993) J. Virol. 67:5911–5921; Mittereder et al. (1994) Human Gene Therapy 5:717–729; Seth et al. (1994) J. Virol. 68:933–940; Barr et al. (1994) Gene Therapy 1:51–58; Berkner, K. L. (1988) BioTechniques 6:616–629; and Rich et al. (1993) Human Gene Therapy 4:461–476).

Various adeno-associated virus (AAV) vector systems have also been developed for polynucleotide delivery. AAV vectors can be readily constructed using techniques well known in the art. See, e.g., U.S. Pat. Nos. 5,173,414 and 5,139,941; International Publication Nos. WO 92/01070 and WO 93/03769; Lebkowski et al. (1988) Molec. Cell. Biol. 8:3988–3996; Vincent et al. (1990) Vaccines 90 (Cold Spring Harbor Laboratory Press); Carter, B. J. (1992) Current Opinion in Biotechnology 3:533–539; Muzyczka, N. (1992) Current Topics in Microbiol. and Immunol. 158:97–129; Kotin, R. M. (1994) Human Gene Therapy 5:793–801; Shelling and Smith (1994) Gene Therapy 1:165–169; and Zhou et al. (1994) J. Exp. Med. 179:1867–1875.

Additional viral vectors useful for delivering the polynucleotides encoding polypeptides of the present invention by gene transfer include those derived from the pox family of viruses, such as vaccinia virus and avian poxvirus. By way of example, vaccinia virus recombinants expressing the novel molecules can be constructed as follows. The DNA encoding a polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the polypeptide of interest into the viral genome. The resulting TK.sup.(−) recombinant can be selected by culturing the cells in the presence of 5-bromodeoxyuridine and picking viral plaques resistant thereto.

A vaccinia-based infection/transfection system can be conveniently used to provide for inducible, transient expression or coexpression of one or more polypeptides described herein in host cells of an organism. In this particular system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide or polynucleotides of interest, driven by a T7 promoter. The polymerase expressed in the cytoplasm from the vaccinia virus recombinant transcribes the transfected DNA into RNA which is then translated into polypeptide by the host translational machinery. The method provides for high level, transient, cytoplasmic production of large quantities of RNA and its translation products. See, e.g., Elroy-Stein and Moss, Proc. Natl. Acad. Sci. USA (1990) 87:6743–6747; Fuerst et al. Proc. Natl. Acad. Sci. USA (1986) 83:8122–8126.

Alternatively, avipoxviruses, such as the fowlpox and canarypox viruses, can also be used to deliver the coding sequences of interest. Recombinant avipox viruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses. See, e.g., WO 91/12882; WO 89/03429; and WO 92/03545.

Any of a number of alphavirus vectors can also be used for delivery of polynucleotide compositions of the present invention, such as those vectors described in U.S. Pat. Nos. 5,843,723; 6,015,686; 6,008,035 and 6,015,694. Certain vectors based on Venezuelan Equine Encephalitis (VEE) can also be used, illustrative examples of which can be found in U.S. Pat. Nos. 5,505,947 and 5,643,576.

Moreover, molecular conjugate vectors, such as the adenovirus chimeric vectors described in Michael et al. J. Biol. Chem. (1993) 268:6866–6869 and Wagner et al. Proc. Natl. Acad. Sci. USA (1992) 89:6099–6103, can also be used for gene delivery under the invention.

Additional illustrative information on these and other known viral-based delivery systems can be found, for example, in Fisher-Hoch et al., *Proc. Natl. Acad. Sci. USA* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *Proc. Natl. Acad. Sci. USA* 91:215–219, 1994; Kass-Eisler et al., *Proc. Natl. Acad. Sci. USA* 90:11498–11502, 1993; Guzman et al., *Circulation* 88:2838–2848, 1993; and Guzman et al., *Cir. Res.* 73:1202–1207, 1993.

In certain embodiments, a polynucleotide may be integrated into the genome of a target cell. This integration may be in the specific location and orientation via homologous recombination (gene replacement) or it may be integrated in a random, non-specific location (gene augmentation). In yet further embodiments, the polynucleotide may be stably maintained in the cell as a separate, episomal segment of DNA. Such polynucleotide segments or "episomes" encode sequences sufficient to permit maintenance and replication independent of or in synchronization with the host cell cycle. The manner in which the expression construct is delivered to a cell and where in the cell the polynucleotide remains is dependent on the type of expression construct employed.

In another embodiment of the invention, a polynucleotide is administered/delivered as "naked" DNA, for example as described in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

In still another embodiment, a composition of the present invention can be delivered via a particle bombardment approach, many of which have been described. In one illustrative example, gas-driven particle acceleration can be achieved with devices such as those manufactured by Powderject Pharmaceuticals PLC (Oxford, UK) and Powderject Vaccines Inc. (Madison, Wis.), some examples of which are described in U.S. Pat. Nos. 5,846,796; 6,010,478; 5,865,796; 5,584,807; and EP Pat. No. 0500 799. This approach offers a needle-free delivery approach wherein a dry powder formulation of microscopic particles, such as polynucleotide or polypeptide particles, are accelerated to high speed within a helium gas jet generated by a hand held device, propelling the particles into a target tissue of interest.

In a related embodiment, other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

According to another embodiment, the pharmaceutical compositions described herein will comprise one or more immunostimulants in addition to the immunogenic polynucleotide, polypeptide, antibody, T-cell and/or APC compositions of this invention. An immunostimulant refers to essentially any substance that enhances or potentiates an immune response (antibody and/or cell-mediated) to an exogenous antigen. One preferred type of immunostimulant comprises an adjuvant. Many adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

Within certain embodiments of the invention, the adjuvant composition is preferably one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffinan, *Ann. Rev. Immunol.* 7:145–173, 1989.

Certain preferred adjuvants for eliciting a predominantly Th1-type response include, for example, a combination of monophosphoryl lipid A, preferably 3-de-O-acylated monophosphoryl lipid A, together with an aluminum salt. MPL® adjuvants are available from Corixa Corporation (Seattle, Wash.; see, for example, U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Another preferred adjuvant comprises a saponin, such as Quil A, or derivatives thereof, including QS21 and QS7 (Aquila Biopharmaceuticals Inc., Framingham, Mass.); Escin; Digitonin; or Gypsophila or Chenopodium quinoa saponins. Other preferred formulations include more than one saponin in the adjuvant combinations of the present invention, for example combinations of at least two of the following group comprising QS21, QS7, Quil A, β-escin, or digitonin.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol$^R$ to increase viscosity, or may be formulated in a dry powder form with a powder excipient such as lactose.

In one preferred embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 is disclosed in WO 00/09159. Preferably the formulation additionally comprises an oil in water emulsion and tocopherol.

Additional illustrative adjuvants for use in the pharmaceutical compositions of the invention include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Enhanzyn®) (Corixa, Hamilton, Mont.), RC.–529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

Other preferred adjuvants include adjuvant molecules of the general formula

$$HO(CH_2CH_2O)_n\text{—}A\text{—}R, \qquad (I)$$

wherein, n is 1–50, A is a bond or —C(O)—, R is $C_{1-50}$ alkyl or Phenyl $C_{50}$ alkyl.

One embodiment of the present invention consists of a vaccine formulation comprising a polyoxyethylene ether of general formula (I), wherein n is between 1 and 50, preferably 4–24, most preferably 9; the R component is $C_{1-50}$, preferably $C_4$–$C_{20}$ alkyl and most preferably $C_{12}$ alkyl, and A is a bond. The concentration of the polyoxyethylene ethers should be in the range 0.1–20%, preferably from 0.1–10%, and most preferably in the range 0.1–1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index ($12^{th}$ edition: entry 7717). These adjuvant molecules are described in WO 99/52549.

The polyoxyethylene ether according to the general formula (I) above may, if desired, be combined with another adjuvant. For example, a preferred adjuvant combination is preferably with CpG as described in the pending UK patent application GB 9820956.2.

According to another embodiment of this invention, an immunogenic composition described herein is delivered to a host via antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245–251, 1998) and have been shown to be effective as a physiological adjuvant for eliciting prophylactic or therapeutic antitumor immunity (see Timmerman and Levy, Ann. Rev. Med. 50:507–529, 1999). In general, dendritic cells may be identified based on their typical shape (stellate in situ, with marked cytoplasmic processes (dendrites) visible in vitro), their ability to take up, process and present antigens with high efficiency and their ability to activate naive T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., Nature Mecl. 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4–1BB).

APCs may generally be transfected with a polynucleotide of the invention (or portion or other variant thereof) such that the encoded polypeptide, or an immunogenic portion thereof, is expressed on the cell surface. Such transfection may take place ex vivo, and a pharmaceutical composition comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

While any suitable carrier known to those of ordinary skill in the art may be employed in the pharmaceutical compositions of this invention, the type of carrier will typically vary depending on the mode of administration. Compositions of the present invention may be formulated for any appropriate manner of administration, including for example, topical, oral, nasal, mucosal, intravenous, intracranial, intraperitoneal, subcutaneous and intramuscular administration.

Carriers for use within such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

In another illustrative embodiment, biodegradable microspheres (e.g., polylactate polyglycolate) are employed as carriers for the compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems. such as described in WO/99 40934, and references cited therein, will also be useful for many applications. Another illustrative carrier/delivery system employs a carrier comprising particulate-protein complexes, such as those described in U.S. Pat. No. 5,928,647, which are capable of inducing a class I-restricted cytotoxic T lymphocyte responses in a host.

The pharmaceutical compositions of the invention will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (see, for example, Mathiowitz et al., Nature Mar. 27, 1997;386(6623):410–4; Hwang et al., Crit Rev Ther Drug Carrier Syst 1998;15(3):243–84; U.S. Pat. No. 5,641,515; U.S. Pat. No. 5,580,579 and U.S. Pat. No. 5,792,451). Tablets, troches, pills, capsules and the like may also contain any of a variety of additional components, for example, a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Of course, any material used in preparing any dosage unit form should be pharmaceutically pure and substantially non-toxic in the amounts employed. In addition, the active compounds may be incorporated into sustained-release preparation and formulations.

Typically, these formulations will contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

In certain circumstances it will be desirable to deliver the pharmaceutical compositions disclosed herein parenterally, intravenously, intramuscularly, or even intraperitoneally. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described, e.g., in U.S. Pat. No. 5,756,353 and U.S. Pat. No. 5,804,212. Likewise, the delivery of drugs using intranasal microparticle resins (Takenaga et al., J. Controlled Release Mar 2, 1998;52(1–2):81–7) and lysophosphatidyl-glycerol compounds (U.S. Pat. No. 5,725,871) are also well-known in the pharmaceutical arts. Likewise, illustrative transmucosal drug delivery in the form of a polytetrafluoroetheylene support matrix is described in U.S. Pat. No. 5,780,045.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol July 1998;16(7):307–21; Takakura, Nippon Rinsho March 1998;56(3):691–5; Chandran et al., Indian J. Exp Biol. August 1997;35(8):801–9; Margalit, Crit Rev Ther Drug Carrier Syst. 1995;12(2–3):233–61; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally difficult to transfect by other procedures, including T cell suspensions, primary hepatocyte cultures and PC 12 cells (Renneisen et al., J. Biol Chem. Sep. 25, 1990;265(27):16337–42; Muller et al., DNA Cell Biol. April 1990;9(3):221–9). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, he use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev Ind Pharm. December 1998;24(12):1113–28). To avoid side effects due to intracellular polymeric overloading, such ultrafine particles (sized around 0.1 $\mu$m) may be designed using polymers able to be degraded in vivo. Such particles can be made as described, for example, by Couvreur et al., Crit Rev Ther Drug Carrier Syst. 1988;5(1):1–20; zur Muhlen et al., Eur J. Pharm Biopharm. March 1998;45(2):149–55; Zambaux et al. J. Controlled Release. Jan. 2, 1998;50(1–3):31–40; U.S. Pat. No. 5,145,684.

Cancer Therapeutic Methods

In further aspects of the present invention, the pharmaceutical compositions described herein may be used for the treatment of cancer, particularly for the immunotherapy of ovarian cancer. Within such methods, the pharmaceutical compositions described herein are administered to a patient, typically a warm-blooded animal, preferably a human. A patient may or may not be afflicted with cancer. Accordingly, the above pharmaceutical compositions may be used to prevent the development of a cancer or to treat a patient afflicted with a cancer. Pharmaceutical compositions and vaccines may be administered either prior to or following surgical removal of primary tumors and/or treatment such as administration of radiotherapy or conventional chemotherapeutic drugs. As discussed above, administration of the pharmaceutical compositions may be by any suitable method, including administration by intravenous, intraperitoneal, intramuscular, subcutaneous, intranasal, intradermal, anal, vaginal, topical and oral routes.

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157: 177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions described herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 μg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

Cancer Detection and Diagnostic Compositions, Methods and Kits

In general, a cancer may be detected in a patient based on the presence of one or more ovarian tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as ovarian cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding an ovarian tumor protein, which is also indicative of the presence or absence of a cancer. In general, a ovarian tumor sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length ovarian tumor proteins and polypeptide portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 μg, and preferably about 100 ng to about 1 μg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS)

prior to incubation. In general, an appropriate contact time (i.e., incubation time) is a period of time that is sufficient to detect the presence of polypeptide within a sample obtained from an individual with ovarian cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as ovarian cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use tumor polypeptides to detect antibodies that bind to such polypeptides in a biological sample. The detection of such tumor protein specific antibodies may correlate with the presence of a cancer.

A cancer may also, or alternatively, be detected based on the presence of T cells that specifically react with a tumor protein in a biological sample. Within certain methods, a biological sample comprising $CD4^+$ and/or $CD8^+$ T cells isolated from a patient is incubated with a tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with polypeptide (e.g., 5–25 $\mu$g/ml). It may be desirable to incubate another aliquot of a T cell sample in the absence of tumor polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a tumor protein in a biological sample. For example, at least two oligonucleotide primers may be employed in a polymerase chain reaction (PCR) based assay to amplify a portion of a tumor cDNA derived from a biological sample, wherein at least one of the oligonucleotide primers is specific for (i.e., hybridizes to) a polynucleotide encoding the tumor protein. The amplified cDNA is then separated and detected using techniques well known in the art, such as gel electrophoresis. Similarly, oligonucleotide probes that specifically hybridize to a polynucleotide encoding a tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a tumor protein of the invention that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence as disclosed herein. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, N.Y., 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the compositions described herein may be used as markers for the progression of cancer. In this embodiment, assays as described above for the diagnosis of a cancer may be performed over time, and the change in the level of reactive polypeptide(s) or polynucleotide(s) evaluated. For example, the assays may be performed every 24–72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a tumor protein in a biological sample. Such kits generally comprise at least one oligonucleotide probe or primer, as described above, that hybridizes to a polynucleotide encoding a tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a tumor protein.

The following Examples are offered by way of illustration and not by way of limitation.

EXAMPLES

Example 1

Identification of Representative Ovarian Carcinoma cDNA Sequences

Primary ovarian tumor and metastatic ovarian tumor cDNA libraries were each constructed in kanamycin resistant pZErO™-2 vector (Invitrogen) from pools of three different ovarian tumor RNA samples. For the primary ovarian tumor library, the following RNA samples were used: (1) a moderately differentiated papillary serous carcinoma of a 41 year old, (2) a stage IIIC ovarian tumor and (3) a papillary serous adenocarcinoma for a 50 year old caucasian. For the metastatic ovarian tumor library, the RNA samples used were omentum tissue from: (1) a metastatic poorly differentiated papillary adenocarcinoma with psammoma bodies in a 73 year old, (2) a metastatic poorly differentiated adenocarcinoma in a 74 year old and (3) a metastatic poorly differentiated papillary adenocarcinoma in a 68 year old.

The number of clones in each library was estimated by plating serial dilutions of unamplified libraries. Insert data were determined from 32 primary ovarian tumor clones and 32 metastatic ovarian tumor clones. The library characterization results are shown in Table I.

TABLE I

Characterization of cDNA Libraries

| Library | # Clones in Library | Clones with Insert (%) | Insert Size Range (bp) | Ave Insert Size (bp) |
|---|---|---|---|---|
| Primary Ovarian Tumor | 1,258,000 | 97 | 175–8000 | 2356 |
| Metastatic Ovarian Tumor | 1,788,000 | 100 | 150–4300 | 1755 |

Four subtraction libraries were constructed in ampicillin resistant pcDNA3.1 vector (Invitrogen). Two of the libraries were from primary ovarian tumors and two were from metastatic ovarian tumors. In each case, the number of restriction enzyme cuts within inserts was minimized to generate full length subtraction libraries. The subtractions were each done with slightly different protocols, as described in more detail below.

A. POTS 2 Library: Primary Ovarian Tumor Subtraction Library

| | |
|---|---|
| Tracer: | 10 µg primary ovarian tumor library, digested with Not I |
| Driver: | 35 µg normal pancreas in pcDNA3.1(+) |
| | 20 µg normal PBMC in pcDNA3.1(+) |
| | 10 µg normal skin in pcDNA3.1(+) |
| | 35 µg normal bone marrow in pZErO ™ -2 |
| | Digested with Bam HI/Xho I/Sca I |

Two hybridizations were performed, and Not 1-cut pcDNA3.1(+) was the cloning vector for the subtracted library. Sequence results for previously unidentified clones that were randomly picked from the subtracted library are presented in Table II.

TABLE II

Ovarian Carcinoma Sequences

| Sequence | SEQ ID NO |
|---|---|
| 21909 | 2 |
| 21920 | 9 |
| 21921 | 10 |
| 25099 | 143 |
| 25101 | 144 |
| 25103 | 145 |
| 25107 | 146 |
| 25111 | 148 |
| 25113 | 149 |
| 25115 | 150 |
| 25116 | 151 |
| 25752 | 156 |
| 25757 | 158 |
| 25769 | 161 |
| 21907 | 1 |
| 21911 | 5 |
| 25763 | 160 |
| 25770 | 162 |

B. POTS 7 Library: Primary Ovarian Tumor Subtraction Library

| | |
|---|---|
| Tracer: | 10 µg primary ovarian tumor library, digested with Not I |
| Driver: | 35 µg normal pancreas in pcDNA3.1(+) |
| | 20 µg normal PBMC in pcDNA3.1(+) |
| | 10 µg normal skin in pcDNA3.1(+) |
| | 35 µg normal bone marrow in pZErO ™ -2 |
| | Digested with Bam HI/Xho I/Sca I |
| | ~25 µg pZErO ™ -2, digested with Bam HI and Xho I |

Two hybridizations were performed, and Not I-cut pcDNA3.1(+) was the cloning vector for the subtracted library. Sequence results for previously unidentified clones that were randomly picked from the subtracted library are presented in Table III.

TABLE III

Ovarian Carcinoma Sequences

| Sequence | SEQ ID NO |
|---|---|
| 24937 | 125 |
| 24940 | 128 |
| 24946 | 132 |
| 24950 | 133 |
| 24951 | 134 |
| 24956 | 137 |
| 25791 | 166 |
| 25796 | 167 |
| 25797 | 168 |
| 25804 | 171 |
| 24955 | 136 |

C. OS1D Library: Metastatic Ovarian Tumor Subtraction Library

| | |
|---|---|
| Tracer: | 10 µg metastatic ovarian library in pZErO ™ -2, digested with Not I |
| Driver: | 24.5 µg normal pancreas in pcDNA3.1 |
| | 14 µg normal PBMC in pcDNA3.1 |
| | 14 µg normal skin in pcDNA3.1 |
| | 24.5 µg normal bone marrow in pZErO ™ -2 |
| | 50 µg pZErO ™ 2, digested with Bam HI/Xho I/Sfu I |

Three hybridizations were performed, and the last two hybridizations were done with an additional 15 µg of biotinylated pZErO™-2 to remove contaminating pZErO™-2 vectors. The cloning vector for the subtracted library was pcDNA3.1/Not I cut. Sequence results for previously unidentified clones that were randomly picked from the subtracted library are presented in Table IV.

TABLE IV

Ovarian Carcinoma Sequences

| Sequence | SEQ ID NO |
|---|---|
| 24635 | 57 |
| 24647 | 63 |
| 24661 | 69 |
| 24663 | 70 |
| 24664 | 71 |
| 24670 | 72 |
| 24675 | 75 |
| 23645.1 | 13 |
| 23660.1 | 16 |
| 23666.1 | 19 |
| 23679.1 | 23 |
| 24651 | 65 |
| 24683 | 78 |

D. OS1F Library: Metastatic Ovarian Tumor Subtraction Library

| | |
|---|---|
| Tracer: | 10 μg metastatic ovarian tumor library, digested with Not I |
| Driver: | 12.8 μg normal pancreas in pcDNA3.1 |
| | 7.3 μg normal PBMC in pcDNA3.1 |
| | 7.3 μg normal skin in pcDNA3.1 |
| | 12.8 μg normal bone marrow in pZErO ™ -2 |
| | 25 μg pZErO ™ -2, digested with Bam HI/Xho I/Sfu I |

One hybridization was performed. The cloning vector for the subtracted library was pcDNA3.1/Not I cut. Sequence results for previously unidentified clones that were randomly picked from the subtracted library are presented in Table V.

TABLE V

Ovarian Carcinoma Sequences

| Sequence | SEQ ID NO |
|---|---|
| 24344 | 33 |
| 24356 | 42 |
| 24368 | 53 |
| 24696 | 86 |
| 24699 | 89 |
| 24701 | 90 |
| 24703 | 91 |
| 24707 | 95 |
| 24709 | 97 |
| 24732 | 111 |
| 24745 | 120 |
| 24746 | 121 |
| 24337 | 28 |
| 24348 | 35 |
| 24351 | 38 |
| 24358 | 44 |
| 24360 | 46 |
| 24361 | 47 |

TABLE V-continued

Ovarian Carcinoma Sequences

| Sequence | SEQ ID NO |
|---|---|
| 24690 | 81 |
| 24692 | 82 |
| 24694 | 84 |
| 24705 | 93 |
| 24711 | 98 |
| 24713 | 99 |
| 24727 | 107 |
| 24741 | 17 |
| 24359 (78% Human mRNA for KIAA0111 gene, complete cds) | 45 |
| 24336 (79% with *H. sapiens* mitochondrial genome (consensus sequence)) | 27 |
| 24737 (84% Human ADP/ATP translocase mRNA) | 114 |
| 24363 (87% Homo sapiens eukaryotic translation elongation factor 1 alpha 1 (EEF1A1) | 49 |
| 24357 (87% *S. scrofa* mRNA for UDP glucose pyrophosphorylase) | 43 |
| 24362 (88% Homo sapiens Chromosome 16 BAC clone CIT987SK-A-233A7) | 48 |
| 24704 (88% Homo sapiens chromosome 9, clone hRPK.401_G_18) | 92 |
| 24367 (89% Homo sapiens 12p13.3 BAC RCPI11-935C2) | 52 |
| 24717 (89% Homo sapiens proliferation-associated gene A (natural killer-enhancing factor A) (PAGA) | 103 |
| 24364 (89% Human DNA sequence from PAC 27K14 on chromosome Xp11.3–Xp11.4) | 50 |
| 24355 (91% Homo sapiens chromosome 17, clone hCIT.91_J_4) | 41 |
| 24341 (91% Homo sapiens chromosome 5, BAC clone 249h5 (LBNL H149) | 32 |
| 24714 (91% Human DNA sequence from clone 125N5 on chromosome 6q26–27) | 100 |

The sequences in Table VI, which correspond to known sequences, were also identified in the above libraries.

TABLE IV

Ovarian Carcinoma Sequences

| Identity | SEQ ID NO | Sequence | Library |
|---|---|---|---|
| Genomic sequence from Human 9q34 | 56 | 24634 | OS1D |
| Homo sapiens 12p13.3 PAC RPCI1-96H9 (Roswell Park Cancer Institute Human PACLibrary) | 66 | 24653 | OS1D |
| Homo sapiens annexin II (lipocortin II) (ANX2) mRNA | 60 | 24640 | OS1D |
| Homo sapiens eukaryotic translation elongation factor 1 alpha 1 (EEF1A1) | 55 | 24627 | OS1D |
| Homo sapiens ferritin, heavy polypeptide 1 (FTH1) | 64 | 24648 | OS1D |
| Homo sapiens FK506-binding protein 1A (12kD) (FKBP1A) mRNA | 22 | 23677.1 | OS1D |
| Homo sapiens growth arrest specific transcript 5 gene | 73 | 24671 | OS1D |
| Homo sapiens keratin 18 (KRT18) mRNA | 68 | 24657 | OS1D |
| Homo sapiens mRNA; cDNA DKFZp564H182 | 76 | 24677 | OS1D |
| Homo sapiens ribosomal protein S7 (RPS7) | 74 | 24673 | OS1D |
| Homo sapiens ribosomal protein, large, P0 (RPLP0) mRNA | 14 | 23647.1 | OS1D |
| Homo sapiens T cell-specific tyrosine kinase mRNA | 67 | 24655 | OS1D |
| Homo sapiens tubulin, alpha, ubiquitous (K-ALPHA-1) | 61 | 24642 | OS1D |
| HSU78095 Homo sapiens placental bikunin mRNA | 18 | 23662.1 | OS1D |
| Human BAC clone GS055K18 from 7p15-p21 | 11 | 23636.1 | OS1D |
| Human insulin-like growth factor-binding protein-3 gene | 58 | 24636 | OS1D |
| Human mRNA for ribosomal protein | 79 | 24687 | OS1D |
| Human non-histone chromosomal protein HMG-14 mRNA | 62 | 24645 | OS1D |
| Human ribosomal protein L3 mRNA, 3' end | 59 | 24638 | OS1D |
| Human TSC-22 protein mRNA | 77 | 24679 | OS1D |

TABLE IV-continued

Ovarian Carcinoma Sequences

| Identity | SEQ ID NO | Sequence | Library |
|---|---|---|---|
| HUMGFIBPA Human growth hormone-dependent insulin-like growth factor-binding protein | 12 | 23637.1 | OS1D |
| HUMMTA Homo sapiens mitochondrial DNA | 17 | 23661.1 | OS1D |
| HUMMTCG Human mitochondrion | 21 | 23673.1 | OS1D |
| HUMT1227HC Human mRNA for TI-227H | 20 | 23669.1 | OS1D |
| HUMTRPM2A Human TRPM-2 mRNA | 15 | 23657.1 | OS1D |
| Genomic sequence from Human 13 | 80 | 24689 | OS1F |
| H. sapiens CpG island DNA genomic Mse1 fragment, clone 84a5 | 104 | 24719 | OS1F |
| H. sapiens RNA for snRNP protein B | 110 | 24730 | OS1F |
| Homo sapiens (clone L6) E-cadherin (CDH1) gene | 108 | 24728 | OS1F |
| Homo sapiens atrophin-1 interacting protein 4 (AIP4) mRNA | 37 | 24350 | OS1F |
| Homo sapiens CGI-08 protein mRNA | 102 | 24716 | OS1F |
| Homo sapiens clone 24452 mRNA sequence | 54 | 24374 | OS1F |
| Homo sapiens clone IMAGE 286356 | 83 | 24693 | OS1F |
| Homo sapiens cornichon protein mRNA | 113 | 24735 | OS1F |
| Homo sapiens hypothetical 43.2 Kd protein mRNA | 87 | 24697 | OS1F |
| Homo sapiens interleukin 1 receptor accessory protein (IL1RAP) mRNA. | 29 | 24338 | OS1F |
| Homo sapiens K-Cl cotransporter KCC4 mRNA, complete cds | 31 | 24340 | OS1F |
| Homo sapiens keratin 8 (KRT8) mRNA | 115 | 24739 | OS1F |
| Homo sapiens mRNA for DEPP (decidual protein induced by progesterone) | 36 | 24349 | OS1F |
| Homo sapiens mRNA for KIAA0287 gene | 101 | 24715 | OS1F |
| Homo sapiens mRNA for KIAA0762 protein | 118 | 24742 | OS1F |
| Homo sapiens mRNA for zinc-finger DNA-binding protein, complete cds | 24 | 24333 | OS1F |
| Homo sapiens mRNA; cDNA DKFZp434K114 | 112 | 24734 | OS1F |
| Homo sapiens mRNA; cDNA DKFZp564E1962 (from clone DKFZp564E1962) | 25 | 24334 | OS1F |
| Homo sapiens nuclear chloride ion channel protein (NCC27) mRNA | 34 | 24345 | OS1F |
| Homo sapiens ribosomal protein L13 (RPL13) | 109 | 24729 | OS1F |
| Homo sapiens senescence-associated epithelial membrane protein (SEMP1) | 94 | 24706 | OS1F |
| Homo sapiens tumor protein, translationally-controlled 1 (TPT1) mRNA. | 26 | 24335 | OS1F |
| Homo sapiens tumor suppressing subtransferable candidate 1 (TSSC1) | 51 | 24366 | OS1F |
| Homo sapiens v-fos FBJ murine osteosarcoma viral oncogene homolog(FOS) mRNA | 85 | 24695 | OS1F |
| Homo sapiens zinc finger protein slug (SLUG) gene | 106 | 24722 | OS1F |
| Human clone 23722 mRNA | 105 | 24721 | OS1F |
| Human clones 23667 and 23775 zinc finger protein mRNA | 119 | 24744 | OS1F |
| Human collagenase type IV mRNA, 3' end. | 39 | 24352 | OS1F |
| Human DNA sequence from PAC 29K1 on chromosome 6p21.3–22.2. | 116 | 24740 | OS1F |
| Human ferritin H chain mRNA | 96 | 24708 | OS1F |
| Human heat shock protein 27 (HSPB1) gene exons 1–3 | 88 | 24698 | OS1F |
| Human mRNA for KIAA0026 gene | 30 | 24339 | OS1F |
| Human mRNA for T-cell cyclophilin | 40 | 24354 | OS1F |
| Genomic sequence from Human 9q34, complete sequence [Homo sapiens] | 140 | 25092 | POTS2 |
| H. sapiens DNA for muscle nicotinic acetylcholine receptor gene promotor, clone ICRFc105F02104 | 3 | 21910 | POTS2 |
| Homo sapiens breast cancer suppressor candidate 1 (bcsc-1) mRNA, complete cds | 142 | 25098 | POTS2 |
| Homo sapiens CGI-151 protein mRNA, complete cds | 8 | 21916 | POTS2 |
| Homo sapiens complement component 3 (C3) gene, exons 1–30. | 4 | 21913 | POTS2 |
| Homo sapiens mRNA for hepatocyte growth factor activator inhibitor type 2, complete cds | 159 | 25758 | POTS2 |
| Homo sapiens preferentially expressed antigen of melanoma (PRAME) mRNA | 153 | 25745 | POTS2 |
| Homo sapiens prepro dipeptidyl peptidase I (DPP-I) gene, complete cds | 152 | 25117 | POTS2 |
| Homo sapiens SKB1 (S. cerevisiae) homolog (SKB1) mRNA. | 147 | 25110 | POTS2 |
| Homo sapiens SWI/SNF related, matrix associated, actin dependent regulator of chromatin, subfamily a, member 4 (SMARCA4) | 6 | 25914 | POTS2 |

TABLE IV-continued

Ovarian Carcinoma Sequences

| Identity | SEQ ID NO | Sequence | Library |
|---|---|---|---|
| Human 12S RNA induced by poly(rI), poly(rC) and Newcastle disease virus | 155 | 25749 | POTS2 |
| Human ferritin Heavy subunit mRNA, complete cds. | 7 | 21915 | POTS2 |
| Human glyceraldehyde-3-phosphate dehydrogenase (GAPDH) mRNA, complete cds. | 141 | 25093 | POTS2 |
| Human mRNA for fibronectin (FN precursor) | 157 | 25755 | POTS2 |
| Human translocated t(8;14) c-myc (MYC) oncogene, exon 3 and complete cds | 154 | 25746 | POTS2 |
| H. sapiens vegf gene, 3'UTR | 169 | 25799 | POTS7 |
| Homo sapiens 30S ribosomal protein S7 homolog mRNA, complete cds | 170 | 25802 | POTS7 |
| Homo sapiens acetyl-Coenzyme A acetyltransferase 2 (acetoacetyl Coenzyme A thiolase) (ACAT2) mRNA | 172 | 25808 | POTS7 |
| Homo sapiens amyloid beta precursor protein-binding protein I, 59kD (APPBP1) mRNA. | 138 | 24959 | POTS7 |
| Homo sapiens arylacetamide deacetylase (esterase) (AADAC) mRNA. | 129 | 24942 | POTS7 |
| Homo sapiens clone 23942 alpha enolase mRNA, partial cds | 165 | 25787 | POTS7 |
| Homo sapiens echinoderm microtubule-associated protein-like EMAP2 mRNA, complete cds | 130 | 24943 | POTS7 |
| Homo sapiens IMP (inosine monophosphate) dehydrogenase 2 (IMPDH2) mRNA | 164 | 25775 | POTS7 |
| Homo sapiens megakaryocyte potentiating factor (MPF) mRNA. | 126 | 24938 | POTS7 |
| Homo sapiens mRNA for KIAA0552 protein, complete cds | 163 | 25771 | POTS7 |
| Homo sapiens Norrie disease protein (NDP) mRNA | 173 | 25809 | POTS7 |
| Homo sapiens podocalyxin-like (PODXL) mRNA. | 131 | 24944 | POTS7 |
| Homo sapiens synaptogyrin 2 (SYNGR2) mRNA. | 135 | 24952 | POTS7 |
| Human aldose reductase mRNA, complete cds. | 139 | 24969 | POTS7 |
| Human cyclooxygenase-1(PTSG1) mRNA, partial cds | 124 | 24935 | POTS7 |
| Human H19 RNA gene, complete cds. | 122 | 24933 | POTS7 |
| Human mRNA for Apo1_Human (MER5(Aop1-Mouse)-like protein), complete cds | 127 | 24939 | POTS7 |
| Human triosephosphate isomerase mRNA, complete cds. | 123 | 24934 | POTS7 |

Still further ovarian carcinoma polynucleotide and/or polypeptide sequences identified from the above libaries are provided below in Table VII. Sequences O574S (SEQ ID NOs: 183&185), O584S (SEQ ID NO: 193) and O585S (SEQ ID NO: 194) represent novel sequences. The remaining sequences exhibited at least some homology with known genomic and/or EST sequences.

TABLE VII

| SEQ ID: | Sequence | Library |
|---|---|---|
| 174: | O565S_CRABP | OS1D |
| 175: | O566S_Ceruloplasmin | POTS2 |
| 176: | O567S_41191.SEQ(1 > 487) | POTS2 |
| 177: | O568S_KIAA0762.seq(1 > 3999) | POTS7 |
| 178: | O569S_41220.seq(1 > 1069) | POTS7 |
| 179: | O570S_41215.seq(1 > 1817) | POTS2 |
| 180: | O571S_41213.seq(1 > 2382) | POTS2 |
| 181: | O572S_41208.seq(1 > 2377) | POTS2 |
| 182: | O573S_41177.seq(1 > 1370) | OS1F |
| 183: | O574S_47807.seq(1 > 2060) | n/a |
| 184: | O568S/VSGF DNA seq | n/a |
| 185: | O574S_47807.seq(1 > 3000) | n/a |
| 186: | O568S/VSGF protein seq | n/a |
| 187: | 449H1(57581) | OS1D |
| 188: | 451E12(57582) | OS1D |
| 189: | 453C7_3'(57583.1)Osteonectin | OS1D |
| 190: | 453C7_5'(57583.2) | OS1D |
| 191: | 456G1_3'(57584.1)Neurotensin | OS1F |
| 192: | 456G1_5'(57584.2) | OS1F |
| 193: | O584S_465G5(57585) | OS1F |
| 194: | O585S_469B12(57586) | POTS2 |
| 195: | O569S_474C3(57587) | POTS7 |
| 196: | 483B1_3'(24934.1)Triosephosphate | POTS7 |
| 197: | 57885 Human preferentially expressed antigen of melanoma | POTS2 |
| 198: | 57886 Chromosome 22q12.1 clone CTA-723E4 | POTS2 |
| 199: | 57887 Homologous to mouse brain cDNA clone MNCb-0671 | POTS2 |

Further studies on the clone of SEQ ID NO: 182 (also referred to as O573S) led to the identification of multiple open reading frames that encode the amino acid sequences of SEQ ID NO: 200–202.

Example 2

Analysis of cDNA Expression Using Microarray Technology

In additional studies, sequences disclosed herein were found to be overexpressed in specific tumor tissues as determined by microarray analysis. Using this approach, cDNA sequences are PCR amplified and their mRNA expression profiles in tumor and normal tissues are examined using cDNA microarray technology essentially as described (Shena et al., 1995). In brief, the clones are arrayed onto glass slides as multiple replicas, with each location corresponding to a unique cDNA clone (as many as 5500 clones can be arrayed on a single slide or chip). Each chip is hybridized with a pair of cDNA probes that are fluorescence-labeled with Cy3 and Cy5 respectively. Typically, 1 μg of polyA+ RNA is used to generate each cDNA probe. After hybridization, the chips are scanned and the fluorescence intensity recorded for both Cy3 and Cy5 channels. There are multiple built-in quality control steps. First, the probe quality is monitored using a panel of ubiquitously expressed genes. Secondly, the control plate also can include yeast DNA fragments of which complementary RNA may be spiked into the probe synthesis for measuring the quality of the probe and the sensitivity of the analysis. Currently, the technology offers a sensitivity of 1 in 100,000 copies of mRNA. Finally, the reproducitility of this technology can be ensured by including duplicated control cDNA elements at different locations.

The microarray results for clones 57885 (SEQ ID NO:197), 57886 (SEQ ID NO:198) and 57887 (SEQ ID NO:199) are as follows.

Clone 57885: 16/38 (42%) of ovarian tumors showed an expression signal value of >0.4. The mean value for all ovary tumors was 0.662 with a mean value of 0.187 for all normal tissues, which yields a 3.64 fold overexpression level in ovary tumor relative to essential normal tissues. Normal tissue expression was elevated (>0.4) in peritoneum, skin and thymus.

Clone 57886: 16/38 (420/o) of ovarian tumors showed an expression signal value of >0.4. The mean value for all ovary tumors was 0.574 with a mean value of 0.166 for all normal tissues which yields a 3.46 fold overexpression level in ovary tumor relative to essential normal tissues. Normal tissue expression was elevated (>0.4) in heart, pancreas and small intestive.

Clone 57887: 17/38 (44%) of ovarian tumors showed an expression signal value of >0.4. The mean value for all ovary tumors is 0.744 with a mean value of 0.184 for all normal tissues which yields a 4.04 fold overexpression level in ovary tumor relative to essential normal tissues. Normal tissue expression was elevated (>0.4) in esophagus.

Example 3

Synthesis of Polypeptides

Polypeptides are synthesized on a Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence is attached to the amino terminus of the peptide to provide a method of conjugation, binding to an immobilized surface, or labeling of the peptide. Cleavage of the peptides from the solid support is carried out using the following cleavage mixture: trifluoroacetic acid:ethanedithiol:thioanisole:water:phenol (40:1:2:2:3). After cleaving for 2 hours, the peptides are precipitated in cold methyl-t-butyl-ether. The peptide pellets are then dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) is used to elute the peptides. Following lyophilization of the pure fractions, the peptides are characterized using electrospray or other types of mass spectrometry and by amino acid analysis.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed:

1. A method for determining the presence of ovarian cancer in a patient, comprising the steps of:
   (a) contacting a biological sample obtained from a patient with a probe consisting of 50 to 607 contiguous nucleotides of SEQ ID NO:198 or the complement thereof;
   (b) detecting in the sample an amount of an expressed polynucleotide that hybridizes to the probe under moderately stringent conditions; and
   (c) comparing the amount of expressed polynucleotide that hybridizes to the probe to a predetermined cut-off value, and therefrom determining the presence of ovarian cancer in the patient.

2. The method of claim 1 wherein probe consists of 100 to 200 contiguous nucleotides of SEQ ID NO:198 or the complement thereof.

3. A method for determining the presence of ovarian cancer in a patient, comprising the steps of:
   (a) contacting a biological sample obtained from a patient with at least two oligonucleotide primers, each primer consisting of 10 to 607 contiguous nucleotides of SEQ ID NO:198 or the complement thereof, in a reverse transcriptase polymerase chain reaction, wherein said oligonucleotide primers are capable of amplifying an expressed polynucleotide sequence recited in SEQ ID NO:198; and
   (b) detecting in the sample an amount of an expressed polynucleotide sequence that amplifies in the presence of said oligonucleotide primers;
   (c) comparing the amount of expressed polynucleotide that amplifies in the presence of said oligonucleotides to a pre-determined cut off value, and therefrom determining the presence of ovarian cancer in the patient.

4. The method of claim 3, wherein each primer consists of 15 to 200 contiguous nucleotides of SEQ ID NO:198 or the complement thereof.

5. The method of claim 3, wherein each primer consists of 20 to 100 contiguous nucleotides of SEQ ID NO:198 or the complement thereof.

6. The method of claim 3, wherein each primer consists of 15 to 607 contiguous nucleotides of SEQ ID NO:198 or the complement thereof.

7. The method of claim 3, wherein each primer consists of 20 to 607 contiguous nucleotides of SEQ ID NO:198 or the complement thereof.

8. The method of claim 3, wherein each primer consists of 30 to 607 contiguous nucleotides of SEQ ID NO:198 or the complement thereof.

9. The method of claim 3, wherein each primer consists of 15 to 200 contiguous nucleotides of SEQ ID NO:198 or the complement thereof.

* * * * *